(12) United States Patent
Segers et al.

(10) Patent No.: US 6,783,764 B1
(45) Date of Patent: Aug. 31, 2004

(54) ACTINOBACILLUS PLEUROPNEUMONIAE SUBUNIT VACCINE

(75) Inventors: Ruud Philip Antoon Maria Segers, Boxmeer (NL); Joachim Frey, Schupfen (CH)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/387,693

(22) Filed: Aug. 31, 1999

Related U.S. Application Data

(63) Continuation of application No. 09/057,570, filed on Apr. 9, 1998, now Pat. No. 6,013,266.

(30) Foreign Application Priority Data

Oct. 4, 1997 (EP) .............................................. 97201032

(51) Int. Cl.[7] ........................ A61K 49/00; A61K 39/00; A61K 39/38; A61K 39/385; A61K 39/02
(52) U.S. Cl. .................. 424/236.1; 424/9.2; 424/184.1; 424/192.1; 424/193.1; 424/197.11; 424/234.1; 424/236.1; 424/278.1; 435/220; 435/235.1; 435/340; 930/200
(58) Field of Search ........................... 424/255.1, 256.1, 424/235.1, 200.1, 201.7, 93.2, 93.46, 203.1, 236.1, 93.4; 435/71.3, 252.3, 243, 245

(56) References Cited

FOREIGN PATENT DOCUMENTS

AU     WO97/16532    * 11/1995 ............ C12N/1/21

OTHER PUBLICATIONS

Rosendal et al. 1990. Amer. J. of Vet. Res. 51(5): 711–717.*
Tascon et al. 1994. Mol. Micro. 14(2): 207–216.*
Anerson et al. 1991. Infection and Immunity. 59(11): 4110–4116.*
Frey. 1995. trends in Microbio. 3(7): 257–261.*
Jansen et al. 1995. Infect. & Immun. 63(1): 23–37.*
Michalski et al. 1993. Infect. & Immuno.61(10): 4462–4468.*
Jansen et al., Infection and Immunity, 63:1:27–37, 1995.
Rosendal et al., American Journal of Veterinary Medicine, 51:5:711–717, 1990.
Anderson et al., Infection and Immunity, 59:11:4110–4116, 1991.
J. Frey et al., Trends in Microbiology, 3:7:257–261, 1995.
Frey et al., Schweizer Archiv Für Tierheilkunde, 138:3:121–124, 1996.
Timothy J. Anderson, Thesis, University of Guelph, Nov. 1995, "Characterization of the LACZ, GALK and GALM Genes of Actinobacillus pleuropneumoniae".

* cited by examiner

Primary Examiner—Lynette R. F. Smith
Assistant Examiner—JaNa Hines
(74) Attorney, Agent, or Firm—William P. Raine, III

(57) ABSTRACT

The present invention relates to live attenuated bacteria of the genus Actinobacillus pleuropneumoniae that have a mutation in an apxIV gene such that no functional ApxIV toxin can be produced. The invention also relates to methods for the production of such bacteria. Also vaccines comprising such bacteria and methods for the production of such vaccines are part of the invention. The invention further relates to subunit vaccines comprising an ApxIV toxin, to methods for the production of such vaccines and to methods for the protection of animals against infection with bacteria of the genus Actinobacillus pleuropneumoniae. In addition, the invention relates to the promotor of the apxIV gene. Finally, the invention relates to diagnostic test for the selective diagnosis of Actinobacillus pleuropneumoniae infections and to diagnostic tests discriminating between Actinobacillus pleuropneumoniae field strains and vaccine strains.

8 Claims, 7 Drawing Sheets

Figure 1:
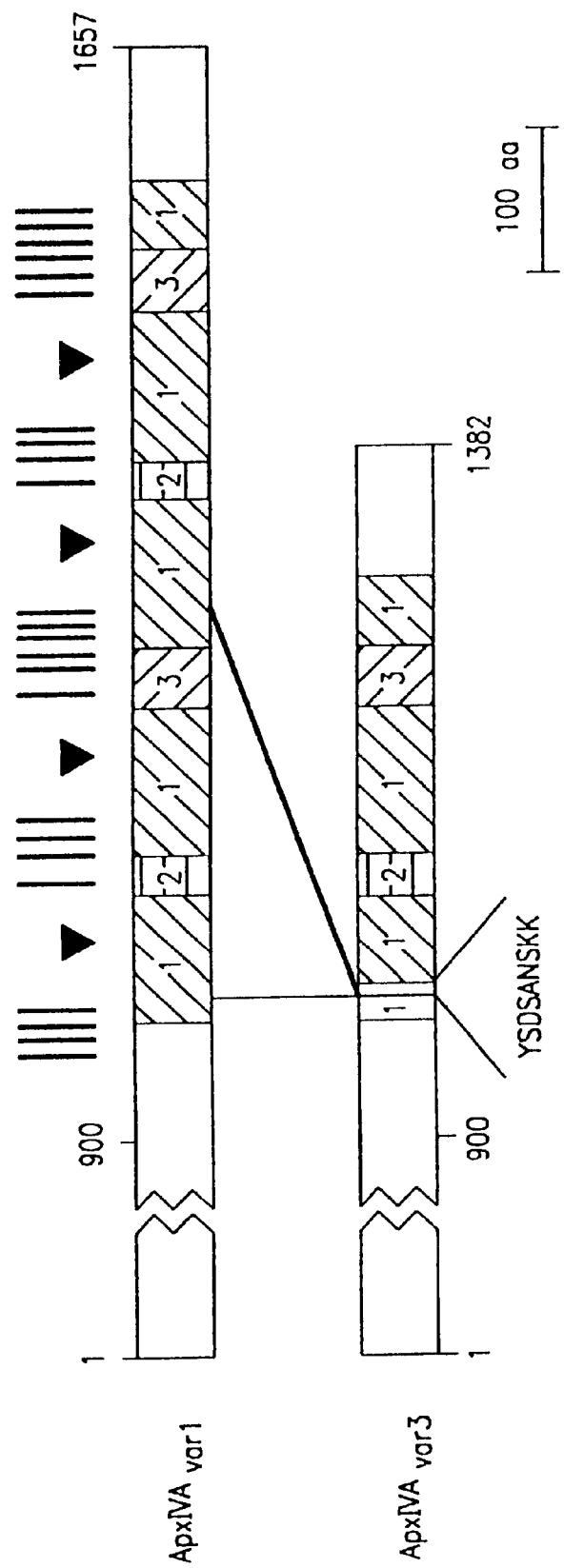

```
                 1                                                          60
REP1var1A        ............ YGADTYIFS KGHGQDIVYE DTNNDNRARD IDTLKFTDVN YAEVKFRRVD
REP1var1B        GGKGNDILRG GYGADTYIFS KGHGQDIVYE DTNNDNRARD IDTLKFTDVN YAEVKFRRVD
REP1var1C        GGKGNDILRG GYGADTYIFS KGHGQDIVYE DTNNDNRARD IDTLKFTDVN YAEVKFRRVD
REP1var1D        GGKGNDILRG GYGADTYIFS KGHGQDIVYE DTNNDNRARD IDTLKFTDVN YAEVKFRRVD
REP1var1E        GGKGNDILRG GYGADTYIFS KGHGQDIVYE DTNNDNRARD IDTLKFTD.. ..........
REP1var3A        ............ YGADTYIFS KGHGQDIVYE .......... ..........D IDTLKFTDVN YAEVKFRRVD
REP1var3B        ............ .......... .......... .......... .......... ..........
REP1var3C        GGKGNDILRG GYGADTYIFS KGHGQDIVYE DTNNDNRARD IDTLTFTDVN YAEVKFRRVD
REP1var3D        GGKGNDILRG GYGADTYIFS KGHGQDIVYE DTNNDNRARD IDTLKFTD.. ..........

61                                                         102
REP1var1A        NDLMLFGYHD TDSVTVKSFY SHVDYQFDKL EFADRSITRD EL        A
REP1var1B        NDLMLFGYHD TDSVTVKSFY NHVDYQFDKL EFADRSITRD EL
REP1var1C        NDLMLFGYHD TDSVTVKSFY SHVDYQFDKL EFADRSITRD EL
REP1var1D        NDLMLFGYHD TDSVTVKSFY NHVDYQFDKL EFADRSITRD EL
REP1var1E        .......... .......... .......... .......... ..
REP1var3A        NDLMLFGYHD TDSVTVKSFY SHVDYQFDKL EFADRSITRD EL
REP1var3B        .......... .......... .......... DFADRSITRD EL
REP1var3C        NDLMLFGYHD TDSVTIKSFY NHVDYQCDKL DFADRSITRD EL
REP1var3D        .......... .......... .......... .......... ..

1                         27
REP2var1A        IKAGLHLYGT DGNDDIKDHA DWDSILE      B
REP2var1B        IKAGLHLYGT DGNDDIKDHA DWDSILE
REP2var3A        IKAGLHLYGT DGNDDIKDHA DWDSIVE 1                                             44
REP3var1A        GKQGMALFGT DGDDNINDWG RNSVIDAGAG NDTVNGGNGD DTLI      C
REP3var1B        GKQGMALFGT DGDDNINDWG RNSVIDAGAG NDTVNGGNGD DTLI
REP3var3A        GKQGMALFGT DGDDNINDWG RNSVIDAGAG NDTVNGGNGD DTLI
```

FIG 2

SEQUENCE LISTING

```
<160> NUMBER OF SEQ ID NOS: 16

<210> SEQ ID NO 1
<211> LENGTH: 6736
<212> TYPE: DNA
<213> ORGANISM: Actinobacillus pleuropneumoniae
<220> FEATURE:
<221> NAME/KEY: CDS
<222> LOCATION: 1576..6549

<400> SEQUENCE: 1
atcgatatgc cgccgggtac gggcgatatc caacttactc tttcgcaaca aattccggtt      60
accggtgcgg tggtggtaac cactccgcaa gatattgcgt tattagatgc ggtgaaaggt     120
atttcaatgt tccaaaaagt gtcggtaccg gtcttaggta tcattgaaaa tatgagcgta     180
catatctgcc aaaattgcgg tcaccacgaa gatattttcg gcaccggcgg tgcggagaaa     240
gtggcgaaga aatacggtac taaagtatta ggacaaatgc cgttgcatat tcgcttacgt     300
caagatttgg atgccggcac accgaccgtc gttgcggcac cggaacacga aaccagccga     360
gcctatattg aattagcggc aaaagtcgct tcggaattat actggcaagg ttcggttatc     420
ccgtctgaaa ttatgattcg tgaagtaaaa taagttttaa taaccacgaa aacacaaaga     480
acacaagcgg tagaatttgc agaaaaattt gcaaatccta ccgctttttt attagtacga     540
ttcgctgttg gactgctatt tgatttggtt tgtcaggata ttatgttatt gtaatgaaat     600
gttagtgaat tattttttatt aatttgaaag gaaacaaaat gaaataaaa aaacgttaca     660 ttgcgctgtt ggtcttaggt gtcgttatca gctatgcctg gtatcaaaat tatcaatggg     720
aacagctgat gttaagcggt tattgtgaaa aggacggaag ttattttgat gataggcata     780
cgaagcaaga actgattgat agggcaatta actatatgct ggagcatcaa tctaaaaaaa     840
catacgatgc ttatactgat gaacctttag aaataaaacc atatttaaca atagaggaat     900
ttaaaaaact caatccaaat tgttgtgaaa ttacctcatg gccagcagat gcagttccac     960
aagattggga tgttcgtgtg gaaggtaagg catataggta tgtaatcgta aaatatttaa    1020
gaaccttagc aaatagagaa cctgaacgat gggaaactag tattgttttt gataattgcg    1080
gcaatcctaa aagagcaagc tacttatatt atttaaagag agaaatttat tatgacaaaa    1140
ttaactatgc aagatgtgac caatttatat ttatataaaa cgaaaactct acctaaagat    1200
agattggatg attcacttat ttctgaaata ggaaaaggag atgatgatat tgatagaaaa    1260
gaatttatgg tggggccggg acgttttgtg accgctgata actttagcgt tgtaagagat    1320 tttttttaatg ctgggaaatc acgcattatt gcgccgcaag tcccgcctat tcgttcacag    1380
caggaaaaaa tcttggtcgg tttaaaaccg ggcaaatatt ccaaagcgca gatattgaa     1440 atgctggtt atacgaaagg cggagaagtg gtaaatggca tgtttgccgg tgaagtccag    1500
acattaggct tttatgacga tggcaaaggg gatttactcg aacgcgccta tatctggaat    1560
accacaggat ttaaa atg agc gac aat gcc ttt ttt gtt ata gaa gaa tca    1611
                 Met Ser Asp Asn Ala Phe Phe Val Ile Glu Glu Ser
```

-continued

```
           1                   5                       10
ggc aaa cgc tat att gaa aac ttt ggt att gaa cct ctt ggt aag caa       1659
Gly Lys Arg Tyr Ile Glu Asn Phe Gly Ile Glu Pro Leu Gly Lys Gln
         15                  20                  25 gaa gat ttt gat ttt gtc ggc ggc ttt tgg tct aac tta gtg aat cgt       1707
Glu Asp Phe Asp Phe Val Gly Gly Phe Trp Ser Asn Leu Val Asn Arg
 30                  35                  40 ggt ttg gaa agt att atc gac cca tcc ggt atc ggt gga acg gta aac       1755
Gly Leu Glu Ser Ile Ile Asp Pro Ser Gly Ile Gly Gly Thr Val Asn
 45                  50                  55                  60 ctt aac ttt acc ggc gag gtg gaa acc tac acg tta gac gaa aca agg       1803
Leu Asn Phe Thr Gly Glu Val Glu Thr Tyr Thr Leu Asp Glu Thr Arg
                 65                  70                  75 ttt aaa gcg gaa gcg gcg aag aaa agc cat tgg agt tta gtg aat gcg       1851
Phe Lys Ala Glu Ala Ala Lys Lys Ser His Trp Ser Leu Val Asn Ala
                 80                  85                  90 gcg aaa gta tac ggc ggt tta gac caa att att aaa aaa cta tgg gac       1899
Ala Lys Val Tyr Gly Gly Leu Asp Gln Ile Ile Lys Lys Leu Trp Asp
                 95                 100                 105 agt ggc tca att aag cat tta tat caa gat aaa gat acg ggc aaa tta       1947
Ser Gly Ser Ile Lys His Leu Tyr Gln Asp Lys Asp Thr Gly Lys Leu
110                 115                 120 aaa ccg att att tac ggc acg gcc ggc aac gac agt aag att gaa ggc       1995
Lys Pro Ile Ile Tyr Gly Thr Ala Gly Asn Asp Ser Lys Ile Glu Gly
125                 130                 135                 140 act aaa atc acc cgt agg att gcg ggt aaa gaa gtt acg ctt gat att       2043
Thr Lys Ile Thr Arg Arg Ile Ala Gly Lys Glu Val Thr Leu Asp Ile
                145                 150                 155 gcc aat cag aaa att gaa aaa ggc gtg tta gag aaa ttg ggg ctg tct       2091
Ala Asn Gln Lys Ile Glu Lys Gly Val Leu Glu Lys Leu Gly Leu Ser
                160                 165                 170 gtt agt ggt tcg gat atc att aaa ttg ttg ttt gga gca ttg act cca       2139
Val Ser Gly Ser Asp Ile Ile Lys Leu Leu Phe Gly Ala Leu Thr Pro
            175                 180                 185 act tta aat aga atg ttg cta tca caa ctt atc cag tct ttt tcc gat       2187
Thr Leu Asn Arg Met Leu Leu Ser Gln Leu Ile Gln Ser Phe Ser Asp
        190                 195                 200 agc ttg gct aaa ctt gat aat ccc tta gcc cct tac act aaa aat ggc       2235
Ser Leu Ala Lys Leu Asp Asn Pro Leu Ala Pro Tyr Thr Lys Asn Gly
205                 210                 215                 220 gtg gtt tat gtc acc ggc aaa ggg aat gat gtg ctt aaa gga act gaa       2283
Val Val Tyr Val Thr Gly Lys Gly Asn Asp Val Leu Lys Gly Thr Glu
                225                 230                 235 cat gag gat ttg ttt ctc ggt ggt gag ggg aat gat act tat tat gcg       2331
His Glu Asp Leu Phe Leu Gly Gly Glu Gly Asn Asp Thr Tyr Tyr Ala
                240                 245                 250 aga gta ggc gat aca att gaa gac gcc gac ggc aaa ggt aaa gtc tat       2379
Arg Val Gly Asp Thr Ile Glu Asp Ala Asp Gly Lys Gly Lys Val Tyr
            255                 260                 265 ttt gtg aga gaa aaa ggg gta cct aag gcg gat cct aag cgg gta gag       2427
Phe Val Arg Glu Lys Gly Val Pro Lys Ala Asp Pro Lys Arg Val Glu
        270                 275                 280 ttt agc gag tac ata acg aaa gaa gaa ata aaa gag gtt gaa aag ggg       2475
Phe Ser Glu Tyr Ile Thr Lys Glu Glu Ile Lys Glu Val Glu Lys Gly
285                 290                 295                 300 tta tta act tac gca gtt tta gaa aat tat aat tgg gaa gag aaa acg       2523
Leu Leu Thr Tyr Ala Val Leu Glu Asn Tyr Asn Trp Glu Glu Lys Thr
                305                 310                 315 gcg act ttc gct cat gcg act atg ctt aat gag ctt ttt act gat tat       2571
```

```
                 Ala Thr Phe Ala His Ala Thr Met Leu Asn Glu Leu Phe Thr Asp Tyr
                         320                 325                 330 act aat tat cgt tat gaa gtt aaa gga cta aaa ttg ccc gcc gtt aaa              2619
Thr Asn Tyr Arg Tyr Glu Val Lys Gly Leu Lys Leu Pro Ala Val Lys
        335                 340                 345 aag tta aaa agt ccg ttg gtg gag ttt aca gct gat tta tta act gtt             2667
Lys Leu Lys Ser Pro Leu Val Glu Phe Thr Ala Asp Leu Leu Thr Val
        350                 355                 360 acg cct att gac gaa aac gga aaa gca ctt agc gaa aaa agt att acg             2715
Thr Pro Ile Asp Glu Asn Gly Lys Ala Leu Ser Glu Lys Ser Ile Thr
365                 370                 375                 380 gtt aaa aat ttt aaa aat ggt gat tta gga ata agg ttg ttg gat cct             2763
Val Lys Asn Phe Lys Asn Gly Asp Leu Gly Ile Arg Leu Leu Asp Pro
                385                 390                 395 aat agc tat tat tat ttc ctt gaa ggc caa gat acg ggt ttt tat ggt             2811
Asn Ser Tyr Tyr Tyr Phe Leu Glu Gly Gln Asp Thr Gly Phe Tyr Gly
                400                 405                 410 cct gct ttt tat att gaa cga aaa aac ggt ggc ggc gct aaa aat aac             2859
Pro Ala Phe Tyr Ile Glu Arg Lys Asn Gly Gly Gly Ala Lys Asn Asn
                415                 420                 425 tcg tcg gga gca gga aat agc aaa gat tgg ggc ggg aac ggg cat gga             2907
Ser Ser Gly Ala Gly Asn Ser Lys Asp Trp Gly Gly Asn Gly His Gly
                430                 435                 440 aat cac cga aat aat gcc tcc gac ctg aat aaa ccg gac gga aat aat             2955
Asn His Arg Asn Asn Ala Ser Asp Leu Asn Lys Pro Asp Gly Asn Asn
445                 450                 455                 460 ggg aat aac caa aat aac gga agc aat caa gat aat cat agc gat gtg             3003
Gly Asn Asn Gln Asn Asn Gly Ser Asn Gln Asp Asn His Ser Asp Val
                465                 470                 475 aat gcg cca aat aac ccg gga cgt aac tat gat att tac gat cct tta             3051
Asn Ala Pro Asn Asn Pro Gly Arg Asn Tyr Asp Ile Tyr Asp Pro Leu
                480                 485                 490 gct tta gat tta gat gga gat ggg ctt gaa acc gtg tcg atg aac ggg             3099
Ala Leu Asp Leu Asp Gly Asp Gly Leu Glu Thr Val Ser Met Asn Gly
                495                 500                 505 cga caa ggc gcg tta ttc gat cat gaa gga aaa ggt att cgt acc gca             3147
Arg Gln Gly Ala Leu Phe Asp His Glu Gly Lys Gly Ile Arg Thr Ala
        510                 515                 520 acg ggc tgg ctc gct gcg gat gac ggt ttt tta gtg tta gat cgt aac             3195
Thr Gly Trp Leu Ala Ala Asp Asp Gly Phe Leu Val Leu Asp Arg Asn
525                 530                 535                 540 caa gac ggc att att aat gat ata agc gag tta ttt agt aat aaa aat             3243
Gln Asp Gly Ile Ile Asn Asp Ile Ser Glu Leu Phe Ser Asn Lys Asn
                545                 550                 555 caa ctt tcc gac ggc agt att tct gca cac ggt ttt gcg aca tta gcc             3291
Gln Leu Ser Asp Gly Ser Ile Ser Ala His Gly Phe Ala Thr Leu Ala
                560                 565                 570 gat ttg gat aca aac caa gat cag cgt atc gac caa aat gat aag ctg             3339
Asp Leu Asp Thr Asn Gln Asp Gln Arg Ile Asp Gln Asn Asp Lys Leu
                575                 580                 585 ttt tct aaa ctc caa att tgg cgg gat tta aat caa aac ggt ttt agt             3387
Phe Ser Lys Leu Gln Ile Trp Arg Asp Leu Asn Gln Asn Gly Phe Ser
        590                 595                 600 gaa gcg aat gag ctg ttt agc tta gaa agt ttg aat att aaa tct tta             3435
Glu Ala Asn Glu Leu Phe Ser Leu Glu Ser Leu Asn Ile Lys Ser Leu
605                 610                 615                 620 cat acc gcc tat gaa gag cgt aat gat ttt cta gcg ggc aat aat atc             3483
His Thr Ala Tyr Glu Glu Arg Asn Asp Phe Leu Ala Gly Asn Asn Ile
                625                 630                 635
```

-continued

| | | |
|---|---|---|
| ctt gct cag ctt ggg aag tat gaa aaa acg gac ggt act ttt gca caa<br>Leu Ala Gln Leu Gly Lys Tyr Glu Lys Thr Asp Gly Thr Phe Ala Gln<br>640 645 650 | 3531 | |
| atg ggc gat tta aat ttc agt ttt aac ccg ttt tat agc cga ttt acc<br>Met Gly Asp Leu Asn Phe Ser Phe Asn Pro Phe Tyr Ser Arg Phe Thr<br>655 660 665 | 3579 | |
| gaa gcg tta aat tta acc gag caa caa cgt cgc aca att aat cta acc<br>Glu Ala Leu Asn Leu Thr Glu Gln Gln Arg Arg Thr Ile Asn Leu Thr<br>670 675 680 | 3627 | |
| ggc acc ggt cgg gtt cgg gat ttg cgt gaa gcc gcc gca ctt tct gag<br>Gly Thr Gly Arg Val Arg Asp Leu Arg Glu Ala Ala Ala Leu Ser Glu<br>685 690 695 700 | 3675 | |
| gag ttg gct gct tta tta caa cag tac act aag gcc tcc gat ttt cag<br>Glu Leu Ala Ala Leu Leu Gln Gln Tyr Thr Lys Ala Ser Asp Phe Gln<br>705 710 715 | 3723 | |
| gca caa cga gaa tta ttg cct gcc att tta gat aaa tgg gcg gca acg<br>Ala Gln Arg Glu Leu Leu Pro Ala Ile Leu Asp Lys Trp Ala Ala Thr<br>720 725 730 | 3771 | |
| gat tta cag tat caa cat tat gat aaa aca tta ctt aaa acg gta gaa<br>Asp Leu Gln Tyr Gln His Tyr Asp Lys Thr Leu Leu Lys Thr Val Glu<br>735 740 745 | 3819 | |
| agt acc gat agt agt gct tct gtc gtt aga gtc acg cct tct caa tta<br>Ser Thr Asp Ser Ser Ala Ser Val Val Arg Val Thr Pro Ser Gln Leu<br>750 755 760 | 3867 | |
| agt agt ata cgc aat gca aag cat gat cct acc gtt atg caa aac ttt<br>Ser Ser Ile Arg Asn Ala Lys His Asp Pro Thr Val Met Gln Asn Phe<br>765 770 775 780 | 3915 | |
| gaa cag agt aag gca aaa att gcg act tta aat tcg ctc tac ggg tta<br>Glu Gln Ser Lys Ala Lys Ile Ala Thr Leu Asn Ser Leu Tyr Gly Leu<br>785 790 795 | 3963 | |
| aat atc gat caa ctt tat tac acg acg gat aaa gac att cgc tat att<br>Asn Ile Asp Gln Leu Tyr Tyr Thr Thr Asp Lys Asp Ile Arg Tyr Ile<br>800 805 810 | 4011 | |
| act gat aaa gtg aat aat atg tat caa aca acc gta gaa ctt gcc tac<br>Thr Asp Lys Val Asn Asn Met Tyr Gln Thr Thr Val Glu Leu Ala Tyr<br>815 820 825 | 4059 | |
| cgt tct tta ctt tta caa acg cgt ttg aag aaa tat gtt tat agc gtt<br>Arg Ser Leu Leu Leu Gln Thr Arg Leu Lys Lys Tyr Val Tyr Ser Val<br>830 835 840 | 4107 | |
| aat gcg aaa caa ttc gaa ggg aaa tgg gta acc gat tat tct cgt act<br>Asn Ala Lys Gln Phe Glu Gly Lys Trp Val Thr Asp Tyr Ser Arg Thr<br>845 850 855 860 | 4155 | |
| gaa gcc tta ttt aac tct act ttt aaa caa tcg cct gaa aat gca tta<br>Glu Ala Leu Phe Asn Ser Thr Phe Lys Gln Ser Pro Glu Asn Ala Leu<br>865 870 875 | 4203 | |
| tat gat tta agc gaa tac ctt tct ttc ttt aac gat cct acg gaa tgg<br>Tyr Asp Leu Ser Glu Tyr Leu Ser Phe Phe Asn Asp Pro Thr Glu Trp<br>880 885 890 | 4251 | |
| aaa gaa ggg cta tta ctg tta agc cgt tat ata gat tat gct aaa gca<br>Lys Glu Gly Leu Leu Leu Leu Ser Arg Tyr Ile Asp Tyr Ala Lys Ala<br>895 900 905 | 4299 | |
| caa gga ttt tat gaa aac tgg gcg gct act tct aac tta act att gcc<br>Gln Gly Phe Tyr Glu Asn Trp Ala Ala Thr Ser Asn Leu Thr Ile Ala<br>910 915 920 | 4347 | |
| cgt tta aga gag gct gga gta att ttt gca gaa tcg acg gat tta aaa<br>Arg Leu Arg Glu Ala Gly Val Ile Phe Ala Glu Ser Thr Asp Leu Lys<br>925 930 935 940 | 4395 | |
| ggc gat gaa aaa aat aat att ttg tta ggt agc caa aaa gat aat aac<br>Gly Asp Glu Lys Asn Asn Ile Leu Leu Gly Ser Gln Lys Asp Asn Asn<br>945 950 955 | 4443 | |

```
tta tcg ggt agt gca ggt gat gat cta ctt atc ggc gga gag ggt aat    4491
Leu Ser Gly Ser Ala Gly Asp Asp Leu Leu Ile Gly Gly Glu Gly Asn
        960                 965                 970 gat acg tta aaa ggc agc tac ggt gca gac acc tat atc ttt agc aaa    4539
Asp Thr Leu Lys Gly Ser Tyr Gly Ala Asp Thr Tyr Ile Phe Ser Lys
    975                 980                 985 gga cac gga cag gat atc gtt tat gaa gat acc aat aat gat aac cgc    4587
Gly His Gly Gln Asp Ile Val Tyr Glu Asp Thr Asn Asn Asp Asn Arg
990                 995                 1000 gca aga gat atc gac acc tta aaa ttt acc gat gtg aat tat gcg gaa    4635
Ala Arg Asp Ile Asp Thr Leu Lys Phe Thr Asp Val Asn Tyr Ala Glu
1005                1010                1015                1020 gtg aag ttt cga cga gta gat aat gac tta atg tta ttc ggt tat cat    4683
Val Lys Phe Arg Arg Val Asp Asn Asp Leu Met Leu Phe Gly Tyr His
                1025                1030                1035 gat acg gat tcg gtc acg gta aaa tcc ttc tac agc cat gta gat tat    4731
Asp Thr Asp Ser Val Thr Val Lys Ser Phe Tyr Ser His Val Asp Tyr
            1040                1045                1050 caa ttt gac aaa ttg gag ttt gct gac cgc agt ata act cgc gat gaa    4779
Gln Phe Asp Lys Leu Glu Phe Ala Asp Arg Ser Ile Thr Arg Asp Glu
        1055                1060                1065 ctg att aaa gca ggg ctt cat cta tac ggc acc gat ggc aat gat gat    4827
Leu Ile Lys Ala Gly Leu His Leu Tyr Gly Thr Asp Gly Asn Asp Asp
1070                1075                1080 ata aag gat cat gcg gat tgg gac agc att ttg gaa ggc ggc aaa ggc    4875
Ile Lys Asp His Ala Asp Trp Asp Ser Ile Leu Glu Gly Gly Lys Gly
1085                1090                1095                1100 aac gat att cta aga ggt ggc tac ggt gcg gac acc tat atc ttt agc    4923
Asn Asp Ile Leu Arg Gly Gly Tyr Gly Ala Asp Thr Tyr Ile Phe Ser
                1105                1110                1115 aaa gga cac gga cag gat atc gtt tat gaa gat acc aat aat gat aac    4971
Lys Gly His Gly Gln Asp Ile Val Tyr Glu Asp Thr Asn Asn Asp Asn
            1120                1125                1130 cgc gca aga gat atc gac acc tta aaa ttt act gat gtg aat tat gcg    5019
Arg Ala Arg Asp Ile Asp Thr Leu Lys Phe Thr Asp Val Asn Tyr Ala
        1135                1140                1145 gaa gtg aaa ttc cga cga gta gat aat gac tta atg tta ttc ggt tat    5067
Glu Val Lys Phe Arg Arg Val Asp Asn Asp Leu Met Leu Phe Gly Tyr
1150                1155                1160 cat gat acg gat tcg gtc acg ata aaa tcc ttc tac aac cat gta gat    5115
His Asp Thr Asp Ser Val Thr Ile Lys Ser Phe Tyr Asn His Val Asp
1165                1170                1175                1180 tat caa ttt gac aaa ttg gaa ttt gct gac cgc agt ata act cgt gat    5163
Tyr Gln Phe Asp Lys Leu Glu Phe Ala Asp Arg Ser Ile Thr Arg Asp
                1185                1190                1195 gaa cta ggt aaa caa ggt atg gca tta ttt ggc act gac ggt gat gat    5211
Glu Leu Gly Lys Gln Gly Met Ala Leu Phe Gly Thr Asp Gly Asp Asp
            1200                1205                1210 aat atc aac gac tgg gga cgt aac tcg gtg att gat gcc ggt gcg ggt    5259
Asn Ile Asn Asp Trp Gly Arg Asn Ser Val Ile Asp Ala Gly Ala Gly
        1215                1220                1225 aat gat acg gtt aat ggc ggt aat ggc gat gac acc ctc atc ggc ggc    5307
Asn Asp Thr Val Asn Gly Gly Asn Gly Asp Asp Thr Leu Ile Gly Gly
1230                1235                1240 aaa ggt aat gat att cta aga ggt ggc tac ggt gcg gac acc tat atc    5355
Lys Gly Asn Asp Ile Leu Arg Gly Gly Tyr Gly Ala Asp Thr Tyr Ile
1245                1250                1255                1260 ttt agc aaa gga cac gga cag gat atc gtt tat gaa gat acc aat aat    5403
Phe Ser Lys Gly His Gly Gln Asp Ile Val Tyr Glu Asp Thr Asn Asn
```

-continued

```
                    1265                   1270                   1275
gat aac cgc gca aga gat atc gac acc tta aaa ttt acc gat gtg aat        5451
Asp Asn Arg Ala Arg Asp Ile Asp Thr Leu Lys Phe Thr Asp Val Asn
            1280                   1285                   1290 tat gcg gaa gtg aaa ttc cga cga gta gat aat gac tta atg tta ttc        5499
Tyr Ala Glu Val Lys Phe Arg Arg Val Asp Asn Asp Leu Met Leu Phe
        1295                   1300                   1305 ggt tat cat gat acg gat tcg gtc acg gta aaa tcc ttc tac agc cat        5547
Gly Tyr His Asp Thr Asp Ser Val Thr Val Lys Ser Phe Tyr Ser His
    1310                   1315                   1320 gta gat tat caa ttt gac aaa ttg gag ttt gct gac cgc agt ata act        5595
Val Asp Tyr Gln Phe Asp Lys Leu Glu Phe Ala Asp Arg Ser Ile Thr
1325                   1330                   1335                   1340 cgc gat gaa ctg att aaa gca ggg ctt cat cta tac ggc acc gat ggc        5643
Arg Asp Glu Leu Ile Lys Ala Gly Leu His Leu Tyr Gly Thr Asp Gly
                1345                   1350                   1355 aat gat gat ata aag gat cat gcg gat tgg gac agc att ttg gaa ggc        5691
Asn Asp Asp Ile Lys Asp His Ala Asp Trp Asp Ser Ile Leu Glu Gly
            1360                   1365                   1370 ggc aaa ggc aac gat att cta aga ggt ggc tac ggt gcg gac acc tat        5739
Gly Lys Gly Asn Asp Ile Leu Arg Gly Gly Tyr Gly Ala Asp Thr Tyr
        1375                   1380                   1385 atc ttt agc aaa gga cac gga cag gat atc gtt tat gaa gat acc aat        5787
Ile Phe Ser Lys Gly His Gly Gln Asp Ile Val Tyr Glu Asp Thr Asn
    1390                   1395                   1400 aat gat aac cga gca aga gat atc gac acc tta aaa ttt act gat gtg        5835
Asn Asp Asn Arg Ala Arg Asp Ile Asp Thr Leu Lys Phe Thr Asp Val
1405                   1410                   1415                   1420 aat tat gcg gaa gtg aaa ttc cga cga gta gat aat gac tta atg tta        5883
Asn Tyr Ala Glu Val Lys Phe Arg Arg Val Asp Asn Asp Leu Met Leu
                1425                   1430                   1435 ttc ggt tat cat gat acg gat tcg gtc acg ata aaa tcc ttc tac aac        5931
Phe Gly Tyr His Asp Thr Asp Ser Val Thr Ile Lys Ser Phe Tyr Asn
            1440                   1445                   1450 cat gta gat tat caa ttt gac aaa ttg gaa ttt gct gac cgc agt ata        5979
His Val Asp Tyr Gln Phe Asp Lys Leu Glu Phe Ala Asp Arg Ser Ile
        1455                   1460                   1465 act cgt gat gaa cta ggt aaa caa ggt atg gca tta ttt ggc act gac        6027
Thr Arg Asp Glu Leu Gly Lys Gln Gly Met Ala Leu Phe Gly Thr Asp
    1470                   1475                   1480 ggt gat gat aat atc aac gac tgg gga cgt aac tcg gtg att gat gcc        6075
Gly Asp Asp Asn Ile Asn Asp Trp Gly Arg Asn Ser Val Ile Asp Ala
1485                   1490                   1495                   1500 ggt gcg ggt aat gat acg gtt aat ggc ggt aat ggc gat gac acc ctc        6123
Gly Ala Gly Asn Asp Thr Val Asn Gly Gly Asn Gly Asp Asp Thr Leu
                1505                   1510                   1515 atc ggc ggc aaa ggt aat gat att cta aga ggt ggc tac ggt gcg gac        6171
Ile Gly Gly Lys Gly Asn Asp Ile Leu Arg Gly Gly Tyr Gly Ala Asp
            1520                   1525                   1530 acc tat atc ttt agc aaa gga cac gga cag gat atc gtt tat gaa gat        6219
Thr Tyr Ile Phe Ser Lys Gly His Gly Gln Asp Ile Val Tyr Glu Asp
        1535                   1540                   1545 acc aat aat gat aac cgc gca aga gat atc gac acc tta aaa ttt act        6267
Thr Asn Asn Asp Asn Arg Ala Arg Asp Ile Asp Thr Leu Lys Phe Thr
    1550                   1555                   1560 gat att aat tta tcc gaa ctt tgg ttt agc cga gaa aat aac gat ttg        6315
Asp Ile Asn Leu Ser Glu Leu Trp Phe Ser Arg Glu Asn Asn Asp Leu
1565                   1570                   1575                   1580 att att aaa tca tta tta agt gag gat aaa gtc acg gtt caa aat tgg        6363
```

-continued

```
Ile Ile Lys Ser Leu Leu Ser Glu Asp Lys Val Thr Val Gln Asn Trp
            1585                1590                1595 tat tca cac caa gat cat aaa ata gaa aat att cgt tta tcg aat gag      6411
Tyr Ser His Gln Asp His Lys Ile Glu Asn Ile Arg Leu Ser Asn Glu
            1600                1605                1610 caa acg ttg gtg agc act cag gtg gag aag atg gtt gag tcg atg gcc      6459
Gln Thr Leu Val Ser Thr Gln Val Glu Lys Met Val Glu Ser Met Ala
            1615                1620                1625 ggc ttt gct cag aag cac gga gga gag ata tct ctt gtg tcg ctt gaa      6507
Gly Phe Ala Gln Lys His Gly Gly Glu Ile Ser Leu Val Ser Leu Glu
            1630                1635                1640 gag gta aaa caa tat atc aat agc tta aca gct gct tta taa              6549
Glu Val Lys Gln Tyr Ile Asn Ser Leu Thr Ala Ala Leu
1645                1650                1655 catacgaaag aaatcggcac agttttttg aactgtgccg atttgatttt agtgtaagaa     6609
tatagcctga ttttaagaaa tttactcttg gctaataact atttcccatt ttataagtta   6669
ttgacggatg gttttatcaa atatgagatc aaatcttatt ttaaattcgc tttccattaa   6729
gcgatat                                                              6736

<210> SEQ ID NO 2
<211> LENGTH: 1657
<212> TYPE: PRT
<213> ORGANISM: Actinobacillus pleuropneumoniae

<400> SEQUENCE: 2

Met Ser Asp Asn Ala Phe Phe Val Ile Glu Glu Ser Gly Lys Arg Tyr
1               5                   10                  15

Ile Glu Asn Phe Gly Ile Glu Pro Leu Gly Lys Gln Glu Asp Phe Asp
            20                  25                  30

Phe Val Gly Gly Phe Trp Ser Asn Leu Val Asn Arg Gly Leu Glu Ser
        35                  40                  45

Ile Ile Asp Pro Ser Gly Ile Gly Gly Thr Val Asn Leu Asn Phe Thr
    50                  55                  60

Gly Glu Val Glu Thr Tyr Thr Leu Asp Glu Thr Arg Phe Lys Ala Glu
65                  70                  75                  80

Ala Ala Lys Lys Ser His Trp Ser Leu Val Asn Ala Ala Lys Val Tyr
                85                  90                  95

Gly Gly Leu Asp Gln Ile Ile Lys Lys Leu Trp Asp Ser Gly Ser Ile
            100                 105                 110

Lys His Leu Tyr Gln Asp Lys Asp Thr Gly Lys Leu Lys Pro Ile Ile
        115                 120                 125

Tyr Gly Thr Ala Gly Asn Asp Ser Lys Ile Glu Gly Thr Lys Ile Thr
    130                 135                 140

Arg Arg Ile Ala Gly Lys Glu Val Thr Leu Asp Ile Ala Asn Gln Lys
145                 150                 155                 160

Ile Glu Lys Gly Val Leu Glu Lys Leu Gly Leu Ser Val Ser Gly Ser
                165                 170                 175

Asp Ile Ile Lys Leu Leu Phe Gly Ala Leu Thr Pro Thr Leu Asn Arg
            180                 185                 190

Met Leu Leu Ser Gln Leu Ile Gln Ser Phe Ser Asp Ser Leu Ala Lys
        195                 200                 205

Leu Asp Asn Pro Leu Ala Pro Tyr Thr Lys Asn Gly Val Val Tyr Val
    210                 215                 220

Thr Gly Lys Gly Asn Asp Val Leu Lys Gly Thr Glu His Glu Asp Leu
225                 230                 235                 240
```

```
Phe Leu Gly Gly Glu Gly Asn Asp Thr Tyr Tyr Ala Arg Val Gly Asp
                245                 250                 255

Thr Ile Glu Asp Ala Asp Gly Lys Gly Lys Val Tyr Phe Val Arg Glu
            260                 265                 270

Lys Gly Val Pro Lys Ala Asp Pro Lys Arg Val Glu Phe Ser Glu Tyr
        275                 280                 285

Ile Thr Lys Glu Glu Ile Lys Glu Val Glu Lys Gly Leu Leu Thr Tyr
    290                 295                 300

Ala Val Leu Glu Asn Tyr Asn Trp Glu Glu Lys Thr Ala Thr Phe Ala
305                 310                 315                 320

His Ala Thr Met Leu Asn Glu Leu Phe Thr Asp Tyr Thr Asn Tyr Arg
                325                 330                 335

Tyr Glu Val Lys Gly Leu Lys Leu Pro Ala Val Lys Lys Leu Lys Ser
            340                 345                 350

Pro Leu Val Glu Phe Thr Ala Asp Leu Leu Thr Val Thr Pro Ile Asp
        355                 360                 365

Glu Asn Gly Lys Ala Leu Ser Glu Lys Ser Ile Thr Val Lys Asn Phe
    370                 375                 380

Lys Asn Gly Asp Leu Gly Ile Arg Leu Leu Asp Pro Asn Ser Tyr Tyr
385                 390                 395                 400

Tyr Phe Leu Glu Gly Gln Asp Thr Gly Phe Tyr Gly Pro Ala Phe Tyr
                405                 410                 415

Ile Glu Arg Lys Asn Gly Gly Ala Lys Asn Asn Ser Ser Gly Ala
            420                 425                 430

Gly Asn Ser Lys Asp Trp Gly Gly Asn Gly His Gly Asn His Arg Asn
        435                 440                 445

Asn Ala Ser Asp Leu Asn Lys Pro Asp Gly Asn Asn Gly Asn Asn Gln
    450                 455                 460

Asn Asn Gly Ser Asn Gln Asp Asn His Ser Asp Val Asn Ala Pro Asn
465                 470                 475                 480

Asn Pro Gly Arg Asn Tyr Asp Ile Tyr Asp Pro Leu Ala Leu Asp Leu
                485                 490                 495

Asp Gly Asp Gly Leu Glu Thr Val Ser Met Asn Gly Arg Gln Gly Ala
            500                 505                 510

Leu Phe Asp His Glu Gly Lys Gly Ile Arg Thr Ala Thr Gly Trp Leu
        515                 520                 525

Ala Ala Asp Asp Gly Phe Leu Val Leu Asp Arg Asn Gln Asp Gly Ile
    530                 535                 540

Ile Asn Asp Ile Ser Glu Leu Phe Ser Asn Lys Asn Gln Leu Ser Asp
545                 550                 555                 560

Gly Ser Ile Ser Ala His Gly Phe Ala Thr Leu Ala Asp Leu Asp Thr
                565                 570                 575

Asn Gln Asp Gln Arg Ile Asp Gln Asn Asp Lys Leu Phe Ser Lys Leu
            580                 585                 590

Gln Ile Trp Arg Asp Leu Asn Gln Asn Gly Phe Ser Glu Ala Asn Glu
        595                 600                 605

Leu Phe Ser Leu Glu Ser Leu Asn Ile Lys Ser Leu His Thr Ala Tyr
    610                 615                 620

Glu Glu Arg Asn Asp Phe Leu Ala Gly Asn Asn Ile Leu Ala Gln Leu
625                 630                 635                 640

Gly Lys Tyr Glu Lys Thr Asp Gly Thr Phe Ala Gln Met Gly Asp Leu
                645                 650                 655
```

-continued

```
Asn Phe Ser Phe Asn Pro Phe Tyr Ser Arg Phe Thr Glu Ala Leu Asn
            660                 665                 670

Leu Thr Glu Gln Gln Arg Arg Thr Ile Asn Leu Thr Gly Thr Gly Arg
        675                 680                 685

Val Arg Asp Leu Arg Glu Ala Ala Leu Ser Glu Leu Ala Ala
    690                 695                 700

Leu Leu Gln Gln Tyr Thr Lys Ala Ser Asp Phe Gln Ala Gln Arg Glu
705                 710                 715                 720

Leu Leu Pro Ala Ile Leu Asp Lys Trp Ala Thr Asp Leu Gln Tyr
                725                 730                 735

Gln His Tyr Asp Lys Thr Leu Leu Lys Thr Val Glu Ser Thr Asp Ser
            740                 745                 750

Ser Ala Ser Val Val Arg Val Thr Pro Ser Gln Leu Ser Ser Ile Arg
        755                 760                 765

Asn Ala Lys His Asp Pro Thr Val Met Gln Asn Phe Glu Gln Ser Lys
    770                 775                 780

Ala Lys Ile Ala Thr Leu Asn Ser Leu Tyr Gly Leu Asn Ile Asp Gln
785                 790                 795                 800

Leu Tyr Tyr Thr Thr Asp Lys Asp Ile Arg Tyr Ile Thr Asp Lys Val
                805                 810                 815

Asn Asn Met Tyr Gln Thr Thr Val Glu Leu Ala Tyr Arg Ser Leu Leu
            820                 825                 830

Leu Gln Thr Arg Leu Lys Lys Tyr Val Tyr Ser Val Asn Ala Lys Gln
        835                 840                 845

Phe Glu Gly Lys Trp Val Thr Asp Tyr Ser Arg Thr Glu Ala Leu Phe
    850                 855                 860

Asn Ser Thr Phe Lys Gln Ser Pro Glu Asn Ala Leu Tyr Asp Leu Ser
865                 870                 875                 880

Glu Tyr Leu Ser Phe Phe Asn Asp Pro Thr Glu Trp Lys Glu Gly Leu
                885                 890                 895

Leu Leu Leu Ser Arg Tyr Ile Asp Tyr Ala Lys Ala Gln Gly Phe Tyr
            900                 905                 910

Glu Asn Trp Ala Ala Thr Ser Asn Leu Thr Ile Ala Arg Leu Arg Glu
        915                 920                 925

Ala Gly Val Ile Phe Ala Glu Ser Thr Asp Leu Lys Gly Asp Glu Lys
    930                 935                 940

Asn Asn Ile Leu Leu Gly Ser Gln Lys Asp Asn Asn Leu Ser Gly Ser
945                 950                 955                 960

Ala Gly Asp Asp Leu Leu Ile Gly Gly Glu Gly Asn Asp Thr Leu Lys
                965                 970                 975

Gly Ser Tyr Gly Ala Asp Thr Tyr Ile Phe Ser Lys Gly His Gly Gln
            980                 985                 990

Asp Ile Val Tyr Glu Asp Thr Asn Asn Asp Asn Arg Ala Arg Asp Ile
        995                 1000                1005

Asp Thr Leu Lys Phe Thr Asp Val Asn Tyr Ala Glu Val Lys Phe Arg
    1010                1015                1020

Arg Val Asp Asn Asp Leu Met Leu Phe Gly Tyr His Asp Thr Asp Ser
1025                1030                1035                1040

Val Thr Val Lys Ser Phe Tyr Ser His Val Asp Tyr Gln Phe Asp Lys
                1045                1050                1055

Leu Glu Phe Ala Asp Arg Ser Ile Thr Arg Asp Glu Leu Ile Lys Ala
            1060                1065                1070

Gly Leu His Leu Tyr Gly Thr Asp Gly Asn Asp Asp Ile Lys Asp His
```

```
                    1075                1080                1085
Ala Asp Trp Asp Ser Ile Leu Glu Gly Gly Lys Gly Asn Asp Ile Leu
            1090                1095                1100
Arg Gly Gly Tyr Gly Ala Asp Thr Tyr Ile Phe Ser Lys Gly His Gly
1105                1110                1115                1120
Gln Asp Ile Val Tyr Glu Asp Thr Asn Asn Asp Asn Arg Ala Arg Asp
            1125                1130                1135
Ile Asp Thr Leu Lys Phe Thr Asp Val Asn Tyr Ala Glu Val Lys Phe
            1140                1145                1150
Arg Arg Val Asp Asn Asp Leu Met Leu Phe Gly Tyr His Asp Thr Asp
            1155                1160                1165
Ser Val Thr Ile Lys Ser Phe Tyr Asn His Val Asp Tyr Gln Phe Asp
            1170                1175                1180
Lys Leu Glu Phe Ala Asp Arg Ser Ile Thr Arg Asp Glu Leu Gly Lys
1185                1190                1195                1200
Gln Gly Met Ala Leu Phe Gly Thr Asp Gly Asp Asp Asn Ile Asn Asp
            1205                1210                1215
Trp Gly Arg Asn Ser Val Ile Asp Ala Gly Ala Gly Asn Asp Thr Val
            1220                1225                1230
Asn Gly Gly Asn Gly Asp Asp Thr Leu Ile Gly Gly Lys Gly Asn Asp
            1235                1240                1245
Ile Leu Arg Gly Gly Tyr Gly Ala Asp Thr Tyr Ile Phe Ser Lys Gly
            1250                1255                1260
His Gly Gln Asp Ile Val Tyr Glu Asp Thr Asn Asn Asp Asn Arg Ala
1265                1270                1275                1280
Arg Asp Ile Asp Thr Leu Lys Phe Thr Asp Val Asn Tyr Ala Glu Val
            1285                1290                1295
Lys Phe Arg Arg Val Asp Asn Asp Leu Met Leu Phe Gly Tyr His Asp
            1300                1305                1310
Thr Asp Ser Val Thr Val Lys Ser Phe Tyr Ser His Val Asp Tyr Gln
            1315                1320                1325
Phe Asp Lys Leu Glu Phe Ala Asp Arg Ser Ile Thr Arg Asp Glu Leu
            1330                1335                1340
Ile Lys Ala Gly Leu His Leu Tyr Gly Thr Asp Gly Asn Asp Asp Ile
1345                1350                1355                1360
Lys Asp His Ala Asp Trp Asp Ser Ile Leu Glu Gly Lys Gly Asn
            1365                1370                1375
Asp Ile Leu Arg Gly Gly Tyr Gly Ala Asp Thr Tyr Ile Phe Ser Lys
            1380                1385                1390
Gly His Gly Gln Asp Ile Val Tyr Glu Asp Thr Asn Asn Asp Asn Arg
            1395                1400                1405
Ala Arg Asp Ile Asp Thr Leu Lys Phe Thr Asp Val Asn Tyr Ala Glu
            1410                1415                1420
Val Lys Phe Arg Arg Val Asp Asn Asp Leu Met Leu Phe Gly Tyr His
1425                1430                1435                1440
Asp Thr Asp Ser Val Thr Ile Lys Ser Phe Tyr Asn His Val Asp Tyr
            1445                1450                1455
Gln Phe Asp Lys Leu Glu Phe Ala Asp Arg Ser Ile Thr Arg Asp Glu
            1460                1465                1470
Leu Gly Lys Gln Gly Met Ala Leu Phe Gly Thr Asp Gly Asp Asp Asn
            1475                1480                1485
Ile Asn Asp Trp Gly Arg Asn Ser Val Ile Asp Ala Gly Ala Gly Asn
            1490                1495                1500
```

```
Asp Thr Val Asn Gly Gly Asn Gly Asp Asp Thr Leu Ile Gly Gly Lys
1505                1510                1515                1520
Gly Asn Asp Ile Leu Arg Gly Gly Tyr Gly Ala Asp Thr Tyr Ile Phe
            1525                1530                1535
Ser Lys Gly His Gly Gln Asp Ile Val Tyr Glu Asp Thr Asn Asn Asp
        1540                1545                1550
Asn Arg Ala Arg Asp Ile Asp Thr Leu Lys Phe Thr Asp Ile Asn Leu
    1555                1560                1565
Ser Glu Leu Trp Phe Ser Arg Glu Asn Asn Asp Leu Ile Ile Lys Ser
1570                1575                1580
Leu Leu Ser Glu Asp Lys Val Thr Val Gln Asn Trp Tyr Ser His Gln
1585                1590                1595                1600
Asp His Lys Ile Glu Asn Ile Arg Leu Ser Asn Glu Gln Thr Leu Val
            1605                1610                1615
Ser Thr Gln Val Glu Lys Met Val Glu Ser Met Ala Gly Phe Ala Gln
        1620                1625                1630
Lys His Gly Gly Glu Ile Ser Leu Val Ser Leu Glu Glu Val Lys Gln
    1635                1640                1645
Tyr Ile Asn Ser Leu Thr Ala Ala Leu
1650                1655

<210> SEQ ID NO 3
<211> LENGTH: 7004
<212> TYPE: DNA
<213> ORGANISM: Actinobacillus pleuropneumoniae
<220> FEATURE:
<221> NAME/KEY: CDS
<222> LOCATION: 1566..5714

<400> SEQUENCE: 3
atcgatatgc cgccgggtac gggcgatatc caacttactc tttcgcaaca aattccggtt      60
accggtgcgg tagtggtaac tactccgcaa gatattgcgt tattagatgc ggtgaaaggt     120
atttcaatgt tccaaaaagt gtcggtaccg gtcttaggta tcattgaaaa tatgagcgtg     180
catatctgcc aaaattgcgg tcaccacgaa gatattttcg gcaccggcgg tgcggagaaa     240
gtggcgaaga aatacggtac taaagtatta ggacaaatgc cgttgcatat tcgcttacgt     300
caagatttgg atgccggcac accgaccgtc gttgcggcac cggaacacga caccagcaga     360
gcctatattg aattagcggc aaaagtcgct tcggaattat actggcaagg ttcggttatc     420
ccgtctgaaa ttatgattcg tgaagtaaaa taagcctaca taaccacgga ataccagata     480
acacagaagg aaaacaagcg gtagaatttg cagaaaaagt tgcaaattct accgcttttt     540
tattagtacg attcgctgtt ggactgccat ttgatttggt ttgtcaggat attatgttat     600
tgtaatgaaa tgttagtgaa ttatttttat taatttgaaa ggagacaaaa tgaaaataaa     660
aaaacgttac attgcgctgc tagctttagg cagtgttatt ggctatgcct ggtatcaaaa     720
ttatcaatgg gaacagttga tgttaagtgg ctattgtgaa aaggacggaa gctattgtga     780
tgataggcat acgaagcagg aactgattga tagggcaatt aactatgtgc tggaaaatca     840
aattcaacag acatatgaag gtgatgacct tgtggatata aacaatatt caacaataga     900 ggaatttaaa aaactaaatc cgaattgttg taagtagat tcttggccgg atgatgctgt     960
tcgtgaggat gctgatttac agcgagaggg caaagcgtat aaatacgtaa agtcaaata    1020 tttaagaacc tatttagcga atagagaacc tgaacaatgg gaaaattaca tagtatttga    1080
taattgcagt ggaattaaag aaagacacca actgtattaa aaatagatta gatggagaca    1140
```

-continued

```
acacgatgac aaaactaact atccaagatg tgactaattt atatttatat aagcaaagaa    1200
ctttacctac ggataggtta gatgattcgc ttattagcaa acaggaaaaa ggggaaaata    1260
ttgataaaaa ggaatttatg gcggggccgg gacgttttgt gacggccgat aattttagtg    1320
ttgtaaaaga cttttttact gcaaaggatt cattaataaa cctaagcttg cagactcgta    1380
tattagcgaa tttaaagccg ggcaaatatt ccaaagcgca gatattagaa atgttgggct    1440
atacgaaaaa tggagaaaag gtagatggca tgtttaccgg tgaagtccag acattaggct    1500
tttatgacga tggcaaaggg gatttactcg aacgcgccta tatctgaaat accacaggat    1560 ttaaa atg agc gac aat gcc ttt ttt gtt ata gaa gaa tca ggc aaa       1607
      Met Ser Asp Asn Ala Phe Phe Val Ile Glu Glu Ser Gly Lys
        1               5                  10 cgc tat att gaa aac ttt ggt att gaa cct ctt ggt aag caa gaa gat     1655
Arg Tyr Ile Glu Asn Phe Gly Ile Glu Pro Leu Gly Lys Gln Glu Asp
 15              20              25              30 ttt gat ttt gtc ggc ggc ttt tgg tct aac tta gtg aat cgt ggt ttg     1703
Phe Asp Phe Val Gly Gly Phe Trp Ser Asn Leu Val Asn Arg Gly Leu
             35              40              45 gaa agt att atc gac cca tcc ggt atc ggt gga acg gta aac ctt aac     1751
Glu Ser Ile Ile Asp Pro Ser Gly Ile Gly Gly Thr Val Asn Leu Asn
         50              55              60 ttt acc ggc gag gtg gaa acc tac acg tta gac gaa aca agg ttt aaa     1799
Phe Thr Gly Glu Val Glu Thr Tyr Thr Leu Asp Glu Thr Arg Phe Lys
     65              70              75 gcg gaa gcg gcg aag aaa agc cat tgg agt tta gtg aat gcg gcg aaa     1847
Ala Glu Ala Ala Lys Lys Ser His Trp Ser Leu Val Asn Ala Ala Lys
 80              85              90 gta tac ggc ggt tta gac caa att att aaa aaa cta tgg gac agt ggc     1895
Val Tyr Gly Gly Leu Asp Gln Ile Ile Lys Lys Leu Trp Asp Ser Gly
 95              100             105             110 tca att aag cat tta tat caa gat aaa gat acg ggc aaa tta aaa ccg     1943
Ser Ile Lys His Leu Tyr Gln Asp Lys Asp Thr Gly Lys Leu Lys Pro
             115             120             125 att att tac ggc acg gcc ggc aac gac agt aag att gaa ggc act aaa     1991
Ile Ile Tyr Gly Thr Ala Gly Asn Asp Ser Lys Ile Glu Gly Thr Lys
         130             135             140 atc acc cgt agg att gcg ggt aaa gaa gtt acg ctt gat att gcc aat     2039
Ile Thr Arg Arg Ile Ala Gly Lys Glu Val Thr Leu Asp Ile Ala Asn
     145             150             155 cag aaa att gaa aaa ggc gtg tta gag aaa ttg ggg ctg tct gtt agt     2087
Gln Lys Ile Glu Lys Gly Val Leu Glu Lys Leu Gly Leu Ser Val Ser
 160             165             170 ggt tcg gat atc att aaa ttg ttg ttt gga gca ttg act cca act tta     2135
Gly Ser Asp Ile Ile Lys Leu Leu Phe Gly Ala Leu Thr Pro Thr Leu
175             180             185             190 aat aga atg ttg cta tca caa ctt atc cag tct ttt tcc gat agc ttg     2183
Asn Arg Met Leu Leu Ser Gln Leu Ile Gln Ser Phe Ser Asp Ser Leu
             195             200             205 gct aaa ctt gat aat ccc tta gcc cct tac act aaa aat ggc gtg gtt     2231
Ala Lys Leu Asp Asn Pro Leu Ala Pro Tyr Thr Lys Asn Gly Val Val
         210             215             220 tat gtc acc ggc aaa ggg aat gat gtg ctt aaa gga act gaa cat gag     2279
Tyr Val Thr Gly Lys Gly Asn Asp Val Leu Lys Gly Thr Glu His Glu
     225             230             235 gat ttg ttt ctc ggt ggt gag ggg aat gat act tat tat gcg aga gta    2327
Asp Leu Phe Leu Gly Gly Glu Gly Asn Asp Thr Tyr Tyr Ala Arg Val
 240             245             250
```

-continued

| | | |
|---|---|---|
| ggc gat aca att gaa gac gcc gac ggc aaa ggt aaa gtc tat ttt gtg<br>Gly Asp Thr Ile Glu Asp Ala Asp Gly Lys Gly Lys Val Tyr Phe Val<br>255                         260                    265                270 | 2375 |
| aga gaa aaa ggg gta cct aag gcg gat cct aag cgg gta gag ttt agc<br>Arg Glu Lys Gly Val Pro Lys Ala Asp Pro Lys Arg Val Glu Phe Ser<br>                    275                    280                  285 | 2423 |
| gag tac ata acg aaa gaa gaa ata aaa gag gtt gaa aag ggg tta tta<br>Glu Tyr Ile Thr Lys Glu Glu Ile Lys Glu Val Glu Lys Gly Leu Leu<br>            290                    295                  300 | 2471 |
| act tac gca gtt tta gaa aat tat aat tgg gaa gag aaa acg gcg act<br>Thr Tyr Ala Val Leu Glu Asn Tyr Asn Trp Glu Glu Lys Thr Ala Thr<br>305                         310                    315 | 2519 |
| ttc gct cat gcg act atg ctt aat gag ctt ttt act gat tat act aat<br>Phe Ala His Ala Thr Met Leu Asn Glu Leu Phe Thr Asp Tyr Thr Asn<br>            320                    325                  330 | 2567 |
| tat cgt tat gaa gtt aaa gga cta aaa ttg ccc gcc gtt aaa aag tta<br>Tyr Arg Tyr Glu Val Lys Gly Leu Lys Leu Pro Ala Val Lys Lys Leu<br>335                         340                    345              350 | 2615 |
| aaa agt ccg ttg gtg gag ttt aca gct gat tta tta act gtt acg cct<br>Lys Ser Pro Leu Val Glu Phe Thr Ala Asp Leu Leu Thr Val Thr Pro<br>                    355                    360                  365 | 2663 |
| att gac gaa aac gga aaa gca ctt agc gaa aaa agt att acg gtt aaa<br>Ile Asp Glu Asn Gly Lys Ala Leu Ser Glu Lys Ser Ile Thr Val Lys<br>            370                    375                  380 | 2711 |
| aat ttt aaa aat ggt gat tta gga ata agg ttg ttg gat cct aat agc<br>Asn Phe Lys Asn Gly Asp Leu Gly Ile Arg Leu Leu Asp Pro Asn Ser<br>                    385                    390                  395 | 2759 |
| tat tat tat ttc ctt gaa ggc caa gat acg ggt ttt tat ggt cct gct<br>Tyr Tyr Tyr Phe Leu Glu Gly Gln Asp Thr Gly Phe Tyr Gly Pro Ala<br>400                         405                    410 | 2807 |
| ttt tat att gaa cga aaa aac ggt gga ggc tct aaa aat aac tcg tcg<br>Phe Tyr Ile Glu Arg Lys Asn Gly Gly Gly Ser Lys Asn Asn Ser Ser<br>415                         420                    425              430 | 2855 |
| gga gca gga aat agc aaa gat tgg ggc ggg aac ggg cat gga aat cac<br>Gly Ala Gly Asn Ser Lys Asp Trp Gly Gly Asn Gly His Gly Asn His<br>                    435                    440                  445 | 2903 |
| cga aat aat gcc tcc gac ctg aat aaa ccg gac gga aat aat ggg aat<br>Arg Asn Asn Ala Ser Asp Leu Asn Lys Pro Asp Gly Asn Asn Gly Asn<br>            450                    455                  460 | 2951 |
| aac caa aat aac gga agc aat caa gat aat cat agc gat gtg aat gcg<br>Asn Gln Asn Asn Gly Ser Asn Gln Asp Asn His Ser Asp Val Asn Ala<br>                    465                    470                  475 | 2999 |
| cca aat aac ccg gga cgt aac tat gat att tac gat cct tta gct tta<br>Pro Asn Asn Pro Gly Arg Asn Tyr Asp Ile Tyr Asp Pro Leu Ala Leu<br>480                         485                    490 | 3047 |
| gat tta gat gga gat ggg ctt gaa acc gtg tcg atg aac ggg cga caa<br>Asp Leu Asp Gly Asp Gly Leu Glu Thr Val Ser Met Asn Gly Arg Gln<br>495                         500                    505              510 | 3095 |
| ggc gcg tta ttc gat cat gaa gga aaa ggt att cgt acc gca acg ggc<br>Gly Ala Leu Phe Asp His Glu Gly Lys Gly Ile Arg Thr Ala Thr Gly<br>                    515                    520                  525 | 3143 |
| tgg ctc gct gcg gat gac ggt ttt tta gtg tta gat cgt aac caa gac<br>Trp Leu Ala Ala Asp Asp Gly Phe Leu Val Leu Asp Arg Asn Gln Asp<br>                    530                    535                  540 | 3191 |
| ggc att att aat gat ata agc gag tta ttt agt aat aaa aat caa ctt<br>Gly Ile Ile Asn Asp Ile Ser Glu Leu Phe Ser Asn Lys Asn Gln Leu<br>                    545                    550                  555 | 3239 |
| tcc gac ggg agt att tct gca cac ggt ttt gcg aca tta gcc gat ttg<br>Ser Asp Gly Ser Ile Ser Ala His Gly Phe Ala Thr Leu Ala Asp Leu<br>560                         565                    570 | 3287 |

-continued

| | |
|---|---|
| gat aca aac caa gat cag cgt atc gac caa aat gat aag ctg ttt tct<br>Asp Thr Asn Gln Asp Gln Arg Ile Asp Gln Asn Asp Lys Leu Phe Ser<br>575                    580                    585                    590 | 3335 |
| aaa ctc caa att tgg cgg gat tta aat caa aac ggt ttt agt gaa gcg<br>Lys Leu Gln Ile Trp Arg Asp Leu Asn Gln Asn Gly Phe Ser Glu Ala<br>                  595                    600                    605 | 3383 |
| aat gag ctg ttt agc tta gaa agt ttg aat att aaa tct tta cat acc<br>Asn Glu Leu Phe Ser Leu Glu Ser Leu Asn Ile Lys Ser Leu His Thr<br>            610                    615                    620 | 3431 |
| gcc tat gaa gag cgt aat gat ttt cta gcg ggc aat aat atc ctt gct<br>Ala Tyr Glu Glu Arg Asn Asp Phe Leu Ala Gly Asn Asn Ile Leu Ala<br>625                    630                    635 | 3479 |
| cag ctt ggg aag tat gaa aaa acg gac ggt act ttt gga caa atg ggc<br>Gln Leu Gly Lys Tyr Glu Lys Thr Asp Gly Thr Phe Gly Gln Met Gly<br>          640                    645                    650 | 3527 |
| gat tta aat ttc agt ttt aac ccg ttt tat agc cga ttt acc gaa gcg<br>Asp Leu Asn Phe Ser Phe Asn Pro Phe Tyr Ser Arg Phe Thr Glu Ala<br>655                    660                    665                    670 | 3575 |
| tta aat tta acc gag caa caa cgt cgc aca att aat cta acc ggc acc<br>Leu Asn Leu Thr Glu Gln Gln Arg Arg Thr Ile Asn Leu Thr Gly Thr<br>                  675                    680                    685 | 3623 |
| ggt cgg gtt cgg gat ttg cgt gaa gcc gcc gca ctt tct gag gag ttg<br>Gly Arg Val Arg Asp Leu Arg Glu Ala Ala Ala Leu Ser Glu Glu Leu<br>690                    695                    700 | 3671 |
| gct gct tta tta caa cag tac act aag ggc tcc gat ttt cag gca caa<br>Ala Ala Leu Leu Gln Gln Tyr Thr Lys Gly Ser Asp Phe Gln Ala Gln<br>            705                    710                    715 | 3719 |
| cga gaa tta ttg cct gcc att tta gat aaa tgg gcg gca acg gat tta<br>Arg Glu Leu Leu Pro Ala Ile Leu Asp Lys Trp Ala Ala Thr Asp Leu<br>720                    725                    730 | 3767 |
| cag tat caa cat tat gat aaa aca tta ctt aaa acg gta gaa agt acc<br>Gln Tyr Gln His Tyr Asp Lys Thr Leu Leu Lys Thr Val Glu Ser Thr<br>735                    740                    745                    750 | 3815 |
| gat agt agt gct tct gtc gtt aga gtc acg cct tct caa tta agt agt<br>Asp Ser Ser Ala Ser Val Val Arg Val Thr Pro Ser Gln Leu Ser Ser<br>                  755                    760                    765 | 3863 |
| ata cgc aat gta aag cat gat cct acc gtt atg caa aac tgt gaa caa<br>Ile Arg Asn Val Lys His Asp Pro Thr Val Met Gln Asn Cys Glu Gln<br>770                    775                    780 | 3911 |
| agt aag gca aaa att gcg act tta aat tcg ctc tac ggg tta aat att<br>Ser Lys Ala Lys Ile Ala Thr Leu Asn Ser Leu Tyr Gly Leu Asn Ile<br>          785                    790                    795 | 3959 |
| gat caa ctt tat tat acg acg gat aaa gac att cgt tat att act gac<br>Asp Gln Leu Tyr Tyr Thr Thr Asp Lys Asp Ile Arg Tyr Ile Thr Asp<br>800                    805                    810 | 4007 |
| aaa gtg aat aat atg tat caa aca acc gga gaa ctc ggc tat cgt tct<br>Lys Val Asn Asn Met Tyr Gln Thr Thr Gly Glu Leu Gly Tyr Arg Ser<br>815                    820                    825                    830 | 4055 |
| tta ctt tta caa acg cgt gtg aag aaa tat gtt tat agc gtt aat gcg<br>Leu Leu Leu Gln Thr Arg Val Lys Lys Tyr Val Tyr Ser Val Asn Ala<br>                  835                    840                    845 | 4103 |
| aaa caa ttc gaa ggg aaa tgg gta gcc gat tat tct cgt act gaa gcc<br>Lys Gln Phe Glu Gly Lys Trp Val Ala Asp Tyr Ser Arg Thr Glu Ala<br>            850                    855                    860 | 4151 |
| tta ttt aac tct act tat aaa caa tcg ccc gaa aat gta tta tat gat<br>Leu Phe Asn Ser Thr Tyr Lys Gln Ser Pro Glu Asn Val Leu Tyr Asp<br>865                    870                    875 | 4199 |
| tta cgc gaa tac ctt tct ttc tat aac gac cct acg gaa tgg aaa gaa<br>Leu Arg Glu Tyr Leu Ser Phe Tyr Asn Asp Pro Thr Glu Trp Lys Glu | 4247 |

-continued

|  |  |  |
|---|---|---|
| 880 | 885 | 890 |

| ggg cta tta ctg tta agc cgt tat ata gat tat gct aaa gca caa gga<br>Gly Leu Leu Leu Leu Ser Arg Tyr Ile Asp Tyr Ala Lys Ala Gln Gly<br>895                                     900                                     905                            910 | 4295 |

| ttt tat gaa aac tgg gcg gct act tct aac tta act att gcc cgt tta<br>Phe Tyr Glu Asn Trp Ala Ala Thr Ser Asn Leu Thr Ile Ala Arg Leu<br>915                           920                           925 | 4343 |

| aga gag gct gga gta att tgt gca gaa tcg acg gat tta aaa ggc gat<br>Arg Glu Ala Gly Val Ile Cys Ala Glu Ser Thr Asp Leu Lys Gly Asp<br>930                           935                           940 | 4391 |

| gaa aaa aat aat att gtg tta ggt agc caa aaa gat aat aac tta tcg<br>Glu Lys Asn Asn Ile Val Leu Gly Ser Gln Lys Asp Asn Asn Leu Ser<br>945                           950                           955 | 4439 |

| ggt agt gca ggt gat gat cta ctt atc ggc gga gag ggt aat gat acg<br>Gly Ser Ala Gly Asp Asp Leu Leu Ile Gly Gly Glu Gly Asn Asp Thr<br>960                           965                           970 | 4487 |

| tta aaa ggc agc tac ggt gca gac acc tat atc ttt agc aaa ggg cat<br>Leu Lys Gly Ser Tyr Gly Ala Asp Thr Tyr Ile Phe Ser Lys Gly His<br>975                           980                           985                           990 | 4535 |

| gga caa gat gta att tat gaa tat tcc gac agt gca aac tct aaa aaa<br>Gly Gln Asp Val Ile Tyr Glu Tyr Ser Asp Ser Ala Asn Ser Lys Lys<br>                         995                           1000                         1005 | 4583 |

| gat att gat acc tta aaa ttt acc gat gtg aat tat gcg gaa gtg aag<br>Asp Ile Asp Thr Leu Lys Phe Thr Asp Val Asn Tyr Ala Glu Val Lys<br>                 1010                         1015                         1020 | 4631 |

| ttt cga cga gta gat aat gac tta atg tta ttc ggt tat cat gat acg<br>Phe Arg Arg Val Asp Asn Asp Leu Met Leu Phe Gly Tyr His Asp Thr<br>             1025                       1030                        1035 | 4679 |

| gat tcg gtc acg gta aaa tcc ttc tac agc cat gta gat tat caa ttt<br>Asp Ser Val Thr Val Lys Ser Phe Tyr Ser His Val Asp Tyr Gln Phe<br>1040                       1045                        1050 | 4727 |

| gac aaa ttg gag ttt gct gac cgc agt ata act cgc gat gaa ctg att<br>Asp Lys Leu Glu Phe Ala Asp Arg Ser Ile Thr Arg Asp Glu Leu Ile<br>1055                       1060                        1065                        1070 | 4775 |

| aaa gca ggg ctt cat cta tac ggc acc gat ggc aat gat gat ata aag<br>Lys Ala Gly Leu His Leu Tyr Gly Thr Asp Gly Asn Asp Asp Ile Lys<br>                 1075                         1080                         1085 | 4823 |

| gat cat gcg gat tgg gac agc att gtg gaa ggc ggc aaa ggc aac gat<br>Asp His Ala Asp Trp Asp Ser Ile Val Glu Gly Gly Lys Gly Asn Asp<br>             1090                        1095                         1100 | 4871 |

| att cta aga ggt ggc tac ggt gcg gac acc tat atc ttt agc aaa gga<br>Ile Leu Arg Gly Gly Tyr Gly Ala Asp Thr Tyr Ile Phe Ser Lys Gly<br>                 1105                         1110                        1115 | 4919 |

| cac gga cag gat atc gtt tat gaa gat acc aat aat gat aac cga gca<br>His Gly Gln Asp Ile Val Tyr Glu Asp Thr Asn Asn Asp Asn Arg Ala<br>             1120                        1125                         1130 | 4967 |

| aga gat atc gac acc tta aca ttt act gat gtg aat tat gcg gaa gtg<br>Arg Asp Ile Asp Thr Leu Thr Phe Thr Asp Val Asn Tyr Ala Glu Val<br>1135                       1140                        1145                        1150 | 5015 |

| aaa ttc cga cga gta gat aat gac tta atg tta ttc ggt tat cat gat<br>Lys Phe Arg Arg Val Asp Asn Asp Leu Met Leu Phe Gly Tyr His Asp<br>                 1155                         1160                        1165 | 5063 |

| acg gat tcg gtc acg ata aaa tcc ttc tac aac cat gta gat tat caa<br>Thr Asp Ser Val Thr Ile Lys Ser Phe Tyr Asn His Val Asp Tyr Gln<br>             1170                        1175                         1180 | 5111 |

| tgt gac aaa ttg gac ttt gct gac cgc agt ata act cgt gat gaa cta<br>Cys Asp Lys Leu Asp Phe Ala Asp Arg Ser Ile Thr Arg Asp Glu Leu<br>             1185                        1190                        1195 | 5159 |

| ggt aaa caa ggt atg gca tta ttt ggc act gac ggc gat gat aat atc | 5207 |

```
                                                         -continued

Gly Lys Gln Gly Met Ala Leu Phe Gly Thr Asp Gly Asp Asn Ile
    1200                1205                1210 aac gac tgg gga cgt aac tcg gtg att gat gcc ggt gcg ggt aat gat    5255
Asn Asp Trp Gly Arg Asn Ser Val Ile Asp Ala Gly Ala Gly Asn Asp
1215            1220                1225                1230 acg gtt aat ggc ggt aat ggc gat gac acc ctc atc ggc ggc aaa ggt    5303
Thr Val Asn Gly Gly Asn Gly Asp Asp Thr Leu Ile Gly Gly Lys Gly
                1235                1240                1245 aat gat att cta aga ggt ggc tac ggt gcg gac acc tat atc ttt agc    5351
Asn Asp Ile Leu Arg Gly Gly Tyr Gly Ala Asp Thr Tyr Ile Phe Ser
            1250                1255                1260 aaa gga cac gga cag gat atc gtt tat gaa gat acc aat aat gat aac    5399
Lys Gly His Gly Gln Asp Ile Val Tyr Glu Asp Thr Asn Asn Asp Asn
        1265                1270                1275 cgc gca aga gat atc gac acc tta aaa ttt act gat att aat tta tcc    5447
Arg Ala Arg Asp Ile Asp Thr Leu Lys Phe Thr Asp Ile Asn Leu Ser
    1280                1285                1290 gaa ctt tgg ttt agc cga gaa aat aac gat ttg att att aaa tca tta    5495
Glu Leu Trp Phe Ser Arg Glu Asn Asn Asp Leu Ile Ile Lys Ser Leu
1295                1300                1305                1310 tta agt gag gat aaa gtc acg gtt caa aat tgg tat tca cac caa gat    5543
Leu Ser Glu Asp Lys Val Thr Val Gln Asn Trp Tyr Ser His Gln Asp
                1315                1320                1325 cat aaa ata gaa aat att cgt tta tcg aat gag caa atg ttg gtg agc    5591
His Lys Ile Glu Asn Ile Arg Leu Ser Asn Glu Gln Met Leu Val Ser
            1330                1335                1340 act cag gtg gag aag atg gtt gag tcg atg gcc ggc ttt gct cag aag    5639
Thr Gln Val Glu Lys Met Val Glu Ser Met Ala Gly Phe Ala Gln Lys
        1345                1350                1355 cac gga gga gag ata tct ctt ctg tcg cct gaa gag gta aaa caa tat    5687
His Gly Gly Glu Ile Ser Leu Leu Ser Pro Glu Glu Val Lys Gln Tyr
    1360                1365                1370 atc aat agc tta aca gct gct tta taa catacgaaag aaatcggcac           5734
Ile Asn Ser Leu Thr Ala Ala Leu
1375                1380 agttttgtg aactgtgccg atttgatttt agtgtaagaa tatagcctga ttttaagaaa    5794
tttactcttg gctaataact atttcccatt ttataagtta ttgacggatg gttttatcaa   5854
atatgagatc aaatcttatt ttaaattcgc tttccattaa gcgatattga tcttttaagt   5914
ttggggccgc atgagtttgg aaccgatacc actcattgtg ggaatcaata cacaatacgc   5974
tgtaatcgga ctcttgcagt tcataataat gctttctctc cgttaattct tcttgcgtat   6034
atggcgagag attaaagctg aatggctggt tcgcactaac aaacaggttc tccgatttca   6094
gatattcaca accgtaatgg ctaccggttt cctgcggttt tacataattg gtatgatttt   6154
gtttagctgt tatacggtag atgcctaatt gtggtaaatt gcgtgtgtca atatagcttt   6214
cttgttctcc gtaaccgaaa tactcaatgg cgttttctgt tttagctaag aagaaacgta   6274
agccgaagcg gggtaaatac ggtaattcga tcgggcgaat agcgttaatt tcaaccgaaa   6334
gttgtccgtc attgaagata cgataacgaa tatccagtgt taaatgcgaa ccgcgagaaa   6394
ttgacacaat tgcagatttt actgaaaatt cgaccgcttg ttcgctttgc tgccactgaa   6454
tttcatacgc tctggtatag gctttatcgt agccggcatt ttggcacgcc tcacgaatga   6514
ggcgatcatt gtcggttggc gcacgccaaa tattaaaatc taacgattgt tggataatcg   6574
ctttaccggc ttttcaata cgggtgaaaa tcccttttctg tttatctaat tgataactaa   6634
attgaccgtt gtgtacgtta atgtggaagc gatcttcttg tacttcaaat gcactgttct   6694
```

-continued

```
caattgtgaa ttgtggtaat actaatttat tttcgctaaa taaattgagc tgctcgaagc      6754
caagtgaatg tgcttcgtct aataattcga ccgcggtatt taagcgataa tttaaattca      6814
gtagccataa atgcccgtta ttttttggta actcaatcgg taatactacg ctgccgtgcg      6874
gttggcaaga aacggataaa ttcccaccgc ttgtcaccac gccgttttcg acaaattcgt      6934
aatcaatcgt taaataatcg gcaagatcag tgaaatccaa gtagttgtgg atcacaattt      6994
ggttatcgat                                                             7004
```

<210> SEQ ID NO 4
<211> LENGTH: 1382
<212> TYPE: PRT
<213> ORGANISM: Actinobacillus pleuropneumoniae

<400> SEQUENCE: 4

```
Met Ser Asp Asn Ala Phe Phe Val Ile Glu Glu Ser Gly Lys Arg Tyr
  1               5                  10                  15

Ile Glu Asn Phe Gly Ile Glu Pro Leu Gly Lys Gln Glu Asp Phe Asp
                 20                  25                  30

Phe Val Gly Gly Phe Trp Ser Asn Leu Val Asn Arg Gly Leu Glu Ser
             35                  40                  45

Ile Ile Asp Pro Ser Gly Ile Gly Gly Thr Val Asn Leu Asn Phe Thr
         50                  55                  60

Gly Glu Val Glu Thr Tyr Thr Leu Asp Glu Thr Arg Phe Lys Ala Glu
 65                  70                  75                  80

Ala Ala Lys Lys Ser His Trp Ser Leu Val Asn Ala Lys Val Tyr
                 85                  90                  95

Gly Gly Leu Asp Gln Ile Ile Lys Lys Leu Trp Asp Ser Gly Ser Ile
            100                 105                 110

Lys His Leu Tyr Gln Asp Lys Asp Thr Gly Lys Leu Lys Pro Ile Ile
        115                 120                 125

Tyr Gly Thr Ala Gly Asn Asp Ser Lys Ile Glu Gly Thr Lys Ile Thr
    130                 135                 140

Arg Arg Ile Ala Gly Lys Glu Val Thr Leu Asp Ile Ala Asn Gln Lys
145                 150                 155                 160

Ile Glu Lys Gly Val Leu Glu Lys Leu Gly Leu Ser Val Ser Gly Ser
                165                 170                 175

Asp Ile Ile Lys Leu Leu Phe Gly Ala Leu Thr Pro Thr Leu Asn Arg
            180                 185                 190

Met Leu Leu Ser Gln Leu Ile Gln Ser Phe Ser Asp Ser Leu Ala Lys
        195                 200                 205

Leu Asp Asn Pro Leu Ala Pro Tyr Thr Lys Asn Gly Val Val Tyr Val
    210                 215                 220

Thr Gly Lys Gly Asn Asp Val Leu Lys Gly Thr Glu His Glu Asp Leu
225                 230                 235                 240

Phe Leu Gly Gly Glu Gly Asn Asp Thr Tyr Tyr Ala Arg Val Gly Asp
                245                 250                 255

Thr Ile Glu Asp Ala Asp Gly Lys Gly Lys Val Tyr Phe Val Arg Glu
            260                 265                 270

Lys Gly Val Pro Lys Ala Asp Pro Lys Arg Val Glu Phe Ser Glu Tyr
        275                 280                 285

Ile Thr Lys Glu Glu Ile Lys Glu Val Glu Lys Gly Leu Leu Thr Tyr
    290                 295                 300

Ala Val Leu Glu Asn Tyr Asn Trp Glu Glu Lys Thr Ala Thr Phe Ala
305                 310                 315                 320
```

```
His Ala Thr Met Leu Asn Glu Leu Phe Thr Asp Tyr Thr Asn Tyr Arg
            325                 330                 335
Tyr Glu Val Lys Gly Leu Lys Leu Pro Ala Val Lys Leu Lys Ser
        340                 345                 350
Pro Leu Val Glu Phe Thr Ala Asp Leu Leu Thr Val Thr Pro Ile Asp
            355                 360                 365
Glu Asn Gly Lys Ala Leu Ser Glu Lys Ser Ile Thr Val Lys Asn Phe
    370                 375                 380
Lys Asn Gly Asp Leu Gly Ile Arg Leu Leu Asp Pro Asn Ser Tyr Tyr
385                 390                 395                 400
Tyr Phe Leu Glu Gly Gln Asp Thr Gly Phe Tyr Gly Pro Ala Phe Tyr
            405                 410                 415
Ile Glu Arg Lys Asn Gly Gly Ser Lys Asn Ser Ser Gly Ala
            420                 425                 430
Gly Asn Ser Lys Asp Trp Gly Gly Asn Gly His Gly Asn His Arg Asn
            435                 440                 445
Asn Ala Ser Asp Leu Asn Lys Pro Asp Gly Asn Asn Gly Asn Asn Gln
    450                 455                 460
Asn Asn Gly Ser Asn Gln Asp Asn His Ser Asp Val Asn Ala Pro Asn
465                 470                 475                 480
Asn Pro Gly Arg Asn Tyr Asp Ile Tyr Asp Pro Leu Ala Leu Asp Leu
            485                 490                 495
Asp Gly Asp Gly Leu Glu Thr Val Ser Met Asn Gly Arg Gln Gly Ala
            500                 505                 510
Leu Phe Asp His Glu Gly Lys Gly Ile Arg Thr Ala Thr Gly Trp Leu
            515                 520                 525
Ala Ala Asp Asp Gly Phe Leu Val Leu Asp Arg Asn Gln Asp Gly Ile
            530                 535                 540
Ile Asn Asp Ile Ser Glu Leu Phe Ser Asn Lys Asn Gln Leu Ser Asp
545                 550                 555                 560
Gly Ser Ile Ser Ala His Gly Phe Ala Thr Leu Ala Asp Leu Asp Thr
            565                 570                 575
Asn Gln Asp Gln Arg Ile Asp Gln Asn Asp Lys Leu Phe Ser Lys Leu
            580                 585                 590
Gln Ile Trp Arg Asp Leu Asn Gln Asn Gly Phe Ser Glu Ala Asn Glu
            595                 600                 605
Leu Phe Ser Leu Glu Ser Leu Asn Ile Lys Ser Leu His Thr Ala Tyr
            610                 615                 620
Glu Glu Arg Asn Asp Phe Leu Ala Gly Asn Asn Ile Leu Ala Gln Leu
625                 630                 635                 640
Gly Lys Tyr Glu Lys Thr Asp Gly Thr Phe Gly Gln Met Gly Asp Leu
            645                 650                 655
Asn Phe Ser Phe Asn Pro Phe Tyr Ser Arg Phe Thr Glu Ala Leu Asn
            660                 665                 670
Leu Thr Glu Gln Gln Arg Arg Thr Ile Asn Leu Thr Gly Thr Gly Arg
            675                 680                 685
Val Arg Asp Leu Arg Glu Ala Ala Ala Leu Ser Glu Glu Leu Ala Ala
            690                 695                 700
Leu Leu Gln Gln Tyr Thr Lys Gly Ser Asp Phe Gln Ala Gln Arg Glu
705                 710                 715                 720
Leu Leu Pro Ala Ile Leu Asp Lys Trp Ala Ala Thr Asp Leu Gln Tyr
            725                 730                 735
```

-continued

```
Gln His Tyr Asp Lys Thr Leu Leu Lys Thr Val Glu Ser Thr Asp Ser
            740                 745                 750

Ser Ala Ser Val Val Arg Val Thr Pro Ser Gln Leu Ser Ser Ile Arg
            755                 760                 765

Asn Val Lys His Asp Pro Thr Val Met Gln Asn Cys Glu Gln Ser Lys
            770                 775                 780

Ala Lys Ile Ala Thr Leu Asn Ser Leu Tyr Gly Leu Asn Ile Asp Gln
785                 790                 795                 800

Leu Tyr Tyr Thr Thr Asp Lys Asp Ile Arg Tyr Ile Thr Asp Lys Val
                805                 810                 815

Asn Asn Met Tyr Gln Thr Thr Gly Glu Leu Gly Tyr Arg Ser Leu Leu
                820                 825                 830

Leu Gln Thr Arg Val Lys Lys Tyr Val Tyr Ser Val Asn Ala Lys Gln
                835                 840                 845

Phe Glu Gly Lys Trp Val Ala Asp Tyr Ser Arg Thr Glu Ala Leu Phe
            850                 855                 860

Asn Ser Thr Tyr Lys Gln Ser Pro Glu Asn Val Leu Tyr Asp Leu Arg
865                 870                 875                 880

Glu Tyr Leu Ser Phe Tyr Asn Asp Pro Thr Trp Lys Glu Gly Leu
                885                 890                 895

Leu Leu Leu Ser Arg Tyr Ile Asp Tyr Ala Lys Ala Gln Gly Phe Tyr
                900                 905                 910

Glu Asn Trp Ala Ala Thr Ser Asn Leu Thr Ile Ala Arg Leu Arg Glu
            915                 920                 925

Ala Gly Val Ile Cys Ala Glu Ser Thr Asp Leu Lys Gly Asp Glu Lys
            930                 935                 940

Asn Asn Ile Val Leu Gly Ser Gln Lys Asp Asn Asn Leu Ser Gly Ser
945                 950                 955                 960

Ala Gly Asp Asp Leu Leu Ile Gly Gly Glu Gly Asn Asp Thr Leu Lys
                965                 970                 975

Gly Ser Tyr Gly Ala Asp Thr Tyr Ile Phe Ser Lys Gly His Gly Gln
                980                 985                 990

Asp Val Ile Tyr Glu Tyr Ser Asp Ser Ala Asn Ser Lys Lys Asp Ile
                995                 1000                1005

Asp Thr Leu Lys Phe Thr Asp Val Asn Tyr Ala Glu Val Lys Phe Arg
    1010                1015                1020

Arg Val Asp Asn Asp Leu Met Leu Phe Gly Tyr His Asp Thr Asp Ser
1025                1030                1035                1040

Val Thr Val Lys Ser Phe Tyr Ser His Val Asp Tyr Gln Phe Asp Lys
                1045                1050                1055

Leu Glu Phe Ala Asp Arg Ser Ile Thr Arg Asp Glu Leu Ile Lys Ala
            1060                1065                1070

Gly Leu His Leu Tyr Gly Thr Asp Gly Asn Asp Asp Ile Lys Asp His
            1075                1080                1085

Ala Asp Trp Asp Ser Ile Val Glu Gly Gly Lys Gly Asn Asp Ile Leu
            1090                1095                1100

Arg Gly Gly Tyr Gly Ala Asp Thr Tyr Ile Phe Ser Lys Gly His Gly
1105                1110                1115                1120

Gln Asp Ile Val Tyr Glu Asp Thr Asn Asn Asp Asn Arg Ala Arg Asp
                1125                1130                1135

Ile Asp Thr Leu Thr Phe Thr Asp Val Asn Tyr Ala Glu Val Lys Phe
                1140                1145                1150

Arg Arg Val Asp Asn Asp Leu Met Leu Phe Gly Tyr His Asp Thr Asp
```

```
                1155                1160                1165
Ser Val Thr Ile Lys Ser Phe Tyr Asn His Val Asp Tyr Gln Cys Asp
    1170                1175                1180

Lys Leu Asp Phe Ala Asp Arg Ser Ile Thr Arg Asp Glu Leu Gly Lys
1185                1190                1195                1200

Gln Gly Met Ala Leu Phe Gly Thr Asp Gly Asp Asn Ile Asn Asp
                1205                1210                1215

Trp Gly Arg Asn Ser Val Ile Asp Ala Gly Ala Gly Asn Asp Thr Val
                1220                1225                1230

Asn Gly Gly Asn Gly Asp Asp Thr Leu Ile Gly Gly Lys Gly Asn Asp
            1235                1240                1245

Ile Leu Arg Gly Gly Tyr Gly Ala Asp Thr Tyr Ile Phe Ser Lys Gly
        1250                1255                1260

His Gly Gln Asp Ile Val Tyr Glu Asp Thr Asn Asn Asp Asn Arg Ala
1265                1270                1275                1280

Arg Asp Ile Asp Thr Leu Lys Phe Thr Asp Ile Asn Leu Ser Glu Leu
                1285                1290                1295

Trp Phe Ser Arg Glu Asn Asn Asp Leu Ile Ile Lys Ser Leu Leu Ser
            1300                1305                1310

Glu Asp Lys Val Thr Val Gln Asn Trp Tyr Ser His Gln Asp His Lys
        1315                1320                1325

Ile Glu Asn Ile Arg Leu Ser Asn Glu Gln Met Leu Val Ser Thr Gln
    1330                1335                1340

Val Glu Lys Met Val Glu Ser Met Ala Gly Phe Ala Gln Lys His Gly
1345                1350                1355                1360

Gly Glu Ile Ser Leu Leu Ser Pro Glu Glu Val Lys Gln Tyr Ile Asn
                1365                1370                1375

Ser Leu Thr Ala Ala Leu
            1380

<210> SEQ ID NO 5
<211> LENGTH: 6736
<212> TYPE: DNA
<213> ORGANISM: Actinobacillus pleuropneumoniae
<220> FEATURE:
<221> NAME/KEY: CDS
<222> LOCATION: 1..453
<220> FEATURE:
<221> NAME/KEY: CDS
<222> LOCATION: 1132..6549
<220> FEATURE:
<221> NAME/KEY: -10_signal
<222> LOCATION: 617..623
<220> FEATURE:
<221> NAME/KEY: -35_signal
<222> LOCATION: 594..599
<220> FEATURE:
<221> NAME/KEY: promoter
<222> LOCATION: 454..1131

<400> SEQUENCE: 5 atc gat atg ccg ccg ggt acg ggc gat atc caa ctt act ctt tcg caa    48
Ile Asp Met Pro Pro Gly Thr Gly Asp Ile Gln Leu Thr Leu Ser Gln
  1               5                  10                  15 caa att ccg gtt acc ggt gcg gtg gtg gta acc act ccg caa gat att    96
Gln Ile Pro Val Thr Gly Ala Val Val Val Thr Thr Pro Gln Asp Ile
                 20                  25                  30 gcg tta tta gat gcg gtg aaa ggt att tca atg ttc caa aaa gtg tcg   144
Ala Leu Leu Asp Ala Val Lys Gly Ile Ser Met Phe Gln Lys Val Ser
             35                  40                  45
```

-continued

| | |
|---|---|
| gta ccg gtc tta ggt atc att gaa aat atg agc gta cat atc tgc caa<br>Val Pro Val Leu Gly Ile Ile Glu Asn Met Ser Val His Ile Cys Gln<br>50              55                  60 | 192 |
| aat tgc ggt cac cac gaa gat att ttc ggc acc ggt gcg gag aaa<br>Asn Cys Gly His His Glu Asp Ile Phe Gly Thr Gly Gly Ala Glu Lys<br>65              70                  75                  80 | 240 |
| gtg gcg aag aaa tac ggt act aaa gta tta gga caa atg ccg ttg cat<br>Val Ala Lys Lys Tyr Gly Thr Lys Val Leu Gly Gln Met Pro Leu His<br>              85                  90                  95 | 288 |
| att cgc tta cgt caa gat ttg gat gcc ggc aca ccg acc gtc gtt gcg<br>Ile Arg Leu Arg Gln Asp Leu Asp Ala Gly Thr Pro Thr Val Val Ala<br>            100                 105                 110 | 336 |
| gca ccg gaa cac gaa acc agc cga gcc tat att gaa tta gcg gca aaa<br>Ala Pro Glu His Glu Thr Ser Arg Ala Tyr Ile Glu Leu Ala Ala Lys<br>            115                 120                 125 | 384 |
| gtc gct tcg gaa tta tac tgg caa ggt tcg gtt atc ccg tct gaa att<br>Val Ala Ser Glu Leu Tyr Trp Gln Gly Ser Val Ile Pro Ser Glu Ile<br>130                 135                 140 | 432 |
| atg att cgt gaa gta aaa taa gttttaataa ccacgaaaac acaaagaaca<br>Met Ile Arg Glu Val Lys<br>145                 150 | 483 |
| caagcggtag aatttgcaga aaaatttgca aatcctaccg cttttttatt agtacgattc | 543 |
| gctgttggac tgctatttga tttggtttgt caggatatta tgttattgta atgaaatgtt | 603 |
| agtgaattat ttttattaat ttgaaaggaa acaaaatgaa aataaaaaaa cgttacattg | 663 |
| cgctgttggt cttaggtgtc gttatcagct atgcctggta tcaaaattat caatgggaac | 723 |
| agctgatgtt aagcggttat tgtgaaaagg acggaagtta ttttgatgat aggcatacga | 783 |
| agcaagaact gattgatagg gcaattaact atatgctgga gcatcaatct aaaaaaacat | 843 |
| acgatgctta tactgatgaa cctttagaaa taaaaccata tttaacaata gaggaattta | 903 |
| aaaaactcaa tccaaattgt tgtgaaaatta cctcatggcc agcagatgca gttccacaag | 963 |
| attgggatgt tcgtgtggaa ggtaaggcat ataggtatgt aatcgtaaaa tatttaagaa | 1023 |
| ccttagcaaa tagagaacct gaacgatggg aaactagtat tgttttttgat aattgcggca | 1083 |
| atcctaaaag agcaagctac ttatattatt taaagagaga aatttatt atg aca aaa<br>                                                          Met Thr Lys<br>                                                           1 | 1140 |
| tta act atg caa gat gtg acc aat tta tat tta tat aaa acg aaa act<br>Leu Thr Met Gln Asp Val Thr Asn Leu Tyr Leu Tyr Lys Thr Lys Thr<br>        5                  10                  15 | 1188 |
| cta cct aaa gat aga ttg gat gat tca ctt att tct gaa ata gga aaa<br>Leu Pro Lys Asp Arg Leu Asp Asp Ser Leu Ile Ser Glu Ile Gly Lys<br>20                  25                  30                  35 | 1236 |
| gga gat gat gat att gat aga aaa gaa ttt atg gtg ggg ccg gga cgt<br>Gly Asp Asp Asp Ile Asp Arg Lys Glu Phe Met Val Gly Pro Gly Arg<br>                40                  45                  50 | 1284 |
| ttt gtg acc gct gat aac ttt agc gtt gta aga gat ttt ttt aat gct<br>Phe Val Thr Ala Asp Asn Phe Ser Val Val Arg Asp Phe Phe Asn Ala<br>            55                  60                  65 | 1332 |
| ggg aaa tca cgc att att gcg ccg caa gtc ccg cct att cgt tca cag<br>Gly Lys Ser Arg Ile Ile Ala Pro Gln Val Pro Pro Ile Arg Ser Gln<br>            70                  75                  80 | 1380 |
| cag gaa aaa atc ttg gtc ggt tta aaa ccg ggc aaa tat tcc aaa gcg<br>Gln Glu Lys Ile Leu Val Gly Leu Lys Pro Gly Lys Tyr Ser Lys Ala<br>        85                  90                  95 | 1428 |
| cag ata ttg gaa atg ctg ggt tat acg aaa ggc gga gaa gtg gta aat<br>Gln Ile Leu Glu Met Leu Gly Tyr Thr Lys Gly Gly Glu Val Val Asn<br>100                 105                 110                 115 | 1476 |

```
ggc atg ttt gcc ggt gaa gtc cag aca tta ggc ttt tat gac gat ggc      1524
Gly Met Phe Ala Gly Glu Val Gln Thr Leu Gly Phe Tyr Asp Asp Gly
        120                 125                 130 aaa ggg gat tta ctc gaa cgc gcc tat atc tgg aat acc aca gga ttt      1572
Lys Gly Asp Leu Leu Glu Arg Ala Tyr Ile Trp Asn Thr Thr Gly Phe
    135                 140                 145 aaa atg agc gac aat gcc ttt ttt gtt ata gaa gaa tca ggc aaa cgc      1620
Lys Met Ser Asp Asn Ala Phe Phe Val Ile Glu Glu Ser Gly Lys Arg
150                 155                 160 tat att gaa aac ttt ggt att gaa cct ctt ggt aag caa gaa gat ttt      1668
Tyr Ile Glu Asn Phe Gly Ile Glu Pro Leu Gly Lys Gln Glu Asp Phe
        165                 170                 175 gat ttt gtc ggc ggc ttt tgg tct aac tta gtg aat cgt ggt ttg gaa      1716
Asp Phe Val Gly Gly Phe Trp Ser Asn Leu Val Asn Arg Gly Leu Glu
180                 185                 190                 195 agt att atc gac cca tcc ggt atc ggt gga acg gta aac ctt aac ttt      1764
Ser Ile Ile Asp Pro Ser Gly Ile Gly Gly Thr Val Asn Leu Asn Phe
                200                 205                 210 acc ggc gag gtg gaa acc tac acg tta gac gaa aca agg ttt aaa gcg      1812
Thr Gly Glu Val Glu Thr Tyr Thr Leu Asp Glu Thr Arg Phe Lys Ala
        215                 220                 225 gaa gcg gcg aag aaa agc cat tgg agt tta gtg aat gcg gcg aaa gta      1860
Glu Ala Ala Lys Lys Ser His Trp Ser Leu Val Asn Ala Ala Lys Val
    230                 235                 240 tac ggc ggt tta gac caa att att aaa aaa cta tgg gac agt ggc tca      1908
Tyr Gly Gly Leu Asp Gln Ile Ile Lys Lys Leu Trp Asp Ser Gly Ser
245                 250                 255 att aag cat tta tat caa gat aaa gat acg ggc aaa tta aaa ccg att      1956
Ile Lys His Leu Tyr Gln Asp Lys Asp Thr Gly Lys Leu Lys Pro Ile
260                 265                 270                 275 att tac ggc acg gcc ggc aac gac agt aag att gaa ggc act aaa atc      2004
Ile Tyr Gly Thr Ala Gly Asn Asp Ser Lys Ile Glu Gly Thr Lys Ile
                280                 285                 290 acc cgt agg att gcg ggt aaa gaa gtt acg ctt gat att gcc aat cag      2052
Thr Arg Arg Ile Ala Gly Lys Glu Val Thr Leu Asp Ile Ala Asn Gln
        295                 300                 305 aaa att gaa aaa ggc gtg tta gag aaa ttg ggg ctg tct gtt agt ggt      2100
Lys Ile Glu Lys Gly Val Leu Glu Lys Leu Gly Leu Ser Val Ser Gly
    310                 315                 320 tcg gat atc att aaa ttg ttg ttt gga gca ttg act cca act tta aat      2148
Ser Asp Ile Ile Lys Leu Leu Phe Gly Ala Leu Thr Pro Thr Leu Asn
325                 330                 335 aga atg ttg cta tca caa ctt atc cag tct ttt tcc gat agc ttg gct      2196
Arg Met Leu Leu Ser Gln Leu Ile Gln Ser Phe Ser Asp Ser Leu Ala
340                 345                 350                 355 aaa ctt gat aat ccc tta gcc cct tac act aaa aat ggc gtg gtt tat      2244
Lys Leu Asp Asn Pro Leu Ala Pro Tyr Thr Lys Asn Gly Val Val Tyr
                360                 365                 370 gtc acc ggc aaa ggg aat gat gtg ctt aaa gga act gaa cat gag gat      2292
Val Thr Gly Lys Gly Asn Asp Val Leu Lys Gly Thr Glu His Glu Asp
        375                 380                 385 ttg ttt ctc ggt ggt gag ggg aat gat act tat tat gcg aga gta ggc      2340
Leu Phe Leu Gly Gly Glu Gly Asn Asp Thr Tyr Tyr Ala Arg Val Gly
    390                 395                 400 gat aca att gaa gac gcc gac ggc aaa ggt aaa gtc tat ttt gtg aga      2388
Asp Thr Ile Glu Asp Ala Asp Gly Lys Gly Lys Val Tyr Phe Val Arg
405                 410                 415 gaa aaa ggg gta cct aag gcg gat cct aag cgg gta gag ttt agc gag      2436
Glu Lys Gly Val Pro Lys Ala Asp Pro Lys Arg Val Glu Phe Ser Glu
```

-continued

| | | | | |
|---|---|---|---|---|
| 420 | 425 | 430 | 435 | |
| tac ata acg aaa gaa gaa ata aaa gag gtt gaa aag ggg tta tta act<br>Tyr Ile Thr Lys Glu Glu Ile Lys Glu Val Glu Lys Gly Leu Leu Thr<br>440 445 450 | | | | 2484 |
| tac gca gtt tta gaa aat tat aat tgg gaa gag aaa acg gcg act ttc<br>Tyr Ala Val Leu Glu Asn Tyr Asn Trp Glu Glu Lys Thr Ala Thr Phe<br>455 460 465 | | | | 2532 |
| gct cat gcg act atg ctt aat gag ctt ttt act gat tat act aat tat<br>Ala His Ala Thr Met Leu Asn Glu Leu Phe Thr Asp Tyr Thr Asn Tyr<br>470 475 480 | | | | 2580 |
| cgt tat gaa gtt aaa gga cta aaa ttg ccc gcc gtt aaa aag tta aaa<br>Arg Tyr Glu Val Lys Gly Leu Lys Leu Pro Ala Val Lys Lys Leu Lys<br>485 490 495 | | | | 2628 |
| agt ccg ttg gtg gag ttt aca gct gat tta tta act gtt acg cct att<br>Ser Pro Leu Val Glu Phe Thr Ala Asp Leu Leu Thr Val Thr Pro Ile<br>500 505 510 515 | | | | 2676 |
| gac gaa aac gga aaa gca ctt agc gaa aaa agt att acg gtt aaa aat<br>Asp Glu Asn Gly Lys Ala Leu Ser Glu Lys Ser Ile Thr Val Lys Asn<br>520 525 530 | | | | 2724 |
| ttt aaa aat ggt gat tta gga ata agg ttg ttg gat cct aat agc tat<br>Phe Lys Asn Gly Asp Leu Gly Ile Arg Leu Leu Asp Pro Asn Ser Tyr<br>535 540 545 | | | | 2772 |
| tat tat ttc ctt gaa ggc caa gat acg ggt ttt tat ggt cct gct ttt<br>Tyr Tyr Phe Leu Glu Gly Gln Asp Thr Gly Phe Tyr Gly Pro Ala Phe<br>550 555 560 | | | | 2820 |
| tat att gaa cga aaa aac ggt ggc ggc gct aaa aat aac tcg tcg gga<br>Tyr Ile Glu Arg Lys Asn Gly Gly Gly Ala Lys Asn Asn Ser Ser Gly<br>565 570 575 | | | | 2868 |
| gca gga aat agc aaa gat tgg ggc ggg aac ggg cat gga aat cac cga<br>Ala Gly Asn Ser Lys Asp Trp Gly Gly Asn Gly His Gly Asn His Arg<br>580 585 590 595 | | | | 2916 |
| aat aat gcc tcc gac ctg aat aaa ccg gac gga aat aat ggg aat aac<br>Asn Asn Ala Ser Asp Leu Asn Lys Pro Asp Gly Asn Asn Gly Asn Asn<br>600 605 610 | | | | 2964 |
| caa aat aac gga agc aat caa gat aat cat agc gat gtg aat gcg cca<br>Gln Asn Asn Gly Ser Asn Gln Asp Asn His Ser Asp Val Asn Ala Pro<br>615 620 625 | | | | 3012 |
| aat aac ccg gga cgt aac tat gat att tac gat cct tta gct tta gat<br>Asn Asn Pro Gly Arg Asn Tyr Asp Ile Tyr Asp Pro Leu Ala Leu Asp<br>630 635 640 | | | | 3060 |
| tta gat gga gat ggg ctt gaa acc gtg tcg atg aac ggg cga caa ggc<br>Leu Asp Gly Asp Gly Leu Glu Thr Val Ser Met Asn Gly Arg Gln Gly<br>645 650 655 | | | | 3108 |
| gcg tta ttc gat cat gaa gga aaa ggt att cgt acc gca acg ggc tgg<br>Ala Leu Phe Asp His Glu Gly Lys Gly Ile Arg Thr Ala Thr Gly Trp<br>660 665 670 675 | | | | 3156 |
| ctc gct gcg gat gac ggt ttt tta gtg tta gat cgt aac caa gac ggc<br>Leu Ala Ala Asp Asp Gly Phe Leu Val Leu Asp Arg Asn Gln Asp Gly<br>680 685 690 | | | | 3204 |
| att att aat gat ata agc gag tta ttt agt aat aaa aat caa ctt tcc<br>Ile Ile Asn Asp Ile Ser Glu Leu Phe Ser Asn Lys Asn Gln Leu Ser<br>695 700 705 | | | | 3252 |
| gac ggc agt att tct gca cac ggt ttt gcg aca tta gcc gat ttg gat<br>Asp Gly Ser Ile Ser Ala His Gly Phe Ala Thr Leu Ala Asp Leu Asp<br>710 715 720 | | | | 3300 |
| aca aac caa gat cag cgt atc gac caa aat gat aag ctg ttt tct aaa<br>Thr Asn Gln Asp Gln Arg Ile Asp Gln Asn Asp Lys Leu Phe Ser Lys<br>725 730 735 | | | | 3348 |
| ctc caa att tgg cgg gat tta aat caa aac ggt ttt agt gaa gcg aat | | | | 3396 |

```
                    -continued

Leu Gln Ile Trp Arg Asp Leu Asn Gln Asn Gly Phe Ser Glu Ala Asn
740             745                 750                 755 gag ctg ttt agc tta gaa agt ttg aat att aaa tct tta cat acc gcc      3444
Glu Leu Phe Ser Leu Glu Ser Leu Asn Ile Lys Ser Leu His Thr Ala
                    760                 765                 770 tat gaa gag cgt aat gat ttt cta gcg ggc aat aat atc ctt gct cag      3492
Tyr Glu Glu Arg Asn Asp Phe Leu Ala Gly Asn Asn Ile Leu Ala Gln
            775                 780                 785 ctt ggg aag tat gaa aaa acg gac ggt act ttt gca caa atg ggc gat      3540
Leu Gly Lys Tyr Glu Lys Thr Asp Gly Thr Phe Ala Gln Met Gly Asp
        790                 795                 800 tta aat ttc agt ttt aac ccg ttt tat agc cga ttt acc gaa gcg tta      3588
Leu Asn Phe Ser Phe Asn Pro Phe Tyr Ser Arg Phe Thr Glu Ala Leu
    805                 810                 815 aat tta acc gag caa caa cgt cgc aca att aat cta acc ggc acc ggt      3636
Asn Leu Thr Glu Gln Gln Arg Arg Thr Ile Asn Leu Thr Gly Thr Gly
820                 825                 830                 835 cgg gtt cgg gat ttg cgt gaa gcc gcc gca ctt tct gag gag ttg gct      3684
Arg Val Arg Asp Leu Arg Glu Ala Ala Ala Leu Ser Glu Glu Leu Ala
                    840                 845                 850 gct tta tta caa cag tac act aag gcc tcc gat ttt cag gca caa cga      3732
Ala Leu Leu Gln Gln Tyr Thr Lys Ala Ser Asp Phe Gln Ala Gln Arg
            855                 860                 865 gaa tta ttg cct gcc att tta gat aaa tgg gcg gca acg gat tta cag      3780
Glu Leu Leu Pro Ala Ile Leu Asp Lys Trp Ala Ala Thr Asp Leu Gln
        870                 875                 880 tat caa cat tat gat aaa aca tta ctt aaa acg gta gaa agt acc gat      3828
Tyr Gln His Tyr Asp Lys Thr Leu Leu Lys Thr Val Glu Ser Thr Asp
    885                 890                 895 agt agt gct tct gtc gtt aga gtc acg cct tct caa tta agt agt ata      3876
Ser Ser Ala Ser Val Val Arg Val Thr Pro Ser Gln Leu Ser Ser Ile
900                 905                 910                 915 cgc aat gca aag cat gat cct acc gtt atg caa aac ttt gaa cag agt      3924
Arg Asn Ala Lys His Asp Pro Thr Val Met Gln Asn Phe Glu Gln Ser
                    920                 925                 930 aag gca aaa att gcg act tta aat tcg ctc tac ggg tta aat atc gat      3972
Lys Ala Lys Ile Ala Thr Leu Asn Ser Leu Tyr Gly Leu Asn Ile Asp
            935                 940                 945 caa ctt tat tac acg acg gat aaa gac att cgc tat att act gat aaa      4020
Gln Leu Tyr Tyr Thr Thr Asp Lys Asp Ile Arg Tyr Ile Thr Asp Lys
        950                 955                 960 gtg aat aat atg tat caa aca acc gta gaa ctt gcc tac cgt tct tta      4068
Val Asn Asn Met Tyr Gln Thr Thr Val Glu Leu Ala Tyr Arg Ser Leu
    965                 970                 975 ctt tta caa acg cgt ttg aag aaa tat gtt tat agc gtt aat gcg aaa      4116
Leu Leu Gln Thr Arg Leu Lys Lys Tyr Val Tyr Ser Val Asn Ala Lys
980                 985                 990                 995 caa ttc gaa ggg aaa tgg gta acc gat tat tct cgt act gaa gcc tta      4164
Gln Phe Glu Gly Lys Trp Val Thr Asp Tyr Ser Arg Thr Glu Ala Leu
                    1000                1005                1010 ttt aac tct act ttt aaa caa tcg cct gaa aat gca tta tat gat tta      4212
Phe Asn Ser Thr Phe Lys Gln Ser Pro Glu Asn Ala Leu Tyr Asp Leu
            1015                1020                1025 agc gaa tac ctt tct ttc ttt aac gat cct acg gaa tgg aaa gaa ggg      4260
Ser Glu Tyr Leu Ser Phe Phe Asn Asp Pro Thr Glu Trp Lys Glu Gly
        1030                1035                1040 cta tta ctg tta agc cgt tat ata gat tat gct aaa gca caa gga ttt      4308
Leu Leu Leu Leu Ser Arg Tyr Ile Asp Tyr Ala Lys Ala Gln Gly Phe
    1045                1050                1055
```

-continued

| | |
|---|---|
| tat gaa aac tgg gcg gct act tct aac tta act att gcc cgt tta aga<br>Tyr Glu Asn Trp Ala Ala Thr Ser Asn Leu Thr Ile Ala Arg Leu Arg<br>1060                      1065                      1070                      1075 | 4356 |
| gag gct gga gta att ttt gca gaa tcg acg gat tta aaa ggc gat gaa<br>Glu Ala Gly Val Ile Phe Ala Glu Ser Thr Asp Leu Lys Gly Asp Glu<br>                    1080                      1085                      1090 | 4404 |
| aaa aat aat att ttg tta ggt agc caa aaa gat aat aac tta tcg ggt<br>Lys Asn Asn Ile Leu Leu Gly Ser Gln Lys Asp Asn Asn Leu Ser Gly<br>1095                      1100                      1105 | 4452 |
| agt gca ggt gat gat cta ctt atc ggc gga gag ggt aat gat acg tta<br>Ser Ala Gly Asp Asp Leu Leu Ile Gly Gly Glu Gly Asn Asp Thr Leu<br>                    1110                      1115                      1120 | 4500 |
| aaa ggc agc tac ggt gca gac acc tat atc ttt agc aaa gga cac gga<br>Lys Gly Ser Tyr Gly Ala Asp Thr Tyr Ile Phe Ser Lys Gly His Gly<br>1125                      1130                      1135 | 4548 |
| cag gat atc gtt tat gaa gat acc aat aat gat aac cgc gca aga gat<br>Gln Asp Ile Val Tyr Glu Asp Thr Asn Asn Asp Asn Arg Ala Arg Asp<br>1140                      1145                      1150                      1155 | 4596 |
| atc gac acc tta aaa ttt acc gat gtg aat tat gcg gaa gtg aag ttt<br>Ile Asp Thr Leu Lys Phe Thr Asp Val Asn Tyr Ala Glu Val Lys Phe<br>                    1160                      1165                      1170 | 4644 |
| cga cga gta gat aat gac tta atg tta ttc ggt tat cat gat acg gat<br>Arg Arg Val Asp Asn Asp Leu Met Leu Phe Gly Tyr His Asp Thr Asp<br>1175                      1180                      1185 | 4692 |
| tcg gtc acg gta aaa tcc ttc tac agc cat gta gat tat caa ttt gac<br>Ser Val Thr Val Lys Ser Phe Tyr Ser His Val Asp Tyr Gln Phe Asp<br>                    1190                      1195                      1200 | 4740 |
| aaa ttg gag ttt gct gac cgc agt ata act cgc gat gaa ctg att aaa<br>Lys Leu Glu Phe Ala Asp Arg Ser Ile Thr Arg Asp Glu Leu Ile Lys<br>1205                      1210                      1215 | 4788 |
| gca ggg ctt cat cta tac ggc acc gat ggc aat gat gat ata aag gat<br>Ala Gly Leu His Leu Tyr Gly Thr Asp Gly Asn Asp Asp Ile Lys Asp<br>1220                      1225                      1230                      1235 | 4836 |
| cat gcg gat tgg gac agc att ttg gaa ggc ggc aaa ggc aac gat att<br>His Ala Asp Trp Asp Ser Ile Leu Glu Gly Gly Lys Gly Asn Asp Ile<br>                    1240                      1245                      1250 | 4884 |
| cta aga ggt ggc tac ggt gcg gac acc tat atc ttt agc aaa gga cac<br>Leu Arg Gly Gly Tyr Gly Ala Asp Thr Tyr Ile Phe Ser Lys Gly His<br>1255                      1260                      1265 | 4932 |
| gga cag gat atc gtt tat gaa gat acc aat aat gat aac cgc gca aga<br>Gly Gln Asp Ile Val Tyr Glu Asp Thr Asn Asn Asp Asn Arg Ala Arg<br>                    1270                      1275                      1280 | 4980 |
| gat atc gac acc tta aaa ttt act gat gtg aat tat gcg gaa gtg aaa<br>Asp Ile Asp Thr Leu Lys Phe Thr Asp Val Asn Tyr Ala Glu Val Lys<br>1285                      1290                      1295 | 5028 |
| ttc cga cga gta gat aat gac tta atg tta ttc ggt tat cat gat acg<br>Phe Arg Arg Val Asp Asn Asp Leu Met Leu Phe Gly Tyr His Asp Thr<br>1300                      1305                      1310                      1315 | 5076 |
| gat tcg gtc acg ata aaa tcc ttc tac aac cat gta gat tat caa ttt<br>Asp Ser Val Thr Ile Lys Ser Phe Tyr Asn His Val Asp Tyr Gln Phe<br>                    1320                      1325                      1330 | 5124 |
| gac aaa ttg gaa ttt gct gac cgc agt ata act cgt gat gaa cta ggt<br>Asp Lys Leu Glu Phe Ala Asp Arg Ser Ile Thr Arg Asp Glu Leu Gly<br>1335                      1340                      1345 | 5172 |
| aaa caa ggt atg gca tta ttt ggc act gac ggt gat gat aat atc aac<br>Lys Gln Gly Met Ala Leu Phe Gly Thr Asp Gly Asp Asp Asn Ile Asn<br>                    1350                      1355                      1360 | 5220 |
| gac tgg gga cgt aac tcg gtg att gat gcc ggt gcg ggt aat gat acg<br>Asp Trp Gly Arg Asn Ser Val Ile Asp Ala Gly Ala Gly Asn Asp Thr<br>1365                      1370                      1375 | 5268 |

```
gtt aat ggc ggt aat ggc gat gac acc ctc atc ggc ggc aaa ggt aat        5316
Val Asn Gly Gly Asn Gly Asp Asp Thr Leu Ile Gly Gly Lys Gly Asn
1380                1385                1390                1395 gat att cta aga ggt ggc tac ggt gcg gac acc tat atc ttt agc aaa        5364
Asp Ile Leu Arg Gly Gly Tyr Gly Ala Asp Thr Tyr Ile Phe Ser Lys
            1400                1405                1410 gga cac gga cag gat atc gtt tat gaa gat acc aat aat gat aac cgc        5412
Gly His Gly Gln Asp Ile Val Tyr Glu Asp Thr Asn Asn Asp Asn Arg
        1415                1420                1425 gca aga gat atc gac acc tta aaa ttt acc gat gtg aat tat gcg gaa        5460
Ala Arg Asp Ile Asp Thr Leu Lys Phe Thr Asp Val Asn Tyr Ala Glu
    1430                1435                1440 gtg aaa ttc cga cga gta gat aat gac tta atg tta ttc ggt tat cat        5508
Val Lys Phe Arg Arg Val Asp Asn Asp Leu Met Leu Phe Gly Tyr His
1445                1450                1455 gat acg gat tcg gtc acg gta aaa tcc ttc tac agc cat gta gat tat        5556
Asp Thr Asp Ser Val Thr Val Lys Ser Phe Tyr Ser His Val Asp Tyr
1460                1465                1470                1475 caa ttt gac aaa ttg gag ttt gct gac cgc agt ata act cgc gat gaa        5604
Gln Phe Asp Lys Leu Glu Phe Ala Asp Arg Ser Ile Thr Arg Asp Glu
            1480                1485                1490 ctg att aaa gca ggg ctt cat cta tac ggc acc gat ggc aat gat gat        5652
Leu Ile Lys Ala Gly Leu His Leu Tyr Gly Thr Asp Gly Asn Asp Asp
        1495                1500                1505 ata aag gat cat gcg gat tgg gac agc att ttg gaa ggc ggc aaa ggc        5700
Ile Lys Asp His Ala Asp Trp Asp Ser Ile Leu Glu Gly Gly Lys Gly
    1510                1515                1520 aac gat att cta aga ggt ggc tac ggt gcg gac acc tat atc ttt agc        5748
Asn Asp Ile Leu Arg Gly Gly Tyr Gly Ala Asp Thr Tyr Ile Phe Ser
1525                1530                1535 aaa gga cac gga cag gat atc gtt tat gaa gat acc aat aat gat aac        5796
Lys Gly His Gly Gln Asp Ile Val Tyr Glu Asp Thr Asn Asn Asp Asn
1540                1545                1550                1555 cga gca aga gat atc gac acc tta aaa ttt act gat gtg aat tat gcg        5844
Arg Ala Arg Asp Ile Asp Thr Leu Lys Phe Thr Asp Val Asn Tyr Ala
            1560                1565                1570 gaa gtg aaa ttc cga cga gta gat aat gac tta atg tta ttc ggt tat        5892
Glu Val Lys Phe Arg Arg Val Asp Asn Asp Leu Met Leu Phe Gly Tyr
        1575                1580                1585 cat gat acg gat tcg gtc acg ata aaa tcc ttc tac aac cat gta gat        5940
His Asp Thr Asp Ser Val Thr Ile Lys Ser Phe Tyr Asn His Val Asp
    1590                1595                1600 tat caa ttt gac aaa ttg gaa ttt gct gac cgc agt ata act cgt gat        5988
Tyr Gln Phe Asp Lys Leu Glu Phe Ala Asp Arg Ser Ile Thr Arg Asp
1605                1610                1615 gaa cta ggt aaa caa ggt atg gca tta ttt ggc act gac ggt gat gat        6036
Glu Leu Gly Lys Gln Gly Met Ala Leu Phe Gly Thr Asp Gly Asp Asp
1620                1625                1630                1635 aat atc aac gac tgg gga cgt aac tcg gtg att gat gcc ggt gcg ggt        6084
Asn Ile Asn Asp Trp Gly Arg Asn Ser Val Ile Asp Ala Gly Ala Gly
            1640                1645                1650 aat gat acg gtt aat ggc ggt aat ggc gat gac acc ctc atc ggc ggc        6132
Asn Asp Thr Val Asn Gly Gly Asn Gly Asp Asp Thr Leu Ile Gly Gly
        1655                1660                1665 aaa ggt aat gat att cta aga ggt ggc tac ggt gcg gac acc tat atc        6180
Lys Gly Asn Asp Ile Leu Arg Gly Gly Tyr Gly Ala Asp Thr Tyr Ile
    1670                1675                1680 ttt agc aaa gga cac gga cag gat atc gtt tat gaa gat acc aat aat        6228
Phe Ser Lys Gly His Gly Gln Asp Ile Val Tyr Glu Asp Thr Asn Asn
```

```
                    1685              1690              1695
gat aac cgc gca aga gat atc gac acc tta aaa ttt act gat att aat      6276
Asp Asn Arg Ala Arg Asp Ile Asp Thr Leu Lys Phe Thr Asp Ile Asn
1700            1705              1710              1715 tta tcc gaa ctt tgg ttt agc cga gaa aat aac gat ttg att att aaa      6324
Leu Ser Glu Leu Trp Phe Ser Arg Glu Asn Asn Asp Leu Ile Ile Lys
                1720              1725              1730 tca tta tta agt gag gat aaa gtc acg gtt caa aat tgg tat tca cac      6372
Ser Leu Leu Ser Glu Asp Lys Val Thr Val Gln Asn Trp Tyr Ser His
            1735              1740              1745 caa gat cat aaa ata gaa aat att cgt tta tcg aat gag caa acg ttg      6420
Gln Asp His Lys Ile Glu Asn Ile Arg Leu Ser Asn Glu Gln Thr Leu
        1750              1755              1760 gtg agc act cag gtg gag aag atg gtt gag tcg atg gcc ggc ttt gct      6468
Val Ser Thr Gln Val Glu Lys Met Val Glu Ser Met Ala Gly Phe Ala
    1765              1770              1775 gag aag cac gga gga gag ata tct ctt gtg tcg ctt gaa gag gta aaa      6516
Gln Lys His Gly Gly Glu Ile Ser Leu Val Ser Leu Glu Glu Val Lys
1780              1785              1790              1795 caa tat atc aat agc tta aca gct gct tta taa catacgaaag aaatcggcac   6569
Gln Tyr Ile Asn Ser Leu Thr Ala Ala Leu
                1800              1805 agttttttg aactgtgccg atttgatttt agtgtaagaa tatagcctga ttttaagaaa    6629
tttactcttg gctaataact atttcccatt ttataagtta ttgacggatg gttttatcaa   6689
atatgagatc aaatcttatt ttaaattcgc tttccattaa gcgatat                 6736

<210> SEQ ID NO 6
<211> LENGTH: 150
<212> TYPE: PRT
<213> ORGANISM: Actinobacillus pleuropneumoniae

<400> SEQUENCE: 6

Ile Asp Met Pro Pro Gly Thr Gly Asp Ile Gln Leu Thr Leu Ser Gln
 1               5                  10                  15

Gln Ile Pro Val Thr Gly Ala Val Val Thr Thr Pro Gln Asp Ile
             20                  25                  30

Ala Leu Leu Asp Ala Val Lys Gly Ile Ser Met Phe Gln Lys Val Ser
         35                  40                  45

Val Pro Val Leu Gly Ile Ile Glu Asn Met Ser Val His Ile Cys Gln
     50                  55                  60

Asn Cys Gly His His Glu Asp Ile Phe Gly Thr Gly Ala Glu Lys
 65                  70                  75                  80

Val Ala Lys Lys Tyr Gly Thr Lys Val Leu Gly Gln Met Pro Leu His
                 85                  90                  95

Ile Arg Leu Arg Gln Asp Leu Asp Ala Gly Thr Pro Thr Val Val Ala
             100                 105                 110

Ala Pro Glu His Glu Thr Ser Arg Ala Tyr Ile Glu Leu Ala Ala Lys
         115                 120                 125

Val Ala Ser Glu Leu Tyr Trp Gln Gly Ser Val Ile Pro Ser Glu Ile
     130                 135                 140

Met Ile Arg Glu Val Lys
145                 150

<210> SEQ ID NO 7
<211> LENGTH: 1805
<212> TYPE: PRT
<213> ORGANISM: Actinobacillus pleuropneumoniae
```

<400> SEQUENCE: 7

```
Met Thr Lys Leu Thr Met Gln Asp Val Thr Asn Leu Tyr Leu Tyr Lys
  1               5                  10                  15
Thr Lys Thr Leu Pro Lys Asp Arg Leu Asp Asp Ser Leu Ile Ser Glu
             20                  25                  30
Ile Gly Lys Gly Asp Asp Ile Asp Arg Lys Glu Phe Met Val Gly
             35                  40                  45
Pro Gly Arg Phe Val Thr Ala Asp Asn Phe Ser Val Val Arg Asp Phe
 50                  55                  60
Phe Asn Ala Gly Lys Ser Arg Ile Ile Ala Pro Gln Val Pro Pro Ile
 65                  70                  75                  80
Arg Ser Gln Gln Glu Lys Ile Leu Val Gly Leu Lys Pro Gly Lys Tyr
                 85                  90                  95
Ser Lys Ala Gln Ile Leu Glu Met Leu Gly Tyr Thr Lys Gly Gly Glu
                100                 105                 110
Val Val Asn Gly Met Phe Ala Gly Glu Val Gln Thr Leu Gly Phe Tyr
             115                 120                 125
Asp Asp Gly Lys Gly Asp Leu Leu Glu Arg Ala Tyr Ile Trp Asn Thr
130                 135                 140
Thr Gly Phe Lys Met Ser Asp Asn Ala Phe Phe Val Ile Glu Glu Ser
145                 150                 155                 160
Gly Lys Arg Tyr Ile Glu Asn Phe Gly Ile Glu Pro Leu Gly Lys Gln
                165                 170                 175
Glu Asp Phe Asp Phe Val Gly Gly Phe Trp Ser Asn Leu Val Asn Arg
                180                 185                 190
Gly Leu Glu Ser Ile Ile Asp Pro Ser Gly Ile Gly Gly Thr Val Asn
            195                 200                 205
Leu Asn Phe Thr Gly Glu Val Glu Thr Tyr Thr Leu Asp Glu Thr Arg
210                 215                 220
Phe Lys Ala Glu Ala Ala Lys Lys Ser His Trp Ser Leu Val Asn Ala
225                 230                 235                 240
Ala Lys Val Tyr Gly Gly Leu Asp Gln Ile Ile Lys Lys Leu Trp Asp
                245                 250                 255
Ser Gly Ser Ile Lys His Leu Tyr Gln Asp Lys Asp Thr Gly Lys Leu
                260                 265                 270
Lys Pro Ile Ile Tyr Gly Thr Ala Gly Asn Asp Ser Lys Ile Glu Gly
                275                 280                 285
Thr Lys Ile Thr Arg Arg Ile Ala Gly Lys Glu Val Thr Leu Asp Ile
                290                 295                 300
Ala Asn Gln Lys Ile Glu Lys Gly Val Leu Glu Lys Leu Gly Leu Ser
305                 310                 315                 320
Val Ser Gly Ser Asp Ile Ile Lys Leu Leu Phe Gly Ala Leu Thr Pro
                325                 330                 335
Thr Leu Asn Arg Met Leu Leu Ser Gln Leu Ile Gln Ser Phe Ser Asp
                340                 345                 350
Ser Leu Ala Lys Leu Asp Asn Pro Leu Ala Pro Tyr Thr Lys Asn Gly
                355                 360                 365
Val Val Tyr Val Thr Gly Lys Gly Asn Asp Val Leu Lys Gly Thr Glu
                370                 375                 380
His Glu Asp Leu Phe Leu Gly Gly Glu Gly Asn Asp Thr Tyr Tyr Ala
385                 390                 395                 400
Arg Val Gly Asp Thr Ile Glu Asp Ala Asp Gly Lys Gly Lys Val Tyr
```

-continued

Phe Val Arg Glu Lys Gly Val Pro Lys Ala Asp Pro Lys Arg Val Glu
                405                 410                 415
                    420                     425                 430

Phe Ser Glu Tyr Ile Thr Lys Glu Ile Lys Glu Val Glu Lys Gly
            435                     440                 445

Leu Leu Thr Tyr Ala Val Leu Glu Asn Tyr Asn Trp Glu Glu Lys Thr
450                     455                 460

Ala Thr Phe Ala His Ala Thr Met Leu Asn Glu Leu Phe Thr Asp Tyr
465                     470                 475                 480

Thr Asn Tyr Arg Tyr Glu Val Lys Gly Leu Lys Leu Pro Ala Val Lys
                485                     490                 495

Lys Leu Lys Ser Pro Leu Val Glu Phe Thr Ala Asp Leu Leu Thr Val
                500                     505                 510

Thr Pro Ile Asp Glu Asn Gly Lys Ala Leu Ser Glu Lys Ser Ile Thr
            515                     520                 525

Val Lys Asn Phe Lys Asn Gly Asp Leu Gly Ile Arg Leu Leu Asp Pro
530                     535                     540

Asn Ser Tyr Tyr Tyr Phe Leu Glu Gly Gln Asp Thr Gly Phe Tyr Gly
545                     550                     555                 560

Pro Ala Phe Tyr Ile Glu Arg Lys Asn Gly Gly Ala Lys Asn Asn
                565                     570                 575

Ser Ser Gly Ala Gly Asn Ser Lys Asp Trp Gly Gly Asn Gly His Gly
                580                     585                     590

Asn His Arg Asn Asn Ala Ser Asp Leu Asn Lys Pro Asp Gly Asn Asn
            595                     600                     605

Gly Asn Asn Gln Asn Asn Gly Ser Asn Gln Asp Asn His Ser Asp Val
610                     615                     620

Asn Ala Pro Asn Asn Pro Gly Arg Asn Tyr Asp Ile Tyr Asp Pro Leu
625                     630                     635                 640

Ala Leu Asp Leu Asp Gly Asp Gly Leu Glu Thr Val Ser Met Asn Gly
                    645                     650                 655

Arg Gln Gly Ala Leu Phe Asp His Glu Gly Lys Gly Ile Arg Thr Ala
                660                     665                 670

Thr Gly Trp Leu Ala Ala Asp Asp Gly Phe Leu Val Leu Asp Arg Asn
                675                     680                 685

Gln Asp Gly Ile Ile Asn Asp Ile Ser Glu Leu Phe Ser Asn Lys Asn
                690                     695                 700

Gln Leu Ser Asp Gly Ser Ile Ser Ala His Gly Phe Ala Thr Leu Ala
705                     710                     715                 720

Asp Leu Asp Thr Asn Gln Asp Gln Arg Ile Asp Gln Asn Asp Lys Leu
                    725                     730                 735

Phe Ser Lys Leu Gln Ile Trp Arg Asp Leu Asn Gln Asn Gly Phe Ser
                740                     745                 750

Glu Ala Asn Glu Leu Phe Ser Leu Glu Ser Leu Asn Ile Lys Ser Leu
                755                     760                 765

His Thr Ala Tyr Glu Glu Arg Asn Asp Phe Leu Ala Gly Asn Ile
770                     775                     780

Leu Ala Gln Leu Gly Lys Tyr Glu Lys Thr Asp Gly Thr Phe Ala Gln
785                     790                     795                 800

Met Gly Asp Leu Asn Phe Ser Phe Asn Pro Phe Tyr Ser Arg Phe Thr
                    805                     810                 815

Glu Ala Leu Asn Leu Thr Glu Gln Gln Arg Arg Thr Ile Asn Leu Thr
                820                     825                 830

```
Gly Thr Gly Arg Val Arg Asp Leu Arg Glu Ala Ala Ala Leu Ser Glu
            835                 840                 845
Glu Leu Ala Ala Leu Leu Gln Gln Tyr Thr Lys Ala Ser Asp Phe Gln
            850                 855                 860
Ala Gln Arg Glu Leu Leu Pro Ala Ile Leu Asp Lys Trp Ala Ala Thr
865                 870                 875                 880
Asp Leu Gln Tyr Gln His Tyr Asp Lys Thr Leu Leu Lys Thr Val Glu
            885                 890                 895
Ser Thr Asp Ser Ser Ala Ser Val Val Arg Val Thr Pro Ser Gln Leu
            900                 905                 910
Ser Ser Ile Arg Asn Ala Lys His Asp Pro Thr Val Met Gln Asn Phe
            915                 920                 925
Glu Gln Ser Lys Ala Lys Ile Ala Thr Leu Asn Ser Leu Tyr Gly Leu
            930                 935                 940
Asn Ile Asp Gln Leu Tyr Tyr Thr Thr Asp Lys Asp Ile Arg Tyr Ile
945                 950                 955                 960
Thr Asp Lys Val Asn Asn Met Tyr Gln Thr Thr Val Glu Leu Ala Tyr
            965                 970                 975
Arg Ser Leu Leu Leu Gln Thr Arg Leu Lys Lys Tyr Val Tyr Ser Val
            980                 985                 990
Asn Ala Lys Gln Phe Glu Gly Lys Trp Val Thr Asp Tyr Ser Arg Thr
            995                 1000                1005
Glu Ala Leu Phe Asn Ser Thr Phe Lys Gln Ser Pro Glu Asn Ala Leu
            1010                1015                1020
Tyr Asp Leu Ser Glu Tyr Leu Ser Phe Phe Asn Asp Pro Thr Glu Trp
1025                1030                1035                1040
Lys Glu Gly Leu Leu Leu Ser Arg Tyr Ile Asp Tyr Ala Lys Ala
            1045                1050                1055
Gln Gly Phe Tyr Glu Asn Trp Ala Ala Thr Ser Asn Leu Thr Ile Ala
            1060                1065                1070
Arg Leu Arg Glu Ala Gly Val Ile Phe Ala Glu Ser Thr Asp Leu Lys
            1075                1080                1085
Gly Asp Glu Lys Asn Asn Ile Leu Leu Gly Ser Gln Lys Asp Asn Asn
            1090                1095                1100
Leu Ser Gly Ser Ala Gly Asp Asp Leu Leu Ile Gly Gly Glu Gly Asn
1105                1110                1115                1120
Asp Thr Leu Lys Gly Ser Tyr Gly Ala Asp Thr Tyr Ile Phe Ser Lys
            1125                1130                1135
Gly His Gly Gln Asp Ile Val Tyr Glu Asp Thr Asn Asp Asn Arg
            1140                1145                1150
Ala Arg Asp Ile Asp Thr Leu Lys Phe Thr Asp Val Asn Tyr Ala Glu
            1155                1160                1165
Val Lys Phe Arg Arg Val Asp Asn Asp Leu Met Leu Phe Gly Tyr His
            1170                1175                1180
Asp Thr Asp Ser Val Thr Val Lys Ser Phe Tyr Ser His Val Asp Tyr
1185                1190                1195                1200
Gln Phe Asp Lys Leu Glu Phe Ala Asp Arg Ser Ile Thr Arg Asp Glu
            1205                1210                1215
Leu Ile Lys Ala Gly Leu His Leu Tyr Gly Thr Asp Gly Asn Asp Asp
            1220                1225                1230
Ile Lys Asp His Ala Asp Trp Asp Ser Ile Leu Glu Gly Gly Lys Gly
            1235                1240                1245
```

```
Asn Asp Ile Leu Arg Gly Gly Tyr Gly Ala Asp Thr Tyr Ile Phe Ser
    1250                1255                1260
Lys Gly His Gly Gln Asp Ile Val Tyr Glu Asp Thr Asn Asn Asp Asn
1265            1270                1275                1280
Arg Ala Arg Asp Ile Asp Thr Leu Lys Phe Thr Asp Val Asn Tyr Ala
        1285                1290                1295
Glu Val Lys Phe Arg Arg Val Asp Asn Asp Leu Met Leu Phe Gly Tyr
            1300                1305                1310
His Asp Thr Asp Ser Val Thr Ile Lys Ser Phe Tyr Asn His Val Asp
        1315                1320                1325
Tyr Gln Phe Asp Lys Leu Glu Phe Ala Asp Arg Ser Ile Thr Arg Asp
    1330                1335                1340
Glu Leu Gly Lys Gln Gly Met Ala Leu Phe Gly Thr Asp Gly Asp Asp
1345                1350                1355                1360
Asn Ile Asn Asp Trp Gly Arg Asn Ser Val Ile Asp Ala Gly Ala Gly
                1365                1370                1375
Asn Asp Thr Val Asn Gly Gly Asn Gly Asp Asp Thr Leu Ile Gly Gly
            1380                1385                1390
Lys Gly Asn Asp Ile Leu Arg Gly Gly Tyr Gly Ala Asp Thr Tyr Ile
        1395                1400                1405
Phe Ser Lys Gly His Gly Gln Asp Ile Val Tyr Glu Asp Thr Asn Asn
    1410                1415                1420
Asp Asn Arg Ala Arg Asp Ile Asp Thr Leu Lys Phe Thr Asp Val Asn
1425                1430                1435                1440
Tyr Ala Glu Val Lys Phe Arg Arg Val Asp Asn Asp Leu Met Leu Phe
                1445                1450                1455
Gly Tyr His Asp Thr Asp Ser Val Thr Val Lys Ser Phe Tyr Ser His
            1460                1465                1470
Val Asp Tyr Gln Phe Asp Lys Leu Glu Phe Ala Asp Arg Ser Ile Thr
        1475                1480                1485
Arg Asp Glu Leu Ile Lys Ala Gly Leu His Leu Tyr Gly Thr Asp Gly
    1490                1495                1500
Asn Asp Asp Ile Lys Asp His Ala Asp Trp Asp Ser Ile Leu Glu Gly
1505                1510                1515                1520
Gly Lys Gly Asn Asp Ile Leu Arg Gly Gly Tyr Gly Ala Asp Thr Tyr
                1525                1530                1535
Ile Phe Ser Lys Gly His Gly Gln Asp Ile Val Tyr Glu Asp Thr Asn
            1540                1545                1550
Asn Asp Asn Arg Ala Arg Asp Ile Asp Thr Leu Lys Phe Thr Asp Val
        1555                1560                1565
Asn Tyr Ala Glu Val Lys Phe Arg Arg Val Asp Asn Asp Leu Met Leu
    1570                1575                1580
Phe Gly Tyr His Asp Thr Asp Ser Val Thr Ile Lys Ser Phe Tyr Asn
1585                1590                1595                1600
His Val Asp Tyr Gln Phe Asp Lys Leu Glu Phe Ala Asp Arg Ser Ile
                1605                1610                1615
Thr Arg Asp Glu Leu Gly Lys Gln Gly Met Ala Leu Phe Gly Thr Asp
            1620                1625                1630
Gly Asp Asp Asn Ile Asn Asp Trp Gly Arg Asn Ser Val Ile Asp Ala
        1635                1640                1645
Gly Ala Gly Asn Asp Thr Val Asn Gly Gly Asn Gly Asp Asp Thr Leu
    1650                1655                1660
Ile Gly Gly Lys Gly Asn Asp Ile Leu Arg Gly Gly Tyr Gly Ala Asp
```

|                       |                       |                       |                       |
|-----------------------|-----------------------|-----------------------|-----------------------|
| 1665                  | 1670                  | 1675                  | 1680                  |

Thr Tyr Ile Phe Ser Lys Gly His Gly Gln Asp Ile Val Tyr Glu Asp
                1685                1690                1695

Thr Asn Asp Asn Arg Ala Arg Asp Ile Asp Thr Leu Lys Phe Thr
            1700                1705                1710

Asp Ile Asn Leu Ser Glu Leu Trp Phe Ser Arg Glu Asn Asn Asp Leu
            1715                1720                1725

Ile Ile Lys Ser Leu Leu Ser Glu Asp Lys Val Thr Val Gln Asn Trp
        1730                1735                1740

Tyr Ser His Gln Asp His Lys Ile Glu Asn Ile Arg Leu Ser Asn Glu
1745                1750                1755                1760

Gln Thr Leu Val Ser Thr Gln Val Glu Lys Met Val Glu Ser Met Ala
                1765                1770                1775

Gly Phe Ala Gln Lys His Gly Gly Glu Ile Ser Leu Val Ser Leu Glu
                1780                1785                1790

Glu Val Lys Gln Tyr Ile Asn Ser Leu Thr Ala Ala Leu
            1795                1800                1805

<210> SEQ ID NO 8
<211> LENGTH: 18
<212> TYPE: DNA
<213> ORGANISM: Actinobacillus pleuropneumoniae

<400> SEQUENCE: 8
tggcactgac ggtgatga                                                 18

<210> SEQ ID NO 9
<211> LENGTH: 18
<212> TYPE: DNA
<213> ORGANISM: Actinobacillus pleuropneumoniae

<400> SEQUENCE: 9
ggccatcgac tcaaccat                                                 18

<210> SEQ ID NO 10
<211> LENGTH: 26
<212> TYPE: DNA
<213> ORGANISM: Actinobacillus pleuropneumoniae

<400> SEQUENCE: 10
agccatatgg gcgatttaaa tttcag                                        26

<210> SEQ ID NO 11
<211> LENGTH: 24
<212> TYPE: DNA
<213> ORGANISM: Actinobacillus pleuropneumoniae

<400> SEQUENCE: 11
tatggatcct ccgtgcttct gagc                                          24

<210> SEQ ID NO 12
<211> LENGTH: 20
<212> TYPE: DNA
<213> ORGANISM: Actinobacillus pleuropneumoniae

<400> SEQUENCE: 12
gggacagtgg ctcaattaag                                               20

<210> SEQ ID NO 13
<211> LENGTH: 20

```
<212> TYPE: DNA
<213> ORGANISM: Actinobacillus pleuropneumoniae

<400> SEQUENCE: 13
agctgtaaac tccaccaacg                                               20

<210> SEQ ID NO 14
<211> LENGTH: 28
<212> TYPE: DNA
<213> ORGANISM: Actinobacillus pleuropneumoniae

<400> SEQUENCE: 14
cgccatatga caaaattaac tatgcaag                                      28

<210> SEQ ID NO 15
<211> LENGTH: 26
<212> TYPE: DNA
<213> ORGANISM: Actinobacillus pleuropneumoniae

<400> SEQUENCE: 15
cgcgaattca gcgacacaag agatat                                        26

<210> SEQ ID NO 16
<211> LENGTH: 9
<212> TYPE: PRT
<213> ORGANISM: Actinobacillus pleuropneumoniae

<400> SEQUENCE: 16

Tyr Ser Asp Ser Ala Asn Ser Lys Lys
1               5
```

ACTINOBACILLUS PLEUROPNEUMONIAE SUBUNIT VACCINE

This is a continuation of application Ser. No. 09/057,570, filed Apr. 9, 1988, now U.S. Pat. No. 6,013,266.

FIELD OF THE INVENTION

The present invention relates to live attenuated bacteria of the genus *Actinobacillus pleuropneumoniae*, having a mutation in a gene encoding a toxin, methods for the production of such bacteria, to vaccines comprising such bacteria, methods for the production of such vaccines, to vaccines comprising a toxin, methods for the production of such vaccines and methods for the protection of animals against infection with bacteria of the genus, *Actinobacillus pleuropneumoniae*.

BACKGROUND OF THE INVENTION

Bacteria belonging to the genus Actinobacillus all produce so-called RTX-toxins. (RTX stands for repeat in toxin).

It is the presence of these RTX-toxins that highly contributes to the pathogenic character of these bacteria.

The RTX-toxins have been extensively reviewed by Braun et al. (Critical Rev. in Microbiol. 18(2): 115–158 (1991)). RTX-toxins in Gram-negative strains have also been reviewed in Welch, R. A. (Molecular Microbiology 5/3: 521–528 (1991)) and in Welch et al. (Inf. Agents and Disease 4: 254–272 (1995)).

All known RTX-toxins display some kind of cytotoxic or cytolytic activity. The target-cell-and host-specificity differ however, depending on the toxin and on differences in acylation (McWhinney et al.; J. Bact. 174: 291–297 (1992) and Hackett et al.; J. Biol. Chem. 270: 20250–20253 (1995)). As a result of the difference in target cells, the various toxins of the RTX-toxin family are known e.g. as haemolysin, cytolysin or cytotoxin. The genus Actinobacillus comprises a number of different species, inter alia, *Actinobacillus pleuropneumoniae*, *A. actinomycetemcomitans*, *A. suis*, *A. rossii*, *A. equuli* and *A. lignieresii*.

*Actinobacillus pleuropneumoniae* produces serotype-dependent RTX-toxins that are cytotoxic/cytolytic to pig, horse, bovine and human erythrocytes, to rabbit and porcine neutrophils and to porcine alveolar macrophages. (Rosendal et al; Am. J. Vet. Res. 49: 1053–1058 (1988), Maudsley J. R. and Kadis S; Can. J. Microbiol. 32: 801–805 (1986), Frey. J and Nicolet. J; Inf. & Imm. 56:2570–2575 (1988), Bendixon et al; Inf. & Imm. 33: 673–676 (1981), Kamp, E. M. and van Leengoed, L. A. M. G.; J. Clin. Microbiol. 27: 1187–1191 (1989)).

Infections with Actinobacillus in pigs are the cause of severe economic losses to pig industry, due to acute mortality in young pigs and reduced weight gain in older animals.

The genetic organisation of the operons involved in the synthesis, activation and transportation of the RTX toxins in Gram-negative bacteria has been reviewed recently by Coote, J. G. (FEMS Microbiology reviews 88: 137–162 (1992)). Frey has specifically reviewed the known three RTX-toxins in *Actinobacillus pleuropneumoniae* in Bacterial Protein Toxins, Zbl Bakt. Suppl. 24, p. 322-, Freer et al. (Eds.), Gustaf Fischer, Stutttgart, Jena, New York, 1994.

In *Actinobacillus pleuropneumoniae,* this kind of RTX-operon contains four genes: the actual Toxin-gene (A), an Activator-gene (C), and two genes (B and D) encoding proteins involved in secretion of the toxin into the surrounding medium. The primary translation-product of the Toxin-gene (A) is a non-toxic protein, of which the toxic activity is activated by the Activator-gene (C) product.

Until recently, it was assumed that only three RTX-toxins, all having the above-described genetic organisation or at least having the Toxin-gene (A) and Activator-gene (C), existed in Actinobacillus species.

These three RTX-toxins, ApxI, Apx-II and Apx-III have respectively a pronounced haemolytic activity (ApxI), a mild haemolytic activity (Apx-II) or a macrophage-cytotoxic activity (Apx-III).

The various toxic activities are fairly randomly divided over the serotypes. There are four subgroups:

- a subgroup A, represented by serotypes 1, 5, 9 and 11, producing ApxI and Apx-II,
- a subgroup B, represented by serotypes 2, 3, 4, 6 and 8, producing Apx-II and Apx-III,
- a subgroup C, represented by serotype 10, producing ApxI only,
- a subgroup D, represented by serotype 7 and 12, producing Apx-II only, It is known, that ApxI, -II, and -III all are essential elements in universal vaccines against *Actinobacillus pleuropneumoniae* infection: a vaccine not comprising at least ApxI, -II, and -III will not provide protection against all *Actinobacillus pleuropneumoniae* serotypes. Also, a vaccine not comprising at least the Apx-toxins of one specific serotype will not even induce protection against that single serotype.

Subunit vaccines based on in vitro synthesised RTX-toxins from A. pleuropneumoniaethat lost their toxicity have been described earlier, e.g. in European Patent EP No. 0,354,628, in which subunit vaccines based upon a haemolysin and a cytotoxin of *A. pleuropneumoniae* are disclosed, and in European Patent EP No 0,453,024, in which *A. pleuropneumoniae* subunit vaccines based upon haemolysins, cytotoxins and outer membrane proteins are disclosed.

There are however four important disadvantages to subunit vaccines in general:

- high amounts of antigenic material are needed in order to adequately trigger the immune system.
- usually, only B-cell immunity is triggered.
- several protective antigens are only triggered in vivo, and therefore can not be present in subunit vaccines.
- a live pathogenic bacterium has many important immunogenic molecules, such as Outer Membrane Proteins and capsular polysaccharides, all potentially important for protection and thus to be included in an efficient subunit vaccine.

Next to the obvious problems mentioned under points one and two, especially the fourth point makes it difficult to make an efficient subunit vaccine.

This is e.g. illustrated by the *A. pleuropneumoniae* subunit vaccine disclosed in European Patent EP No 0,453,024 mentioned above, in which four different subunits (three RTX-toxins and an outer membrane protein) are combined in one vaccine.

It is clear, that in order to overcome the disadvantages of subunit vaccines against Pasteurellacea-infection, a live attenuated vaccine would be highly desirable.

A live attenuated vaccine has the following advantages:

- it can be administered in low doses (it is self-replicating)
- it closely mimics the natural/wild-type infection it provides all the possible immunologically important antigens at the same time.

Nevertheless, in spite of the clear advantages, no live vaccines based on *Actinobacillus pleuropneumoniae* were commercially available prior to the present invention.

The reason for this lies in the following paradox: as mentioned before, ApxI, -II, and -III all are essential elements of universal vaccines against *Actinobacillus pleuropneumoniae* infection. Live vaccines therefore have to produce these three RTX-toxins. These three RTX-toxins are however strong virulence factors in all Actinobacillus species (see e.g. Coote, J. G.; FEMS Microbiology reviews 88: 137–162 (1992), Tascon et al.; Mol. Microbiol. 14: 207–216 (1994)), Jansen et al.; Inf. & Imm. 63: 27–37 (1995)).

Deletion of the RTX-toxins in order to attenuate the virulence of live App strains is technically feasible, but this does not provide a solution for the dilemma: such RTX-negative strains would be useless as live attenuated vaccine strains since they do no longer induce immunity in the host against the haemolytic/cytotoxic activity of *Actinobacillus pleuropneumoniae* field strains.

Virulence factors that, although important in the induction of immunity, do play a less important role in building up immunity than ApxI, -II and -III, and thus can in principle be deleted are however currently not known.

It would thus be highly desirable to have a site on the genome of App that attributes to virulence and therefore leads to an attenuated App strain when modified, whereas at the same time it is, although useful in triggering immunity, dispensable from a vaccine point of view. No such sites are however currently known. Moreover, it would be highly desirable if such a site would be universally present in all App strains, instead of being restricted to certain serotypes. Such a site would then allow all different serotypes to be attenuated by deletion of that same site.

It is one of the objectives of the present invention to provide such an attenuation site, universally present in all *Actinobacillus pleuropneumoniae* strains regardless of their serotype.

Recently, a new gene was found in a serotype 1 strain of *Actinobacillus pleuropneumoniae* (Thesis T. J. Anderson November 1995).

Although this gene does not resemble the known Actinobacillus ApxI, -II and -III genes, it bears resemblance to RTX-toxin genes known from bacteria belonging to *Neisseria meningitidis*, for which reason it was named RTX-gene apxIV. The gene however differs in almost all aspects from the three known RTX-toxin genes apxI, -II and -III present in the various species of the Actinobacillus family as described above. First of all, the genomic organisation is completely different. Secondly, there is no activator-mechanism as is found for the known Apx-toxins. In the third place, no specific in vivo haemolytic or cytotoxic activity could at that time be attributed to the gene, or it's possible gene product.

SUMMARY OF THE INVENTION

It was now surprisingly found that this gene, fully in contrast with the three known RTX-genes, is present in all bacteria of the species Actinobacillus pleuropneumoniae, regardless their serotype. This was determined by hybridisation of a probe comprising apxIV coding sequences with restriction fragments of the DNA from *Actinobacillus pleuropneumoniae* of all serotypes as described in Example 6 and 7.

Unexpectedly it was found now that apxIV deletion mutants are viable, but they behave less virulent compared to their apxIV-possessing parent strains.

Therefore, it was determined that the gene product, the ApxIV toxin is a virulence factor in all *Actinobacillus pleuropneumoniae* strains. This is an unexpected conclusion, since up until now, no effects at all, let alone effects possibly influencing virulence had been attributed to the gene product in vivo. In fact, up until now there was not even proof that the gene was expressed in *Actinobacillus pleuropneumoniae* in vivo or in vitro anyway.

It therefore is one of the merits of the invention that it was found that:

the apxIV gene is present in all *A. pleuropneumoniae* strains regardless the serotype, the apxIV gene product is a virulence factor in all *A. pleuropneumoniae* serotypes,

*A. pleuropneumoniae* strains with a deletion in the apxIV gene are still viable but have a decreased virulence without significantly impairing the immunogenic properties of the strains, Therefore, the invention provides for the first time live attenuated bacteria of the species *Actinobacillus pleuropneumoniae*, that do not produce a functional ApxIV toxin.

DETAILED DESCRIPTION OF THE INVENTION

A functional ApxIV toxin is considered to be a protein that has all the characteristics of the ApxIV toxin as expressed in a wild-type bacterium, and is expressed at the wild-type level. Therefore, a non-functional ApxIV toxin is considered to be a toxin that lacks some or all of the characteristics of the ApxIV toxin as expressed in a wild-type bacterium, and/or is expressed at a level, insufficient to obtain wild-type effects of ApxIV toxin.

The inability to produce the ApxIV toxin can e.g. be due to modifications in the coding sequence encoding the ApxIV toxin. It may also be e.g. the result of modifications in regions known to be involved in transcription of the apxIV gene, such as the promotor region, or of modifications in regions involved in translation, such as the ribosome binding site.

The overall structure of the apxIV gene is given in FIG. 1.

In this figure, the direct repeat regions, characteristic for ApxIV toxin are indicated by dashed boxes, whereas the also ApxIV-specific glycine-rich nonapeptide regions are indicated by black arrows. The repeats are found at the C-terminal part of ApxIV. These characteristic features are present in all *Actinobacillus pleuropneumoniae* serotypes. The nucleic acid sequence and amino acid sequence of two serotypes are represented in SEQ. ID. No. 1–4. SEQ. ID. NO. 1 shows the nucleic acid sequence of the apxIV gene of App serotype 1, and SEQ. ID. NO. 2 shows the matching amino acid sequence of the serotype 1 ApxIV toxin. SEQ. ID. NO. 3 shows the nucleotide sequence of the apxIV gene of App serotype 3, whereas SEQ. ID. NO. 4 shows the matching amino acid sequence of the serotype 3 ApxIV toxin. FIG. 2 shows the strikingly high level of conservation at amino acid level, especially in the N-terminal 650 amino acids, between the Apx-toxins of the various *Actinobacillus pleuropneumoniae* serotypes. This is also a remarkable characteristic of the apxIV genes. It is clear from FIG. 1, that a variation in the number of repeats at the C-terminal part of the toxin may occur, depending on the serotype. This variation accounts for the difference in size of the genes and encoded toxins obtained from the various serotypes.

There may be some variation in nucleic acid sequence even between apxIV genes isolated from different isolates of

*Actinobacillus pleuropneumoniae,* belonging to the same serotype. This is due to natural variation well known in the art to exist in all organisms. It is possible that some amino acids in the ApxIV toxin encoded by the apxIV gene are replaced by others in the ApxIV toxin of another serotype, while the polypeptide is not altered in its function. For instance, a polypeptide containing Asp at a certain site, and its variant containing Asn at the comparable site still have the same properties. This process in which an amino acid is replaced by an functionally analogous amino-acid is called functional displacement. In this case the variant proteins are called functional variants.

Another cause of variation is the phenomenon of degeneracy of the genetic code. Shortly, it means, that e.g. the amino acid glutamic acid is coded for by both GAT and GAA. This phenomenon holds for all amino acids, except Met and Trp. Thus, it is obvious, that e.g. the ApxIV toxin of serotype 1, as given in the present invention can not only be coded for by the nucleotide sequence given in SEQ ID NO: 1 but also by a very large variety of other sequences, still all giving the same or functionally the same polypeptides.

Therefore, a variant apxIV sequence encoding a polypeptide that is functionally comparable to the ApxIV toxin falls within the scope of the present invention.

Live attenuated bacteria according to the invention can be obtained in several ways. One possible way of obtaining such bacteria is by means of classical methods such as the treatment of wild-type *Actinobacillus pleuropneumoniae* bacteria with mutagenic agents such as base analogues, treatment with ultraviolet light or temperature treatment. Strains that do not produce a functional ApxIV toxin do not or to a lesser extend induce anti-ApxIV toxin antibodies, and therefore can easily be selected in animal tests.

The necessary antiserum can be obtained as described below in Example 3.

Another possibility is to deliberately introduce, using recombinant DNA-technology, a well-defined mutation in the gene encoding the ApxIV toxin. Such a mutation may be an insertion, a deletion, a replacement of one nucleotide by another one or a combination thereof, with the only proviso that the mutated gene no longer encodes a functional ApxIV toxin. It can easily be seen, that especially mutations introducing a stop-codon in the open reading frame, or mutations causing a frame-shift in the open reading frame are very suitable to obtain a strain which no longer encodes a functional ApxIV toxin. Such mutations can e.g. be made by means of in vitro site directed mutagenesis using the Transformer® kit sold by Clontech. Many other standard recombinant DNA techniques such as digestion of the gene with a restriction enzyme, followed by endonuclease treatment and religation, are equally applicable.

Therefore, in a preferred form, this embodiment of the invention relates to live attenuated bacteria in which the gene encoding the ApxIV toxin comprises a mutation.

Well-defined mutations involving the deletion of fragments of the apxIV gene or even the whole gene, or the insertion of heterologous DNA-fragments, when compared to classically induced mutations, have the advantage that they will not revert to the wild-type situation.

Thus, in a more preferred form, this embodiment of the invention refers to live attenuated bacteria in which the gene encoding the ApxIV toxin comprises an insertion and/or a deletion.

Given the large amount of vaccines given nowadays to pigs, it is clear that combined administration of several vaccines would be desirable, if only for reasons of decreased vaccination costs. It is therefore very attractive to use live attenuated vaccine strains as a recombinant carrier for heterologous genes, encoding antigens selected from other pathogenic micro-organisms or viruses. Administration of such a recombinant carrier has the advantage that after administration of such a carrier, immunity is induced against two or more diseases at the same time. The live attenuated bacteria according to the present invention provide a very suitable carrier for heterologous genes, since the gene encoding the ApxIV toxin can be used as an insertion site for such heterologous genes. The use of the apxlV gene as an insertion site has the advantage that at the same time the apxIV gene is inactivated, and the newly introduced heterologous gene can be expressed in accordance with the homologous *Actinobacillus pleuropneumoniae* genes. The construction of such recombinant carriers can be done routinely, using standard molecular biology techniques such as homologous recombination. Therefore, in an even more preferred embodiment, the present invention relates to live attenuated bacteria of the species *Actinobacillus pleuropneumoniae* that do not produce a functional ApxIV toxin, and in which there is a heterologous gene inserted in the apxIV gene. Such a heterologous gene can, as mentioned above, e.g. be a gene encoding an antigen selected from other pathogenic micro-organisms or viruses. Another possibility is to insert a gene encoding a protein involved in triggering the immune system, such as an interleukine or an interferone.

In a still even more preferred form of the invention, the heterologous gene encodes one or more antigens selected from the group consisting of Porcine Reproductive Respiratory Syndrome (PRRS) virus, Pseudorabies virus, Porcine Influenza virus, Porcine Parvovirus, Transmissible Gastroenteritis virus, rotavirus, *Escherichia coli, Erysipelothrix rhusiopathiae, Pasteurella multocida, Bordetella bronchiseptica, Haemophilus parasuis* and *Streptococcus suis.*

There is however a serious pitfall in expression of heterologous genes in recombinant carriers: it is known that several proteins are toxic if they are expressed in heterologous bacteria. Therefore, genes encoding such proteins can never be introduced in heterologous carriers, since successful recombinants will eventually die as a result of the expression a certain amount of the heterologous gene. The P2-protein of *Haemophilus influenzae,* to name just one example, can simply not be expressed in *E. coli.* (Munson et al., Infect. & Immun. 57: 88–94 (1989)). It is one of the objectives of the present invention to offer a recombinant live carrier that does not have this drawback. It was unexpectedly found, that although the apxIV gene is efficiently expressed in vivo (see Example 5), it is not expressed in vitro (see Example 4). This was concluded from the failure to show the presence of ApxIV toxin in in vitro grown *A. pleuropneumoniae* cultures. This means that ApxIV expression is switched on or off, depending on the environment in which *A. pleuropneumoniae* is grown. This feature offers an unexpected advantage over known live recombinant carriers: if the expression of the heterologous gene is brought under the control of the apxIV promoter, the live attenuated *P. pleuropneumoniae* carrier according to the invention can be grown in vitro to high densities, regardless the inserted heterologous gene, since the foreign gene will not be expressed under these conditions. After administering a number of bacteria to the host, the expression of the heterologous gene will start and at some time during replication or after the death of the bacterium it will become available to the immune system of the host. The heterologous gene to be expressed can be functionally linked to the apxIV promoter by e.g. replacing the coding sequence of the apxIV gene by the coding region of the heterologous gene. It is not necessary to replace the whole apxIV gene: it suffices to replace the ATG-codon of ApxIV by the coding region of the heterologous gene including its stop-codon. It is also possible to express a heterologous gene under the influence of the apxIV promoter by making a fusion construct. This can be made by inserting the heterologous gene in frame with the apxIV reading frame downstream of the apxIV ATG codon.

The wording "functionally linked to the apxIV promoter" means that transcription of the heterologous gene starts at the apxIV promoter.

It goes without saying that each location of the inserted heterologous gene in which it is functionally linked to the apxIV promotor falls within the scope of the invention.

Therefore, the most preferred form of this embodiment relates to live attenuated bacteria according to the present invention, carrying a heterologous gene that is functionally linked to the promotor region of the apxIV gene.

The surprising finding that the native apxIV promotor is a switchable promotor that is switched off in vitro and switched on in vivo makes this promotor a very versatile expression tool both in it's natural host and as a heterologous promotor in other bacteria. When used as a heterologous promotor in other bacteria, the DNA comprising the promotor can be isolated from its host and transferred to a bacterium other than Actinobacillus pleuropneumoniae. Another option that has now become feasible, is the cloning of several copies of the apxIV promotor each controlling the expression of another gene. This can be done in the host bacterium Actinobacillus pleuropneumoniae, but this principle of multiple copies is equally applicable to other bacteria. As mentioned above, the promotor can be used for the selective in vivo expression of one or more heterologous genes encoding antigens selected from other pathogenic micro-organisms or viruses. The promotor can also be used for the expression of a heterologous DNA sequence encoding a cytokine such as an interleukin, Tumor Necrosis Factor or an interferon. Several cytokines, e.g. interferons are known to play an important role as immune modulators. Thus it may be advantageous to express such genetic information under the control of the apxIV promotor.

Therefore, another embodiment of the invention relates to a nucleotide sequence harbouring the promotor controling the expression of the apxIV gene.

The switchable promotor that in the native situation controls the expression of the apxIV gene, was now found to be located in the DNA fragment between position 451 and 1132 of SEQ ID NO: 5. It is clear, that those parts of this DNA fragment that are not essential promotor elements need not necessarily be present in the fragment. Thus, shorter fragments of this DNA fragment in which the promotor activity is retained, are equally suitable for the expression of heterologous genes. Therefore, a more preferred form of this embodiment relates to a nucleotide sequence comprising the DNA fragment from position 451 to 1132 of SEQ ID NO: 5 or a subfragment thereof still having promotor activity.

Bacterial promotors all share two consensus regions, the so-called −10 and the −35 region. Although the flanking sequence of these consensus regions may to a certain extend influence the efficiency of the promotor, it can be advantageous to use only that part of the promotor region that comprises the DNA fragment between −35 and the ATG codon. This DNA fragment is located between position 617 and position 641 of SEQ ID NO: 5.

Therefore, in a more preferred form of this embodiment the invention relates to a nucleotide sequence comprising the DNA fragment from position 617 to 641 of SEQ ID NO: 5.

The present invention also relates to ApxIV toxin as a subunit vaccine component.

Subunit vaccines will most probably comprise the three known Apx-toxins. This was mentioned above. Since it was unexpectedly found, that the ApxIV toxin is however present in all A. pleuropneumoniae serotypes as mentioned above, it is a desirable additional component of subunit vaccines: neutralising antibodies raised against the ApxIV toxin provide protection against the ApxIV toxin produced by each and every Actinobacillus pleuropneumoniae strain, regardless the serotype. Therefore, another embodiment of the invention relates to subunit vaccines for the protection of animals against infection with a bacterium of the species Actinobacillus pleuropneumoniae, that comprise purified ApxIV toxin. The ApxIV toxin can be administered alone, or in combination with any or all of the toxins ApxI, -II and -III mentioned above and/or e.g. in combination with Outer Membrane Proteins (OMPS) of Actinobacillus pleuropneumoniae. Such vaccines can easily be prepared by admixing ApxIV toxin in an amount sufficient to induce an immune response, and a pharmaceutically acceptable carrier. Production of the ApxIV toxin is possible by introducing the apxIV gene in a suitable expression vector, expression of the gene and isolation of the toxin. Many versatile expression systems are known in the art, such as bacterial expression systems, baculovirus expression systems and mammalian cell expression systems. In Example 3 it is described how to obtain the ApxIV toxin by expression of the gene in E. coli.

Still another embodiment of the invention relates to live attenuated vaccines comprising live attenuated bacteria as described above for the protection of animals against infection with a bacterium of the species Actinobacillus pleuropneumoniae. Such vaccines can be obtained by admixing live attenuated bacteria with a pharmaceutically acceptable carrier. These vaccines comprise at least an immunogenically effective amount of the live attenuated producing bacterium according to the invention. Immunogenically effective means that the amount of live attenuated bacterium administered at the moment of vaccination is sufficient to induce in the host an effective immune response to virulent forms of the RTX-toxin producing bacterium. The useful dosage to be administered will vary depending on the age, weight and animal vaccinated, the mode of administration and the type of pathogen against which vaccination is sought. The vaccine may comprise any dose of bacteria, sufficient to evoke an immune response. Doses ranging between $10^3$ and $10^{10}$ bacteria are e.g. very suitable doses.

The pharmaceutically acceptable carrier may be as simple as water, but it may e.g. also comprise culture fluid in which the bacteria were cultured. Another suitable carrier is e.g. a solution of physiological salt concentration. Other examples of pharmaceutically acceptable carriers or diluents useful in the present invention include stabilisers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Adjuvantia are non-specific stimulators of the immune system. They enhance the immune response of the host to the invading pathogen. Examples of adjuvantia known in the art are Freunds Complete and Incomplete adjuvans, vitamin E, non-ionic block polymers, muramyldipeptides, ISCOMs (immune stimulating complexes, cf. for instance European Patent EP 109942), Saponins, mineral oil, vegetable oil, and Carbopol (a homopolymer). Adjuvantia, specially suitable for mucosal application are e.g. the *E. coli* heat-labile toxin (LT) or Cholera toxin (CT).

Other suitable adjuvants are for example aluminium hydroxide, phosphate or oxide, oil-emulsions (e.g. of Bayol F (R) or Marcol 52 (R), saponins or vitamin-E solubilisate.

Therefore, in a preferred form, the vaccines according to the present invention comprise an adjuvant.

For administration to animals, the vaccine according to the presentation can be given inter alia intranasally, intradermally, subcutaneously, by aerosol or intramuscularly.

There are several ways to store both subunits and live organisms. Storage in a refrigerator is e.g. a well-known method. Also often used is storage at −70° C. in a buffer containing glycerol. Bacteria can also be kept in liquid nitrogen. Freeze-drying is another way of conservation. Freeze-dried bacteria can be stored and kept viable for many years. Storage temperatures for freeze-dried bacteria may well be above zero degrees, without being detrimental to the viability. Freeze-drying is equally applicable for subunits.

Freeze-drying can be done according to all well-known standard freeze-drying procedures. Optional beneficial additives, such as e.g. skimmed milk, trehalose, gelatin or bovine serum albumin can be added in the freeze-drying process.

Therefore, in a more preferred embodiment, the vaccine according to the present invention is in a freeze-dried form.

In an even more preferred form of this embodiment, the vaccine additionally comprises one or more antigens selected from other pathogenic micro-organisms or viruses. Such a vaccine can be obtained by adding one or more antigens selected from other pathogenic bacteria or viruses to the live attenuated bacterium according to the invention and a pharmaceutically acceptable carrier as described above.

Of course, it is possible to add not only one or more antigens, but also one or more of the whole pathogens as such, in an inactivated or live form.

It can alternatively be obtained by cloning the genetic information encoding one or more antigens selected from other pathogenic micro-organisms or viruses into the live attenuated bacterium, using known recombinant DNA technology as described above.

Such vaccines are of course less stressing for the animal to be vaccinated than separate vaccinations with each of the pathogens, both from a medical and a physical point of view.

In a still even more preferred form, these antigens are selected from the group consisting of Porcine Reproductive Respiratory Syndrome (PRRS) virus, Pseudo-rabies virus, Porcine Influenza virus, Porcine Parvovirus, Transmissible Gastroenteritis virus, rotavirus, *Escherichia coli, Erysipelothrix rhusiopathiae, Pasteurella multocida, Bordetella bronchiseptica, Haemophilus parasuis* and *Streptococcus suis*.

The invention also relates to methods for the preparation of a live attenuated bacterium of the species *Actinobacillus pleuropneumoniae* that is not capable of producing a functional ApxIV toxin. These method comprise the introduction of a mutation in the gene encoding the apxIV protein. Both classical mutation techniques, using mutagenic agents, and recombinant DNA techniques well-known in the art for insertion, replacement or deletion of genetic information from the apxIV gene are applicable.

In a preferred form, the above mentioned methods are used for the introduction of a deletion.

Methods for the preparation of a live attenuated vaccine according to the invention, that comprise admixing bacteria according to the invention with a pharmaceutically acceptable carrier are also part of the invention.

Also falling within the scope of the invention are methods for the preparation of a subunit vaccine. Such methods comprise the mixing of purified ApxIV toxin with a pharmaceutically acceptable carrier.

Another generally acknowledged problem in the field of vaccination with live vaccines is the following: the presence of antibodies against a certain pathogen in the serum of a host animal indicates that the host has been infected with the pathogen, either in a virulent or attenuated form. It is however impossible to discriminate between field-infected animals and animals vaccinated with a live vaccine strain. The live attenuated *Actinobacillus pleuropneumoniae* according to the present invention offers a solution to this problem as follows:

As described in Example 3, the apxIV gene of *Actinobacillus pleuropneumoniae* serotype 1 has been isolated and expressed in a heterologous host cell. This expression product was subjected to PAGE and then used for Westernblotting. The blots were incubated with convalescent serum obtained from a deliberately *Actinobacillus pleuropneumoniae*-infected pigs, and sera from field-strains. It was found that the apxIV gene is expressed in vivo in all *Actinobacillus pleuropneumoniae* field strains tested. This implicates, that pigs infected with *Actinobacillus pleuropneumoniae* will always have antibodies against the strain with which they were infected, regardless the serotype of the infectious strain.

The live attenuated bacteria according to the present invention can, due to the deletion of the apxIV gene, no longer make ApxIV toxin. Therefore animals vaccinated with a live attenuated *Actinobacillus pleuropneumoniae* strain according to the invention will not have antibodies against ApxIV toxin in their serum.

In a comparative test, e.g. an ELISA test, such sera will therefore react with all immunogenic *Actinobacillus pleuropneumoniae*-proteins such as e.g. ApxI, II and/or III, but not with ApxIV. Sera from pigs infected with an *Actinobacillus pleuropneumoniae* field strain however will react with all immunogenic *Actinobacillus pleuropneumoniae*-proteins, including ApxIV. Therefore, the live attenuated *Actinobacillus pleuropneumoniae* according to the present invention turns out to be a very suitable marker vaccine, i.e. a vaccine strain that can be discriminated from a field strain.

A diagnostic test for the discrimination between vaccine strains and field strains can be a simple ELISA-test in which purified ApxIV toxin is coated to the wall of the wells of an ELISA-plate. Incubation with serum from pigs to be tested, followed by e.g. incubation with a labelled anti-pig antibody can then reveal the presence or absence of antibodies against ApxIV toxin.

Another example of a diagnostic test system is e.g. the incubation of a Western blot comprising purified ApxIV toxin with serum of pigs to be tested, followed by detection of specific anti-ApxIV antibodies.

Therefore, diagnostic test for the discrimination between sera from pigs infected with *Actinobacillus pleuropneumoniae* field strains and from pigs vaccinated with a vaccine comprising live attenuated vaccine *Actinobacillus pleuropneumoniae* strains according to the invention, that comprise purified ApxIV toxin. also fall within the scope of the invention.

Still another problem seen in pig health care is the following: It is difficult to determine in a both quick and unambiguous manner if a pig is infected with *Actinobacillus pleuropneumoniae* or *A. suis,* or possibly a combination of both. Diagnostic tests for the specific detection of *A. suis* are currently not available. This is mainly due to the fact that *A. pleuropneumoniae* and *A. suis* share so many antigens. As an example, two highly antigenic Apx-toxins, ApxI and ApxIII have highly conserved homologues in e.g. *A. suis* (Van Ostaayen et al., submitted for publication).

The known RTX-genes, encoding the ApxI, -II and -III toxins or homologues are found in practically all members of the genus Actinobacillus, such as *A. pleuropneumoniae, A. suis, A. rossii* and *A. equuli.* Thus, it was initially assumed by the inventors, that the new RTX-toxin ApxIV would also be common to all members of the genus Actinobacillus.

It was however found after testing a the swine-pathogenic Actinobacillus, again surprisingly in contrast with the known three RTX-genes, that this novel RTX-gene apxIV is only present in the swine-pathogen *Actinobacillus pleuropneumoniae.* It is absent in all other common swine pathogenic Actinobacillus species, and therefore it is also absent in *Actinobacillus suis. l See Example* 6 and 7.

Therefore, it was surprisingly noticed that the presence of antibodies against ApxIV in the serum of a pig is a quick and unambiguous proof that the pig has been infected with *A. pleuropneumoniae,* and not with *A. suis* or any other swine-pathogen *Actinobacillus species.*

Thus the present invention also provides a diagnostic test based on the presence or absence of antibodies against ApxIV, and therefore a discriminating test for specifically distinguishing an infection with *A. pleuropneumoniae* from an infection with *A. suis*

Such a test can e.g. be an ELISA test that comprises in separate wells the ApxI and -II toxins, present in both *A. pleuropneumoniae* and *A. suis* and the purified ApxIV toxin. Serum from *A. suis*-infected animals will react only with the wells comprising the ApxI and -II whereas *A. pleuropneumoniae*-infected animals will also react with the well comprising the purified ApxIV toxin.

EXAMPLE 1

Cloning and analysis of the apxIV gene of *A. pleuropneumoniae* serotype 1

Standard molecular biological procedures (plasmid DNA isolation, restriction digestion, agarose gel electrophoresis, Southern blotting, ligation, transformation, electroporation) were, unless stated otherwise, essentially performed as described in Sambrook et al. (Molecular Cloning, A Laboratory Manual, Cold Spring Harbor, N.Y., 1989) or Ausubel et al., (Current Protocols in Molecular Biology. John Wiley & Sons, N.Y., 1987). PCR was performed essentially as described in Innis et al., (PCR protocols, A guide to Methods and Applications, Academic Press Inc., San Diego, 1990). Chromosomal DNA isolation was performed according to Pitcher et al., (Lett. Appl. Microbiol., 8;151–156, 1989). The origin of all *A. pleuropneumoniae* reference strains (serotype 1: strain 4074; serotype 2: strain S1536: serotype 3: S1421; serotype 4 M62; serotype 5a: K17; serotype 5b: L20; serotype 6: femø; serotype 7: WF83; serotype 8: 405; serotype 9: CVI13261; serotype 10: 13039; serotype 11: 56153 and serotype 12: 8329) is described by Frey and Nicolet, (J. Clin. Microbiol., 28;232–236, 1990). *A. pleuropneumoniae* serotype 3 strain HV114 is a field isolate (i.e. one of the serotype 3 strains tested in Beck et al., J. Clin. Microbiol., 32;2749–2754, 1994). Other Actinobacillus strains used; *A. rossii:* ATCC 27072; *A. equuli:* ATCC 19392; *A. suis:* ATCC 15558. *Pasteurella haemolytica* type 1 strain ATCC 14003 was used.

*E. coli* host strains used: XL1-blue (Stratagene, La YolIa, Calif.; genotype: recA1 endA1 gyrA96 thi-1 hsdR17 supE44 relA1 lac [F' proAB lacI$^q$ZDM15 Tn10 (Tet$^r$)]) and HMS174 (DE3) (AMS Biotechnology Ltd, Switzerland; genotype: F$^-$ recA ($r_{K12-}m_{K12+}$) rif$^r$ IDE3).

On the basis of the preliminary sequence data obtained from the thesis of T. J. Anderson (University of Guelph, 1995), two primers, designated APXIVA-1L (5'-TGGCACTGACGGTGATGA-3' (SEQ ID NO: 8)) and APXIVA-1R (5'-GGCCATCGACTCAACCAT-3' (SEQ ID NO: 9)) were synthesised. These primers were used in a PCR amplification, with chromosomal DNA from *A. pleuropnumoniae* serotype 3 strain HV114 and serotype 1 reference strain 4074 as a template. With both strains a fragment of 442 bp was amplified. The fragment derived from the serotype 3 chromosomal DNA was labelled with Digoxigenin-11-dUTP (Boehringer Mannheim) according to the protocol of the manufacturer (this fragment was designated probe APXIVA, see FIG. 4). The labelled probe was subsequently used to hybridize a Southern blot containing ClaI digested chromosomal DNA from strain 4074. The probe hybridised with a fragment of approximately 8.0 kb. The apxIV gene from serotype 1 strain 4074 was isolated by ligating ClaI digested chromosomal DNA into ClaI digested pBluescript II SK$^-$ (Stratagene USA). *E. coli* strain XL1-blue was transformed with the ligated DNA and transformants were selected on an LB plate with 100 mg/ml of ampicillin. Clones harbouring the apxIV were selected by colony hybridisation of a nitrocellulose replica of the plate with the APIXVA probe. Thus, a plasmid designated pROK7 was isolated and shown to harbour a ClaI insert of approximately 8.0 kb. The first 6736 bp of the ClaI insert were sequenced (SEQ ID NO: 1) and an open reading frame of 4971 nucleotides was identified encoding a protein of 1657 amino acid residues (SEQ ID NO: 2) with a predicted size of approximately 186 kD. The gene was designated apxIV_var1 (see FIG. 3).

EXAMPLE 2

Cloning and analysis of the apxIV gene of *A. pleuropneumoniae* serotype 3

The labelled probe APXIVA (mentioned in example 1) was used to hybridize a Southern blot containing ClaI digested chromosomal DNA from strain HV114. The probe hybridised with a fragment of approximately 7.0 kb. The isolated chromosomal DNA from HV114 was digested with ClaI, and ligated with ClaI digested pBluescript II SK$^-$ (Stratagene USA). *E. coli* strain XL1-blue was transformed with the ligated DNA and transformants were selected on an LB plate with 100 mg/ml of ampicillin. Clones harbouring the apxIV were selected by colony hybridisation of a nitrocellulose replica of the plate with the APXIVA probe. Thus, a plasmid designated pROK5 was isolated and shown to harbour a ClaI insert of approximately 7 kb. The insert was analysed by sequence analysis (SEQID 3). An open reading frame of 4146 bp was identified encoding a protein of 1382 amino acid residues (SEQID 4), with a predicted size of approximately 154 kD. The gene was designated apxIV_var3 (see FIG. 3).

EXAMPLE 3

EXPRESSION OF ApxIV var3-polyhistidine fusion proteins in E. coli

From plasmid pROK5, a deletion clone was made which contains the 3' end of the apxIV gene, starting at the BamHI site (nucleotide No. 2747 in SEQ ID NO: 3) up to the ClaI site at the end of the insert downstream of the apxIV gene. This plasmid was designated pROK1. Using oligonucleotides APXIVAHIA1-L (5'AGCCATATGGGCGAT TTAAATTTCAG-3' (SEQ ID NO: 10)) and APXIVHIS1-R (5'-TATGGATCCTCGTGCTTCTGAGC-3'(SEQ ID NO: 11)) and DNA from plasmid pROK1 as a template, a DNA fragment of 2.1 kb was amplified (see FIG. 4) containing the region from bp 3520 to 5643 in apxIV_var3 (SEQ ID NO: 3) flanked with NdeI and BamHI restriction sites at the 5' and 3' end respectively. After cloning of the NdeI/BamHI digested PCR fragment in expression vector pETHIS-1, digested with the same enzymes, a plasmid designated pJFFapxIV6/10his-1 was obtained. Plasmid pETHIS-1 is a derivative of pET14b (Novagen Inc., Madison, Wis.) where the multiple cloning site has been extended and a region encoding a histidine decamer has been inserted. Consequently, the pJFFapxIV6/10his-1 plasmid contains a translational fusion encoding a histidine hexamer, followed by amino acid residues 653 up to 1360 from SEQ ID NO: 4, followed by a histidine decamer, under the control of a T7 promoter. The plasmid was transferred to E. coli strain HMS174(DE3) with pLysS which contains an IPTG inducible T7 RNA polymerase gene as well as the T & lysozyme gene for increased stability. The strain was grown in LB medium containing 25 mg/ml of chloramphenicol and 100 mg/ml of ampicillin, up to an $OD_{650}$ of 0.5, and induced with isopropyl-b-D-thiogalactopyranoside at a concentration of 10 mM. After the addition of IPTG, the cells were incubated at 37° C. for 2.5 hours, the cells were harvested by centrifugation, and fusion protein with the expected size of 80 kD was isolated in the form of inclusion bodies. The inclusion bodies were solubilized in a solution of 6M guanidine hydrochloride, 300 mM NaCl and 50 mM $NaH_2PO_4$ at pH 8.0 and the 80 kD fusion protein was further purified by immobilized Metal Affinity Chromatography (IMAC) (Schmitt et al., Molecular Biology Reports 18;223–230, 1993) using $Ni^{2+}$ chelated columns (Qiagen AG, Basel). Pure protein was eluted from the column at pH 5.0. Pooled fractions were dialysed against a solution of 300 mM NaCL and 50 mM $NaH_2PO_4$ at pH 8.0. A rabbit was immunised with 500 mg of the polyhistidine fusion product, mixed with 1 volume of Complete Freunds Adjuvant (Difco Labs, Detroit, Mich.). A booster dose of the same amount, mixed with incomplete Freund Adjuvant was given 3 weeks later. Four weeks after the booster, the rabbit was bled and a hyperimmune serum comprising anti-ApxIV toxin antibodies, designated serum 522–409, was obtained.

EXAMPLE 4

Expression of apxIV genes in in vitro grown A. pleuropneumoniae

The A. pleuropneumoniae reference strain from serotype 1 was grown in Columbia broth supplemented with 10 mg/ml of b-NAD and harvested as described (Beck et al., J. Clin. Microbiol., 32;2749–2754, 1994). Adjacent to lanes comprising ApxIA, ApxIIA and ApxIVA-polyhistidine fusion proteins the concentrated culture supernatant was separated by polyacrylamide gel electrophoresis (Laemmli, Nature 227:680–685, 1970) and subjected to a Western blotting procedure (Towbin et al., Proc. Natl. Acad. Sci. USA 76:4350–4354, 1979). The Western blot was reacted with anti-ApxIA- and anti-ApxIIA monoclonal antbodies as described by Beck et al., (J. Clin. Microbiol., 32;2749–2754, 1994), and with anti-ApxIV serum 522–409 (see example 3). The isolated RTX toxin fraction of serotype 1 clearly contains ApxIA and ApxIlA. The presence of ApxIVA could not be demonstrated (see FIG. 5).

EXAMPLE 5

Expression of apxIV genes in A. pleuropneumoniae in vivo during infection

A polyacrylamide gel containing the 80 kD polyhistidine-ApxIV_var3 fusion protein (see example 3) was transferred to a nitrocellulose membrane. The membrane was divided into strips which were reacted with (100-fold dilutions of) convalescent field sera against serotype 1 or sera from a pig, experimentally infected with the serotype 1 reference strain (Frey and Nicolet, Vet. Microbiol., 28;61–73, 1991). The reaction was visualised using alkaline phosphatase-labelled conjugate against rabbit IgG (Kirkegaard Perry Inc., Gaithersburg, Md.) and NBT (4-Nitrobluetetrazolium chloride) and BCIP (5-Bromo-4-chloro-3-indolylphosphate) colour development (see FIG. 6). The serotype 1 field sera, as well as serum from the experimentally infected pig react with the 80 kD polyhistidine-ApxIV_var3 protein. This indicates that the ApxIV protein actually is expressed, is antigenic and induces anti-ApxIV toxin antibodies during A. pleuropneumoniae infection in pigs.

EXAMPLE 6

Figure 4:
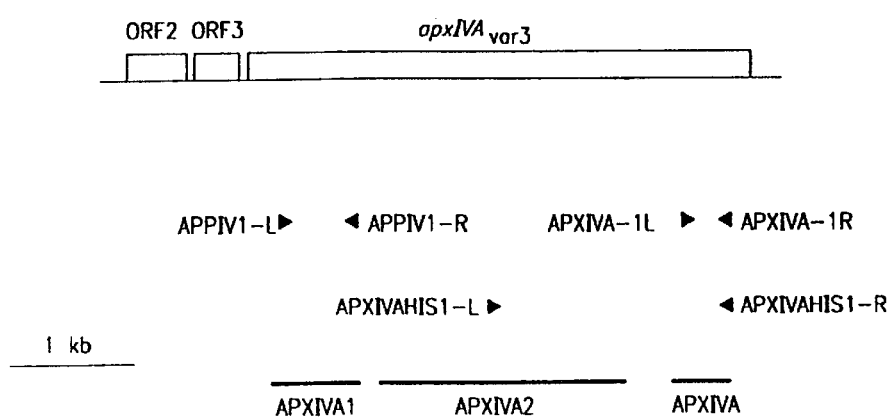
Figure 7:
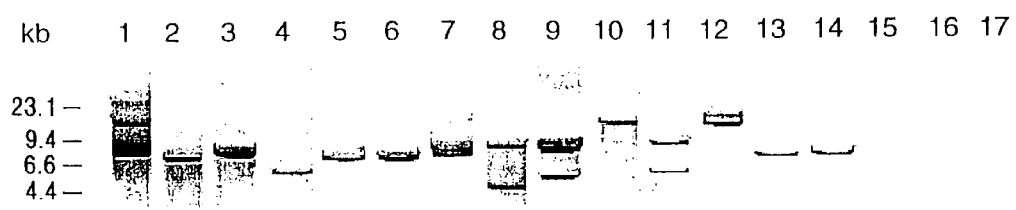

Presence of apxIV genes in all A. pleuropneumoniae serotypes and the absence thereof in non-pleuropneumoniae Actinobacillus-strains using Southern blotting To investigate the presence of the apxIV gene in the various A. pleuropneumoniae serotypes and related bacteria, three probes were made (see FIG. 4). Probe APXIVA is described in example 1. Probe APXIVA2 contains the 2015 bp DNA fragment between the BamHI and NruI sites. The 758 bp probe APPIVA1 was made by PCR amplification with oligos APPIV1-L (5'-GGGACAGTGGCTCAATTAAG-3'(SEQ ID NO: 12)) and APPIV1-R (5'-AGCTGTAAACTCCACCAACG-3'(SEQ ID NO: 13)). All probes were labelled with Digoxigenin-11-dUTP (Boehringer Mannheim) according to the protocol of the manufacturer and hybridised with Southern blots containing ClaI digested chromosomal DNA of all A. pleuropneumoniae reference strains and the HV114 field strain, Actinobacillus suis (ATCC 15558), Actinobacillus rossii (ATCC 27072) and Actinobacillus equuli (ATCC 19392). All three probes react similarly (see FIG. 7 for the results with the APXIVA2 probe). All A. pleuropneumoniae strains react, whereas no hybridisation is observed with the A. suis, A. equuli and A. rossii strains.

EXAMPLE 7

Figure 8:
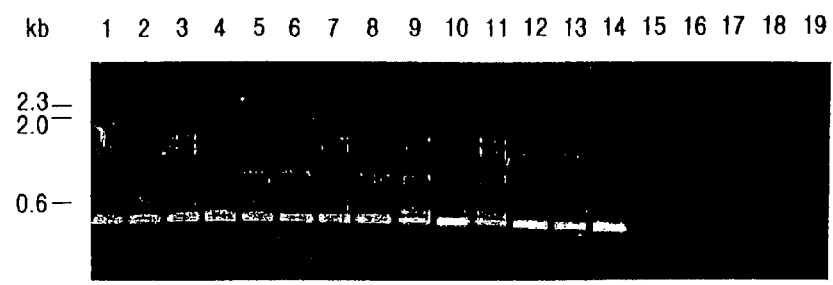

Presence of apxIV genes in A. pleuropneumoniae and related strains using PCR amplification With 50 ng of chromosomal DNA from the various A. pleuropneumoniae serotypes, other Actinobacillus species and P. haemolytica as templates and primers APXIVA-1L (5'-TGGCACTGACGGTGATGA-3' (SEQ ID NO: 8)) and APXIVA-1R (5'-GGCCATCGACTCAACCAT-3' (SEQ ID NO: 9)) PCR amplification was performed. After analysis of the products on an agarose gel, products with the expected size of 442 bp were observed in all *A. pleuropneumoniae* samples, but in none of the other Actinobacillus species (FIG. 8). This indicates that in addition to the results in example 6, also PCR could be used to discriminate *A. pleuropneumoniae* from other Actinobacillus species.

EXAMPLE 8

Overexpression of ApxIV-var1 polyhistidine fusion protein

Starting with plasmid pROK-7 (see example 1) as a template and oligonucleotides APX4/II5-L (5'-CGCCATATGACAAAATTAACTATGCAAC (SEQ ID NO: 14)) and APX4II6-R (5'-CGCGAATTCAGCGA CACAAGAGATAT(SEQ ID NO: 15) as PCR-primers, a PCT fragment was amplified. A sufficient amount of this fragment was then digested with restriction enzymes NdeI and EcoRI and cloned in expression vector pETHIS-1, digested with the same enzymes as described in Example 3. From the resulting plasmid, designated pJFFApxIVA1His1, a 206 kD polyhistidine fusion protein (MW determined in PAGE) of 1841 amino acid residues was overexpressed in *E. coli* as described in Example 3. The protein is encoded in the coding region spanning nucleic acid no. 1132 to 6546 as depicted in SEQ ID NO: 5. The amino acid sequence of the protein is given in SEQ ID NO: 6. In Western blot this product was shown to react with specific anti-ApxIV serum 522–409 (antiserum described in example 3).

EXAMPLE 9

Protection of mice by vaccination with ApxIV against APP challenge

The 206 kD polyhistidine-ApxIV fusion protein as described in Example 8 and a comparable 108 kD polyhistidine-ApxIA-fusion protein, both derived from serotype 1 reference strain 4074 genomic material, were overexpressed as described in example 3. The cell pellet of induced *E. coli* cells was resuspended into PBS buffer (1 g. cell pellet in 6 ml buffer) and sonicated on ice for two times 45 seconds on ice for lysis of the cells. After centrifugation for 20 minutes at 22.000×g at 4° C., the supernatant was discarded and the resulting pellet was washed with a solution of 3M urea (pH 6.3). The urea was removed after centrifugation for 20 minutes at 22.000×g, and the resulting pellet was solubilized in 6M GuanidiniumHCl (pH 8.0). The protein samples were standardised by specific protein content after densitometry of PAGE gels. The samples were diluted with PBS and formulated with an oil adjuvant.

Three groups of 15 mice each, were intraperitoneally immunised with the ApxIV antigen (36.3 microgram), ApxIA antigen (36.3 microgram), or the adjuvant alone. The vaccines were administered in a volume of 0.4 ml. Twenty-four days after the first vaccination, each group of mice was split in two groups of 7 and 8 mice which were boosted with half the amount of antigen. The groups of 7 mice were boosted intrapertoneally in a volume of 0.2 ml and the groups of 8 mice were vaccinated intramuscularly with 0.1 ml in each hind leg. Thirteen days after the booster, the mice were challenged intraperitoneally with 1.5 $10^8$ cfu of a virulent serotype 1 strain.

EXAMPLE 10

Pore forming capacity of ApxIV

Freshly induced *E. coli* cells expressing ApxIV were used as the source of protein for testing pore information in artificial lipid bilayers as described by Maier et al., Infect. Immun., 64; 4415–4423(1996). The methods used for black lipid bilayer experiments have been described previously (Benz et al.; Biochim. Biophys. Acta 511: 305–319 (1978)). Membranes were formed from a 1% solution of asolectin (soybean lecitin type IV-S from Sigma, St. Louis Mo.) in n-decane. Zero current membrane potentials were measured with a Keithley 610 C electrometer 5–10 min. after a 10-fold salt gradient was established across the membranes (Benz et al.; Biochim. Biophys. Acta 551: 238–247 (1979)). The presence of ApxIV resulted in a high frequency of pore formation in the presence of 0.5% cholesterol, with an average single channel conductance (G) of 4 nS.

These results indicate that the ApxIV induces pores into artificial bilayers and is therefore toxic to eukaryotic cells and thus is a virulence factor for *A. pleuropneumoniae*.

LEGEND TO THE FIGURES

FIG. 1: Comparison of ApxIVAvar1 and ApxIVvar3 (var stands for serotype). Graphic representation of the different features found in the C-terminal end. Dashed boxes represent the direct repeat regions in ApxIVA. Bold vertical bars indicate the position of glycine rich nonapeptides, and DNA polymerase family B signatures are indicated by black triangles. The amino acid sequence YSDSANSKK (SEQ ID NO: 16) represents the spacer sequence in the ApxIV Avar3 gene. The sequence segment of ApxIV Avar1 which is deleted in ApxIVAvar3 is also indicated in the figure.

FIG 2: Alignment of the amino acid sequences of direct repeat 1 (A), direct repeat 2 (B) and direct repeat 3 (C) of ApxIVAvar1 and ApxIVAvar3. The copies of each of the direct repeats 1, 2 and 3 are labeled by letters to distinguish them for the sequence comparison. Variant residues are shown in bold letters.

Figure 3:
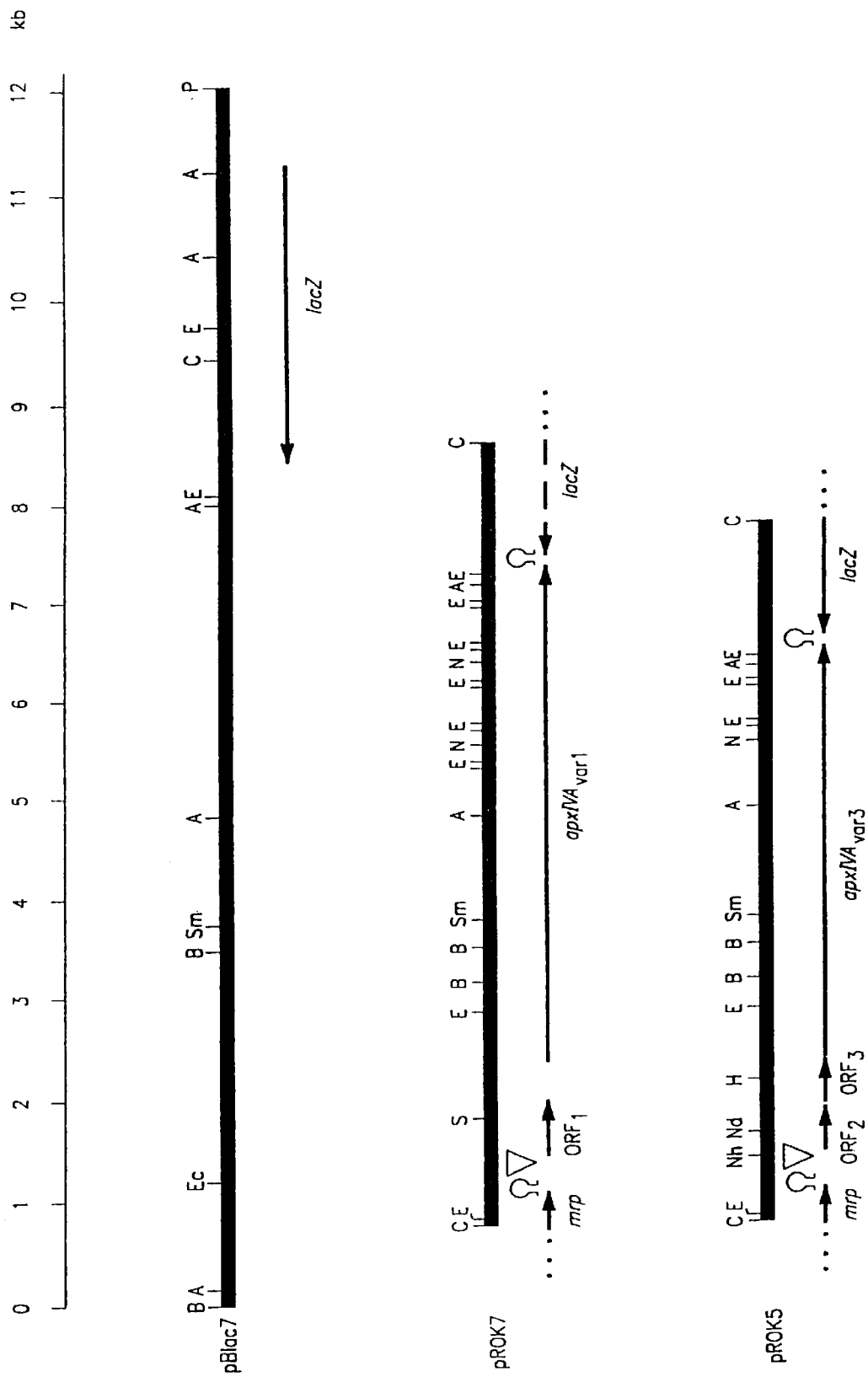

FIG. 3: Partial restriction maps of pBLac7 (Thesis of T. J. Anderson University of Guelph, 1995), pROK7 and pROK5. The different open reading frames (ORF's) are indicated by arrows. The interrupted arrow of lacZ in pROK7 indicates partial sequencing of the gene. Potential rho-independent transcription terminators are indicated (W). Potential transcription start sites are indicated by a triangle. Restriction sites: A=Asp700; B=BamHI; C=ClaI; E=EcoRV; Ec=EcoRI; H=HindIII; N=NruI; Nd=NdeI; Nh=NheI; P=PstI; S=SpeI; Sm=SmaI.

FIG. 4: Location of the various oligonucleotides and probes on the map of the apxIVAvar3 gene.

Figures 5A, 5B, 5C:
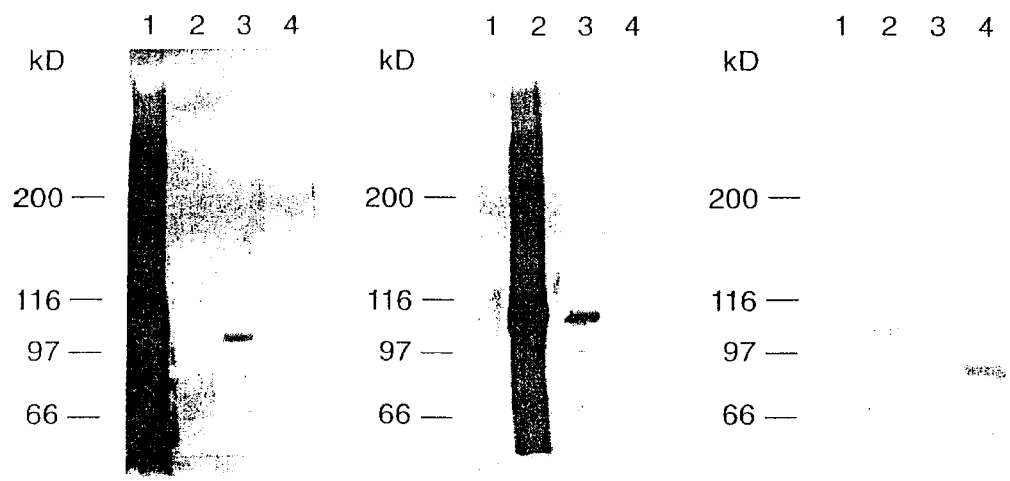

FIG. 5: Expression of ApxIV in in vitro cultivated serotype 1 reference strain 4074. Panel A was reacted with the anti-ApxIA monoclonal antibody, panel B with anti-ApxIIA monoclonal antibody and panel C was reacted with anti-ApxIVA serum 522–409. Lane 1 contains ApxIA-polyhistidine fusion protein, lane 2 contains ApxIIA-polyhistidine fusion protein, lane 3 contains strain 4074 concentrated culture supernatant, lane 4 contains ApxIVA polyhistidine fusion protein.

Figure 6:
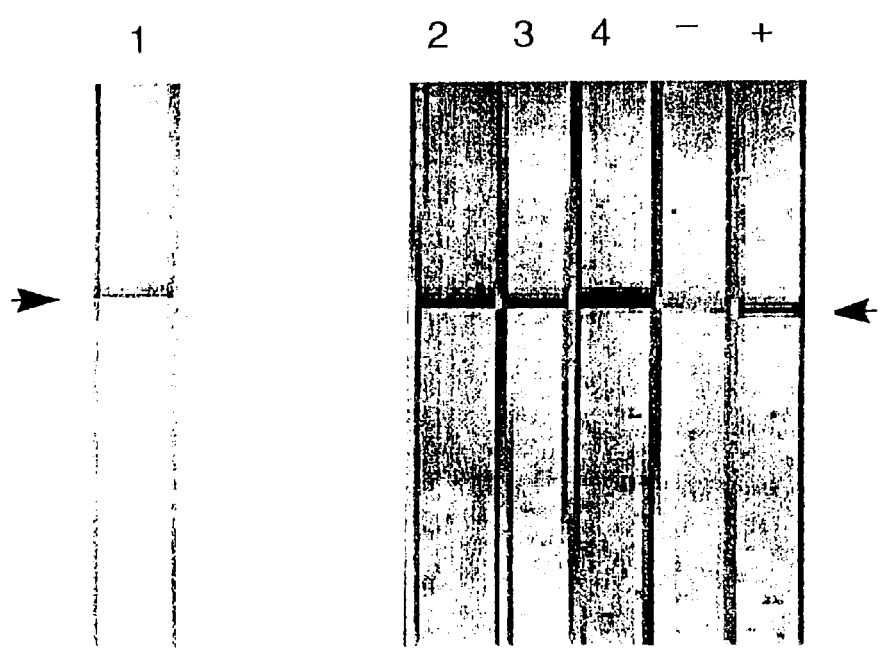

FIG. 6: Immunoblot showing the reactivities of sera from pigs which were experimentally infected with the reference strain of serotype 1 (lane 1) or pig sera from serotype 1 field infections (lane 2–4) with the 80 kD polyhistidine-ApxIV fusion protein. As a positive control (+), serum 522–409 was used, as a negative control (-), polyclonal rabbit serum against ApxI and ApxII (Frey et al., Infect. Immun., 57;2050–2056, 1989) was used as a 1000-fold dilution FIG. 7: Southern blot of ClaI digested genomic DNA hybridised with probe APXIVA2. Lanes 1–13: *A. pleuropneumoniae* reference strains; 1: serotype 1; 2: serotype 2; 3: serotype 3; 4: serotype 4; 5: serotype 5a; 6: serotype 5b; 7:

serotype 6; 8: serotype 7; 9: serotype 8; 10: serotype 9; 11: serotype 10; 12: serotype 11; 13: serotype 12; 14: HV114 field strain; 15 *A. suis* (ATCC 15558); 16: *A. rossii* (ATCC 27072); 17: *A. equuli* (ATCC 19392). Molecular size markers are indicated (in kilobasepairs) on the left.

FIG. 8: PCR amplification of apxIV using primers APXIVA-1L and APXIVA-1R. Lane assignments: lanes 1 to 13 contain the *A. pleuropneumoniae* reference strains from serotypes 1, 2, 3, 4, 5a, 5b, 6, 7, 8, 9, 10, 11 and 12 respectively; lane 14: strain HV114; lane 15: *A. suis* ATCC 15558; lane 16: *A. rossii* ATCC 27072; lane 17: *A. equuli* ATCC 19392; lane 18: *A. lignieresii* ATCC 49236; lane 19: *P. haemolytica* type 1 ATCC 14003. Molecular size markers (in kilobasepairs) are indicated on the left.

What is claimed is:

1. A subunit vaccine for the protection of animals against infection with a bacterium of the species *Actinobacillus pleuropneumoniae*, comprising purified ApxIV toxin and a pharmaceutically acceptable carrier.

2. The vaccine according to claim 1, further comprising an adjuvant.

3. The vaccine according to claim 1, which is in a freeze-dried form.

4. The vaccine according to claim 1, further comprising one or more antigens from pig-pathogenic microorganisms or viruses.

5. The vaccine according to claim 4, wherein said one or more antigens are from microorganisms or viruses selected from the group consisting of Porcine Reproductive Respiratory Syndrome (PRRS) virus, Pseudorabies virus, Porcine Influenza virus, Porcine Parvovirus, Transmissible Gastroenteritis virus, rotavirus, *Escherichia coli*, *Erysipelothrix rhusiopathiae*, *Pasteurella multocida*, *Bordetella bronchiseptica*, *Haemophilus parasuis* and *Streptococcus suis*.

6. A method for the protection of a susceptible animal against *Actinobacillus pleuropneumoniae* infection, comprising administering a vaccine according to claim 1 to the animal.

7. A method for the preparation of a vaccine according to claim 1, comprising admixing purified ApxIV toxin with a pharmaceutically acceptable carrier.

8. A subunit vaccine for the protection of animals against infection with a bacterium of the species *Actinobacillus pleuropneumoniae*, comprising purified ApxIV toxin and an adjuvant.

* * * * *

UNITED STATES PATENT AND TRADEMARK OFFICE
CERTIFICATE OF CORRECTION

PATENT NO. : 6,783,764 B1
DATED : August 31, 2004
INVENTOR(S) : Segers et al.

It is certified that error appears in the above-identified patent and that said Letters Patent is hereby corrected as shown below:

<u>Title page,</u>
Item [74], *Attorney, Agent, or Firm*, should read -- William P. Ramey, III --

Signed and Sealed this

Twenty-sixth Day of October, 2004

JON W. DUDAS
*Director of the United States Patent and Trademark Office*